(12) United States Patent
Giusti et al.

(10) Patent No.: US 11,069,431 B2
(45) Date of Patent: Jul. 20, 2021

(54) INTEGRATED, MOLECULAR, OMICS, IMMUNOTHERAPY, METABOLIC, EPIGENETIC, AND CLINICAL DATABASE

(71) Applicant: The Multiple Myeloma Research Foundation, Inc., Norwalk, CT (US)

(72) Inventors: Kathryn E. Giusti, New Canaan, CT (US); Paul Giusti, New Canaan, CT (US); Daniel Auclair, Middletown, CT (US)

(73) Assignee: The Multiple Myeloma Research Foundation, Inc., Norwalk, CT (US)

( * ) Notice: Subject to any disclaimer, the term of this patent is extended or adjusted under 35 U.S.C. 154(b) by 0 days.

(21) Appl. No.: 16/189,230

(22) Filed: Nov. 13, 2018

(65) Prior Publication Data
US 2019/0147989 A1 May 16, 2019

Related U.S. Application Data

(60) Provisional application No. 62/699,411, filed on Jul. 17, 2018, provisional application No. 62/585,190, filed on Nov. 13, 2017.

(51) Int. Cl.
*G16H 10/60* (2018.01)
*G16H 80/00* (2018.01)
*G16H 50/50* (2018.01)
*G16H 50/70* (2018.01)

(52) U.S. Cl.
CPC ............ *G16H 10/60* (2018.01); *G16H 50/50* (2018.01); *G16H 50/70* (2018.01); *G16H 80/00* (2018.01)

(58) Field of Classification Search
CPC ......... G16H 10/60; G16H 50/50; G16H 80/00
See application file for complete search history.

(56) References Cited

U.S. PATENT DOCUMENTS

| | | | |
|---|---|---|---|
| 6,013,445 A | 1/2000 | Albrecht et al. | |
| 6,196,970 B1 | 3/2001 | Brown | |
| 6,210,891 B1 | 4/2001 | Nyren et al. | |
| 6,839,687 B1 | 1/2005 | Dent et al. | |

(Continued)

FOREIGN PATENT DOCUMENTS

| | | | |
|---|---|---|---|
| JP | 2002024385 A | 1/2002 | |
| JP | 2004185192 A | 7/2004 | |

(Continued)

OTHER PUBLICATIONS

Sarica, A., Cerasa, A., & Quattrone, A. (2017). Random forest algorithm for the classification of neuroimaging data in Alzheimer's disease: A systematic review. Frontiers in Aging Neuroscience, 1-12. 9:329. https://doi.org/10.3389/fnagi.2017.00329 (Year: 2017).*

(Continued)

*Primary Examiner* — Robert A Sorey
*Assistant Examiner* — Kristine K Rapillo
(74) *Attorney, Agent, or Firm* — Wilson, Sonsini, Goodrich & Rosati

(57) ABSTRACT

The disclosure describes a patient registry data system that can be used to aggregate clinical, molecular, and immune parameters involved in disease initiation, progression, and response to treatment. The disclosure can allow participants, researchers, and physicians to visualize data based on parameters, such as participant demographics and immune system data.

18 Claims, 7 Drawing Sheets

(56) References Cited

U.S. PATENT DOCUMENTS

| | | | |
|---|---|---|---|
| 7,115,400 | B1 | 10/2006 | Adessi et al. |
| 7,425,431 | B2 | 9/2008 | Church et al. |
| 7,501,245 | B2 | 3/2009 | Quake et al. |
| 7,593,109 | B2 | 9/2009 | Ulmer |
| 7,648,824 | B2 | 1/2010 | Nyren et al. |
| 7,649,358 | B2 | 1/2010 | Toumazou et al. |
| 7,666,593 | B2 | 2/2010 | Lapidus |
| 7,686,929 | B2 | 3/2010 | Toumazou et al. |
| 7,767,400 | B2 | 8/2010 | Harris |
| 7,790,418 | B2 | 9/2010 | Mayer |
| 7,851,158 | B2 | 12/2010 | McKernan |
| 7,888,015 | B2 | 2/2011 | Toumazou et al. |
| 7,972,820 | B2 | 7/2011 | Mayer |
| 7,985,565 | B2 | 7/2011 | Kawashima et al. |
| 8,114,591 | B2 | 2/2012 | Toumazou et al. |
| 8,135,595 | B2 | 3/2012 | Dalton |
| 10,559,048 | B2 | 2/2020 | Giusti et al. |
| 2002/0046054 | A1 | 4/2002 | Morand et al. |
| 2002/0055100 | A1 | 5/2002 | Kawashima et al. |
| 2003/0033168 | A1* | 2/2003 | Califano ............... G16H 10/60 705/3 |
| 2006/0184493 | A1 | 8/2006 | Shiffman et al. |
| 2007/0015200 | A1 | 1/2007 | Mayer et al. |
| 2007/0055454 | A1 | 3/2007 | Jung et al. |
| 2007/0059783 | A1 | 3/2007 | Packer et al. |
| 2007/0105136 | A1 | 5/2007 | Staudt et al. |
| 2007/0259351 | A1 | 11/2007 | Chinitz et al. |
| 2008/0081330 | A1 | 4/2008 | Kahvejian |
| 2008/0103058 | A1 | 5/2008 | Siddiqi |
| 2008/0133270 | A1 | 6/2008 | Michelson et al. |
| 2008/0213770 | A1 | 9/2008 | Williams et al. |
| 2008/0227210 | A1 | 9/2008 | Smith et al. |
| 2008/0286795 | A1 | 11/2008 | Kawashima et al. |
| 2009/0011943 | A1 | 1/2009 | Drmanac et al. |
| 2009/0099041 | A1 | 4/2009 | Church et al. |
| 2009/0117549 | A1 | 5/2009 | Tan et al. |
| 2009/0156906 | A1 | 6/2009 | Liebman et al. |
| 2009/0163366 | A1 | 6/2009 | Nickerson et al. |
| 2009/0181860 | A1 | 7/2009 | McKernan et al. |
| 2009/0187427 | A1 | 7/2009 | Durand |
| 2009/0264299 | A1 | 10/2009 | Drmanac et al. |
| 2009/0270273 | A1 | 10/2009 | Burns et al. |
| 2009/0307181 | A1 | 12/2009 | Colby et al. |
| 2009/0318298 | A1 | 12/2009 | Kim et al. |
| 2010/0047876 | A1 | 2/2010 | Church |
| 2010/0173363 | A1 | 7/2010 | Buzby |
| 2010/0184045 | A1 | 7/2010 | Thompson |
| 2010/0227321 | A1 | 9/2010 | Harris et al. |
| 2010/0228699 | A1 | 9/2010 | Webber et al. |
| 2010/0268553 | A1 | 10/2010 | Bessette |
| 2011/0172127 | A1 | 7/2011 | Jacobson et al. |
| 2011/0268347 | A1 | 11/2011 | Staker |
| 2013/0185096 | A1 | 7/2013 | Giusti et al. |
| 2014/0142986 | A1 | 5/2014 | Oesterheld et al. |
| 2014/0335505 | A1 | 11/2014 | Holmes |
| 2016/0110523 | A1* | 4/2016 | Francois ............... G16H 10/60 705/2 |
| 2017/0262587 | A1* | 9/2017 | Agarwal ............... G06F 19/325 |
| 2018/0268937 | A1* | 9/2018 | Spetzler ............... G16B 45/00 |
| 2019/0000365 | A1* | 1/2019 | Beyerlein ............ G01N 33/487 |

FOREIGN PATENT DOCUMENTS

| | | | |
|---|---|---|---|
| JP | 2006085631 A | | 3/2006 |
| JP | 2006202235 A | | 8/2006 |
| JP | 2007220113 A | | 8/2007 |
| JP | 2011516077 A | | 5/2011 |
| KR | 20020075265 A | | 10/2002 |
| KR | 20060060163 A | | 6/2006 |
| WO | WO-2011063274 A2 | | 5/2011 |
| WO | WO-2015131169 A2 | | 9/2015 |
| WO | WO 2017/053915 A1 * | 3/2017 | ............ G16H 50/20 |

OTHER PUBLICATIONS

Sarica et al., herein after Sarica (Sarica, A., Cerasa, A., & Quattrone, A. (2017). Random forest algorithm for the classification of neuroimaging data in Alzheimer's disease: A systematic review. Frontiers in Aging Neuroscience, 1-12. 9:329. https://doi.Org/10.3389/fnagi.2017.00329). (Year: 2017).*

Abraham, et al. Functional gene expression analysis of clonal plasma cells identifies a unique molecular profile for light chain amyloidosis. Blood. Jan. 15, 2005;105(2):794-803. Epub Sep. 23, 2004.

Adalsteinsson, et al. Scalable whole-exome sequencing of cell-free DNA reveals high concordance with metastatic tumors. Nat Commun. Nov. 2017;6;( ):1324.

Ahmann, et al. Effect of tissue shipping on plasma cell isolation, viability, and RNA integrity in the context of a centralized good laboratory practice-certified tissue banking facility. Cancer Epidemiol Biomarkers Prev. Mar. 2008;17(3):666-73.

Andrulis, et al. Targeting the BRAF V600E mutation in multiple myeloma. Cancer Discov 2013; 3: 82-869.

Auclair, et al., Utility of clinical-grade sequencing of relapsed multiple myeloma patients; interim analysis of the multiple myeloma research foundation (MMRF) molecular profiling protocol. Blood. 2017; 130:395.

Benard, et al. FGFR3 Mutations are an adverse prognostic factor in patients with t(4;14)(p16;q32) multiple myeloma: an MMRF CoMMpass analysis. Blood. 2017; 131:3027.

Bolli, et al. Heterogeneity of genomic evolution and mutational profiles in multiple myeloma. Nat Commun. 2014; 5:2997.

Brenner, et al. Gene expression analysis by massively parallel signature sequencing (MPSS) on microbead arrays, Nat Biotechnol, Jun. 2000;18(6):630-4.

Chapman, et al. Initial genome sequencing and analysis of multiple myeloma. Nature. 2011; 471 (7339): 467-72.

Chomczynski, et al. Single-step method of RNA isolation by acid guanidinium thiocyanate-phenol-chloroform extraction. Anal Biochem. Apr. 1987;162(1):156-9.

European search report and opinion dated Oct. 27, 2014 for EP Application No. 12810899.0.

Fonseca, et al., Real-world outcomes for maintenance treatment sequencing after receiving lenalidomide, bortezomib, and dexamethasone induction in patients with newly diagnosed multiple myeloma (NDMM) followed by autologous stem cell transplant (ASCT). Blood. 2017; 130:3463.

Heuck, et al., Inhibiting MEK in MAPK pathway-activated myeloma, Leukemia. 2016; 30 (4):976-8.

International search report and written opinion dated Dec. 19, 2012 for PCT/US2012/046281.

Krejcik, et al. Daratumumab depletes CD38+ immune regulatory cells, promotes T-cell expansion, and skews T-cell repertoire in multiple myeloma. Blood. 2016; (3)384-94.

Kis, et al., Circulating tumour DNA sequence survival impact of self-reported symptom and psychological distress among patients with multiple myeloma. Blood. 2017; 13:679.

Kumar, et al. Immune therapies in multiple myeloma. Clin Cancer Res, 2016; 22(22); 5453-5460.

Kyle, et al. Monoclonal gammopathies of undetermined significance: a review. Immunol Rev. Aug. 2003;194:112-39.

Lawrence, et al. Discovery and saturation analysis of cancer genes across 21 tumour types. Nature. 2014; 505(7484):495-501.

Lemery, et al. First FDA approval agnostic of cancer site—when a biomarker defines the indication. N Engl J Med. 2017; 377(15):1409-1412.

Lohr, et al. Golub TR. genetic interrogation of circulating multiple myeloma cells at single-cell resolution. Sci Transl Med. Nov. 2016; 8(363):363ra147.

Lohr, et al. Widespread genetic heterogeneity in multiple myeloma: implications for targeted therapy, Cancer Cell. 2014; 25(1):91-101.

Minges Wols, et al. Plasma cell purification from murine bone marrow using a two-step isolation approach. J Immunol Methods. Jan. 1, 2008;329(1-2):219-24. Epub Oct. 23, 2007.

(56) References Cited

OTHER PUBLICATIONS

Manojlovic, et al. Comprehensive molecular profiling of 718 multiple rnyelomas reveals significant differences in mutation frequencies between African and European descent cases. PLoS Genet. Nov. 2017; 13(11).

Miller, et al. High somatic mutation and neoantigen burden are correlated with decreased progression-free survival in multiple myeloma. Blood Cancer J. Sep. 2017; 7(9).

Mishima et al. The mutational landscape of circulating tumor cells in multiple myeloma. Cell Rep. 2017; 19(1):218-224.

Richter, et al. Incidence and survival impact of self-reported symptom and psychological distress among patients with multiple myeloma. Blood. 2017; 130:679.

Sitapati, et al., Integrated precision medicine: the role of electronic health records in delivering personalized treatment. Wiley Interdiscip Rev Syst Biol Med. May 2017; 9(3).

Office Action dated Apr. 3, 2017 for U.S. Appl. No. 13/546,780.

Ozsolak, et al. Direct RNA sequencing. Nature. Oct. 8, 2009;461(7265):814-8. Epub Sep. 23, 2009.

Reinartz, et al. Massively parallel signature sequencing (MPSS) as a tool for in-depth quantitative gene expression profiling in all organisms. Brief Funct Genornic Proteomic. Feb. 2002;1(1):95-104.

U.S. Appl. No. 13/546,780 Office Action dated Apr. 21, 2015.
U.S. Appl. No. 13/546,780 Office Action dated Jan. 16, 2018.
U.S. Appl. No. 13/546,780 Office Action dated Jan. 6, 2016.
U.S. Appl. No. 13/546,780 Office Action dated Jul. 7, 2016.
U.S. Appl. No. 13/546,780 Office Action dated Sep. 26, 2014.

Wang, et al., MAX is an epigenetic sensor of 5-carboxylcytosine and is altered in multiple myeloma. Nucleic Acids Res. 2017; 46(5):2396-2407.

Witzig, et al. Measurement of apoptosis and proliferation of bone marrow plasma cells in patients with plasma cell proliferative disorders. Br J Haematol. Jan. 1999;104(1):131-7.

International Search Report and Written Opinion of PCT/US18/60751 dated Jan. 24, 2019.

Lagana, et al. Integrative network analysis identifies novel drivers of pathogenesis and progression in newly diagnosed multiple myeloma. Leukemia. 2018; 32(1): 120-130.

International search report with written opinion dated Jan. 31, 2018 for EP Application No. 17182516.

Khoury, et al., Protocol for the Examination of Specimens From Patients With Plasma Cell Neoplasms Protocol applies to plasma cell neoplasms in bone marrow and extramedullary sites TMN, 7th Edition Protocol (2015).

* cited by examiner

INTEGRATED, MOLECULAR, OMICS, IMMUNOTHERAPY, METABOLIC, EPIGENETIC, AND CLINICAL DATABASE

CROSS-REFERENCE

This application claims priority to U.S. Application No. 62/699,411, filed Jul. 17, 2018, and U.S. Application No. 62/585,190, filed Nov. 13, 2017, the content of each of which is incorporated herein by reference in its entirety.

BACKGROUND

Multiple myeloma is a cancer formed by malignant plasma cells. When plasma cells become cancerous, the cancerous plasma cells can produce a tumor called a plasmacytoma. If a subject has more than one plasmacytoma, the disease is called multiple myeloma. There is a need for a deeper understanding of the clinical, molecular, and immune parameters involved in disease initiation, progression, and response to treatment.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In some embodiments, the invention provides a computer program product comprising a non-transitory computer-readable medium having computer-executable code encoded therein, the computer-executable code adapted to be executed to implement a method comprising: a) providing a healthcare management system, wherein the healthcare management system comprises: i) a data collection module; ii) a parameter selection module; iii) an analytics module, wherein the analytics module analyzes molecular biology data; iv) a visualization module, wherein the visualization module illustrates the data analyzed by the analytics module; and v) an output module comprising a patient-facing interface; b) collecting by the data collection module a subject's health data from a data source; c) selecting by the parameter selection module a set of parameters to use to analyze the subject's health data; d) analyzing by the analytics module the subject's health data using the set of parameters to provide an analysis; e) generating by the visualization module a visual representation of the analysis, and sending the visual representation of the analysis to the output module; f) outputting the visual presentation of the analysis.

DETAILED DESCRIPTION OF THE INVENTION

Figure 1:
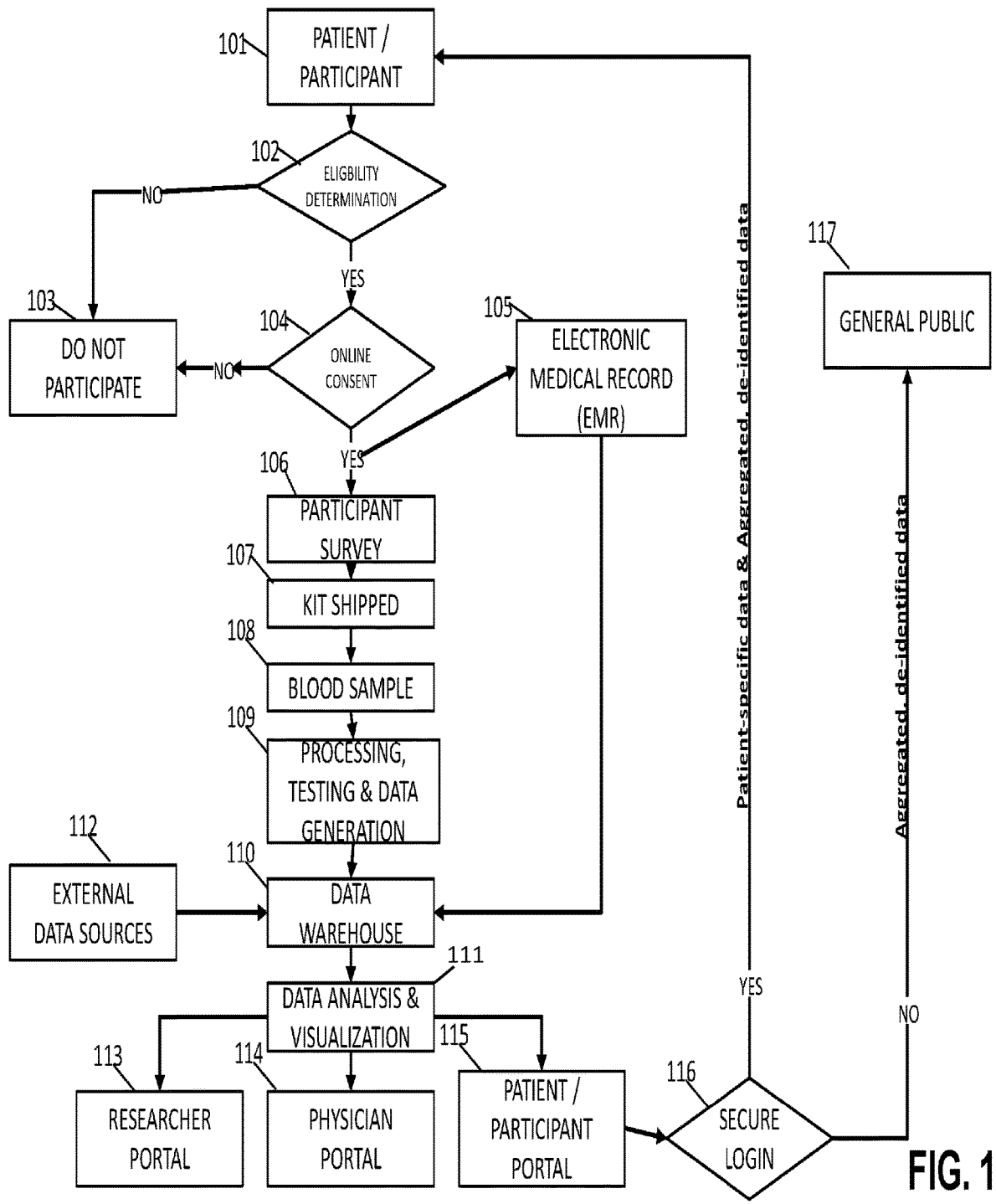
FIG. 1 illustrates how a patient's or a participant's electronic consent form can allow data to be, collected, analyzed, visualized and deposited into the integrated, molecular, omics (e.g., genomics, proteomics, lipidomics), immunotherapy, metabolic, epigenetic, and clinical database.

The present disclosure provides unique combinations of different technologies, approaches and methods that allow for collecting, aggregating, analyzing, reporting and visualizing genomic, immune, and clinical data from individuals, particularly those individuals with a disease or potential for a disease. Molecular and immune determinants of disease initiation, progression and response to treatment can be defined through assessment of blood biomarkers. Molecular and immune biomarkers can be identified in each patient and the data can be correlated with each individual's unique clinical outcome profile. A bank of biospecimens and comprehensive research data linked through an innovative data platform can be created to accelerate a cure for multiple myeloma. Subjects can be made active participants in research by keeping subjects engaged throughout the course of the study.

Features of the different technologies, approaches and methods include, but are not limited to, direct communication with an individual and online features allowing for participation consent in an investigational study; a consent that triggers communication between the individual and a third-party medical specimen collection firm to meet and collect biologic samples (e.g., blood, urine, stool) from the individual; transfer of the samples by the medical specimen collection firm to an approved laboratory to derive genomic, immune, clinical and other data regarding the individual's medical condition, digital organization, curation, and storage of the data from the medical laboratory in a secure database; in parallel to the previous features, access through electronic or other methods to the individual's medical records located at hospitals, medical centers, physician's offices and other places triggered by the consent; organization, curation and storage of the medical records in the secure database coupled with the individual's medical laboratory data; periodic access of the medical records and data addition to the individual's data so data remain current; creation of a secure database by combining the medical laboratory results with the medical records that are regularly updated; an environment created by the database to conduct detailed analysis specific to the individual's medical condition and to compare the condition to other individuals or groups of individuals; comparison of treatment regimes, clinical outcomes and development recommended treatment decisions; analyses made available online to the individuals in an easily understood, consumer-friendly personal visualization format; communication of the personal visualization format with the individual so that the individual remains engaged and provides additional information to the database; availability of the analyses to physicians in a manner that, in some embodiments, provides a decision-support tool aiding the physician in making treatment decisions; accessibility of the database to researchers, analysts or others who are authorized to obtain data through a data portal; a structured database that allows for collection, aggregation and structuring of the data so data from third parties can be accepted; and an integration of the entire system so that the information can flow seamlessly by and between any third-party partners.

A deeper understanding of the clinical, molecular, and immune parameters involved in disease initiation, progression, and response to treatment is necessary to utilize precision medicine for the treatment of a disease, such as, but not limited to, cancer. Collecting information at the population level is crucial for generating evidence needed to utilize precision medicine. The present disclosure describes an integrated, molecular, omics (included, but not limited to, genomics, proteomics, lipidomics), immunotherapy, metabolic, epigenetic, and clinical database that can be used to collect, analyze, visualize and share data from participants, researchers, physicians, and the general public.

Voluntary, informed electronic consent can be obtained from participants that allow for identification and use of peripheral blood for research purposes; collection of blood at enrollment for molecular and immune analyses; submission of additional blood samples, if a change in a participant's disease status occurs, or if the researchers discover a finding of interest (the additional sample can be the same amount as that taken at the beginning of the study and the participant can decline to donate additional blood samples at any time); banking of the participant's specimens or materials derived from specimens; future research utilizing the participant's specimens; linking of research information derived from the patient's specimens to clinical information; sharing and publication of de-identified genomic data; and future contact for the purpose of enrollment into additional clinical trials, as well as institutional review board (IRB) approved future research surveys to be completed voluntarily by the participant.

Studies can be performed on the patient-derived materials, including, but not limited to, molecular profiling using, for example, next-generation sequencing technologies. Molecular profiling of participants blood biopsies can be performed using liquid biopsy. Non-molecular studies including, but not limited to, functional immune measurements, metabolic and proteomic analyses can also be performed. Clinical data that is linked to the samples can be obtained by gathering the patient's electronic medical records. The sharing of specimens and data collected in collaborative projects with investigators outside of the protocol, under appropriate federal, state, and institutional guidelines promotes the translational study of various diseases (e.g., multiple myeloma), and hasten the development of effective methods to prevent and treat various diseases (e.g., multiple myeloma). Participants can be actively involved in the research by receiving general information and results. The general information and results can be in the form of aggregated research results and subsequently with a future amendment in the form of clinical-grade information that could be used by the patient's treating clinician as additional data to be considered in the care of the patient. Participants can be offered to participate in surveys pertinent to the integrated, molecular, omics (included, but not limited to, genomics, proteomics, lipidomics), immunotherapy, metabolic, epigenetic, and clinical database, so research experience can be captured.

Applications

The integrated clinical database disclosed herein can be used to collect, analyze, visualize, and share data from participants with cancerous and non-cancerous diseases. The integrated, molecular, omics (included, but not limited to, genomics, proteomics, lipidomics), immunotherapy, metabolic, epigenetic, and clinical database of the disclosure can be used to collect, analyze, visualize and share data from participants with a disease such as, but not limited to, type 1 diabetes, type 2 diabetes, cystic fibrosis, Parkinson's disease, Alzheimer's disease, arthritis, epilepsy, heart disease, HIV/AIDS, hepatitis, or kidney disease, or any precursor conditions. In some embodiments, the integrated, molecular, omics (included, but not limited to, genomics, proteomics, lipidomics), immunotherapy, metabolic, epigenetic, and clinical database can be used to collect and share data from participants with cancer, for example, multiple myeloma or its precursor conditions. In some embodiments, the patient has, or is diagnosed with a cancer, such as, but not limited to, acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, bowl cancer, cancers of the blood, craniopharyngioma, ependymoblastoma, ependymoma, medulloblastoma, medulloeptithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CIVIL), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, non-melanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom macroglobulinemia, Wilms Tumor and/or other tumors.

In some embodiments, the integrated molecular, omics (included, but not limited to, genomics, proteomics, lipidomics), immunotherapy, metabolic, epigenetic and clinical database can be used to collect, analyze, visualize and share data from participants with multiple myeloma or a precursor conditions. Multiple myeloma is a cancer formed by malignant plasma cells. Normal plasma cells are found in the bone marrow and are an important part of the immune system. When plasma cells become cancerous, the cancerous plasma cells can produce a tumor called a plasmacytoma. Plasmacytomas generally develop in the bone, but can also be found in other tissues. If a subject has only a single plasma cell tumor, the disease is called an isolated or solitary plasmacytoma. If a subject has more than one plasmacytoma, the disease is called multiple myeloma.

Normal cells can transform into cancer cells. Normal cells can accumulate genomic alterations, which contribute to unregulated cell growth in the body. These proliferating malignant cells can secrete certain factors such as vascular endothelial growth factor (VEGF), which can bring blood supply to the growing malignancy to support further growth. In some embodiments, the malignant cells can crowd out and inhibit the production of normal cells in the body, interfering with normal organ functions and eventually causing death.

TABLE 1 shows some primary and secondary symptoms a subject with multiple myeloma can exhibit.

TABLE 1

| Symptom | Cause/Complication |
| --- | --- |
| Low blood cell count | Decrease in number of normal blood cells (red blood cells that carry oxygen, white blood cells that fight infection, platelets that stop bleeding). Caused when myeloma cells grow in the marrow and crowd out normal blood cell growth. Can also be caused by certain myeloma therapies. |
| Anemia | Decreased levels of hemoglobin found in the blood. Due to decreased number of red blood cells in the blood. Can cause weakness, fatigue, shortness of breath. |
| Impaired immunity | Increased risk of illness and infection due to low numbers of white blood cells. |
| Bone damage and bone loss | Myeloma cells activate cells in the bones that contribute to bone destruction. This bone degradation can cause bone pain, bone fractures and also release high levels of calcium into the blood (hypercalcemia, see below) |
| Impaired kidney function and kidney failure | Excess M protein secreted by myeloma cells into the blood, and excess calcium in the blood due to bone destruction, can affect kidney function. This can lead to decreased urine production and other serious issues. |
| Hypercalcemia | Excess calcium in the blood due to bone destruction caused by myeloma cells. Can cause loss of appetite, increased thirst and urination, restlessness, confusion, nausea and vomiting. |
| Peripheral neuropathy | Pain, tingling, burning, numbness, or sensitivity to temperature in extremities. Can be caused by deposition of excess abnormal proteins that affect the peripheral nervous system in the extremities. Can also be caused by certain myeloma therapies. |
| Gastrointestinal problems | Medications used to treat multiple myeloma can cause constipation, diarrhea, nausea, and vomiting. |

*Amyloidosis can also involve low blood pressure and can result in kidney, heart, or liver failure.

Several treatment options are available to subjects with multiple myeloma. TABLE 2 shows some of the available therapies, descriptions of the mechanisms of action, and methods of using the therapeutics.

TABLE 2

| Approved Therapy | Description |
| --- | --- |
| Proteasome Inhibitors<br>Velcade ® (bortezomib)<br>Kyprolis ® (carfilzomib)<br>Ninlaro ® (ixazomib) | This class of drugs kills myeloma cells by not allowing them to degrade excess proteins that build up inside the cells. The excess proteins are toxic and cause the myeloma cells to die. |
| Immunomodulatory Drugs (IMiDs)<br>Revlimid ® (lenalidomide)<br>Pomalyst ® (pomalidomide)<br>Thalomid ® (thalidomide) | This class of drugs regulates certain aspects of the immune system, activating immune cells, preventing growth signals for myeloma cells, and can directly kill myeloma cells. |
| Steroids<br>Decadron ® (dexamethasone)<br>Deltasone ® (prednisone) | This class of drugs can kill myeloma cells at high doses; combined with other myeloma drugs, they can also decrease inflammation and reduce nausea and vomiting caused by chemotherapy and other myeloma treatments. |
| HDAC Inhibitors<br>Farydak ® (panobinostat) | This drug works by stopping growth of myeloma cells by inhibiting the activity of the histone deacetylase (HDAC) enzyme. |
| Monoclonal Antibodies (MAbs)<br>Darzalex ® (daratumumab)<br>Empliciti ® (elotuzumab)<br>Xgeva ® (denosumab) | MAbs are a type of immunotherapy. Darzalex and Empliciti target and bind to specific proteins found on myeloma cells, tagging them for destruction by the body's immune cells. Xgeva helps prevent skeletal complications by binding to the RANKL protein, thereby deactivating certain bone cells and decreasing bone destruction. |
| Chemotherapy<br>Doxil ® (liposomal doxorubicin)<br>Evomela ® (melphalan)<br>Cytoxan ® (cyclophosphamide)<br>VP-16 ® (etoposide)<br>Adriamycin ® (doxorubicin)<br>Treanda ® (bendamustine)<br>Oncovin ® (vincristine) | Can be used alone or in combination to kill cancer cells. These drugs work by killing cells that are in the process of dividing; they can affect healthy cells as well as cancer cells, which increases toxic side effects. They are usually used in preparation for stem cell transplant. |

In some embodiments, the integrated molecular, omics (included, but not limited to, genomics, proteomics, lipidomics), immunotherapy, metabolic, epigenetic, and clinical database can be used to collect, analyze, visualize and share data from participants with Parkinson's disease and its precursors. Parkinson's disease is a long-term degenerative disorder of the central nervous system that mainly affects the motor system. The motor symptoms of the disease result from the death of cells in the substantia nigra, a region of the midbrain, resulting in a pack of dopamine in the substantia nigra. Cell death in the substantia nigra involves the build-up of proteins into Lewy bodies in the neurons.

Diagnosis of Parkinson's disease is mainly based on symptoms and tests such as, but not limited to, neuroimaging. TABLE 3 shows some motor and non-motor symptoms a subject with Parkinson's disease can exhibit.

TABLE 3

| Motor symptoms |
| --- |
| Bradykinesia (slowness of movement) |
| Rigidity (stiffness of movement) |
| Tremor (involuntary shaking of the hands, feet, arms, legs, jaw or tongue; usually more prominent at rest) |
| Postural instability (tendency to fall, usually when pivoting) |
| Non-motor symptoms |
| Mood changes (depression, anxiety, irritability) |
| Cognitive changes (memory problems, personality changes, psychosis/hallucinations) |
| Orthostatic hypotension (lightheadedness and low blood pressure when standing) |
| Constipation and early satiety (a feeling of fullness after eating small amounts) |
| Hyperhidrosis (excessive sweating) |
| Seborrhea (oily skin) |
| Urinary urgency and incontinence |
| Sexual dysfunction |
| Loss of sense of smell |
| Sleep disorders |
| Insomnia, excessive daytime sleepiness (EDS), rapid eye movement behavioral disorder (RBD) or active dreaming, dream enactment, involuntary movements and vocalizations during sleep, restless leg syndrome (RLS), periodic limb movement disorder (PLMD) |
| Fatigue |
| Sensory problems (pain, tightness, tingling, burning) |
| Mixed motor and non-motor symptoms |
| Sialorrhea (drooling due to slowed swallowing) |
| Speech and swallowing problems |

Treatment for Parkinson's disease is directed at improving symptoms. TABLE 4 summarizes the medications used in Parkinson's disease.

TABLE 4

| Treatment | Description |
| --- | --- |
| Levodopa | |
| Carbidopa/levodopa | Monotherapy or combination therapy for slowness, stiffness, and tremor |
| Carbidopa/levodopa/entacapone | Replacement for carbidopa/levodopa, for motor fluctuations |
| Dopamine agonists | |
| Ropinirole, Ripinirole XL | Monotherapy or combination therapy for slowness, stiffness, and tremor |
| Pramipexole, Pramipexole ER | Monotherapy or combination therapy for slowness, stiffness, and tremor |
| Ritigotine | Monotherapy or combination therapy for slowness, stiffness, and tremor |
| Apomorphine | Adjung therapy for sudden wearing off; injectable, fast-acting dopaminergic drug |

TABLE 4-continued

| Treatment | Description |
| --- | --- |
| MAO-B inhibitors | |
| Selegiline | Monotherapy for slowness, stiffness, and tremor; adjunct therapy for motor fluctuations |
| Rasagiline | Monotherapy for slowness, stiffness, and tremor; adjunct therapy for motor fluctuations |
| Zydis selegiline HCl | Monotherapy for slowness, stiffness, and tremor; adjunct therapy for motor fluctuations |
| COMT-inhibitors | |
| Entacapone | Combination therapy with levodopa for motor fluctuations |
| Tolcapone | Combination therapy with levodopa for motor fluctuations |
| Other antiparkinson medications | |
| Amantadine | Monotherapy for slowness, stiffness, and tremor; combination therapy with levodopa for levodopa-induced motor fluctuations; especially helpful for suppressing dyskinesia |
| Anticholinergics | |
| Trihexyphenidyl | Monotherapy or combination therapy, predominantly for tremor in younger people |
| Benztropine | Monotherapy or combination therapy, predominantly for tremor in younger people |

Integrated, Molecular, Omics (Included, but not Limited to, Genomics, Proteomics, Lipidomics), Immunotherapy, Metabolic, Epigenetic, and Clinical Database The integrated, molecular, omics (included, but not limited to, genomics, proteomics, lipidomics), immunotherapy, metabolic, epigenetic, and clinical database disclosed herein can allow patients or participants to register and enter data into a patient or participant portal; aggregate and analyze the data, share the resulting information with researchers and physicians, and analyze, visualize, and share information among patients, participants, researchers, physicians, pharmaceutical companies, payors, the general public, and others. In some embodiments, patients and participants can provide self-reported data. In some embodiments, researchers, oncologists, or stationary or mobile phlebotomists can provide longitudinal clinical data and/or blood, bone marrow, tumor, tissue, or other biological samples to a central location. The data generated by the samples can then be processed, curated, and stored in a database. The longitudinal clinical data can be provided through the transmission of electronic medical record (EMR) or electronic health record (EHR), or other methods. In some embodiments, data can be obtained from an external database. All of the data from the various sources can be collected, aggregated, analyzed and stored in the database.

Comprehensive immune-based characterization of biological samples promotes the qualitative and quantitative assessment of disease development and progression during a therapeutic intervention. In some embodiments, comprehensive immune-based characterization of biological samples can improve prognostic and diagnostic interpretation to inform therapeutic treatment and clinical outcomes. In some embodiments, comprehensive immune-based characterization of a biological sample can promote the qualitative and quantitative assessment of the progression of a condition (e.g., multiple myeloma) or a precursor condition in a participant during therapeutic intervention, and improve the clinical outcome of the therapeutic intervention.

The database can be curated, analyzed, and processed to provide information through online tools to researchers, medical professionals, patients, participants, pharmaceutical companies, payors, the general public, and others. The information can include interactive and/or visual components to improve the understanding of the information provided. The information can be data-driven, evidence-based, clinically relevant, or statistically relevant to advance research and improve patient or participant outcomes. In some embodiments, the integrated, molecular, omics (included, but not limited to, genomics, proteomics, lipidomics), immunotherapy, metabolic, epigenetic, and clinical database disclosed herein can include a social media component that is used to communicate with participant communities and the general public.

Figure 7:
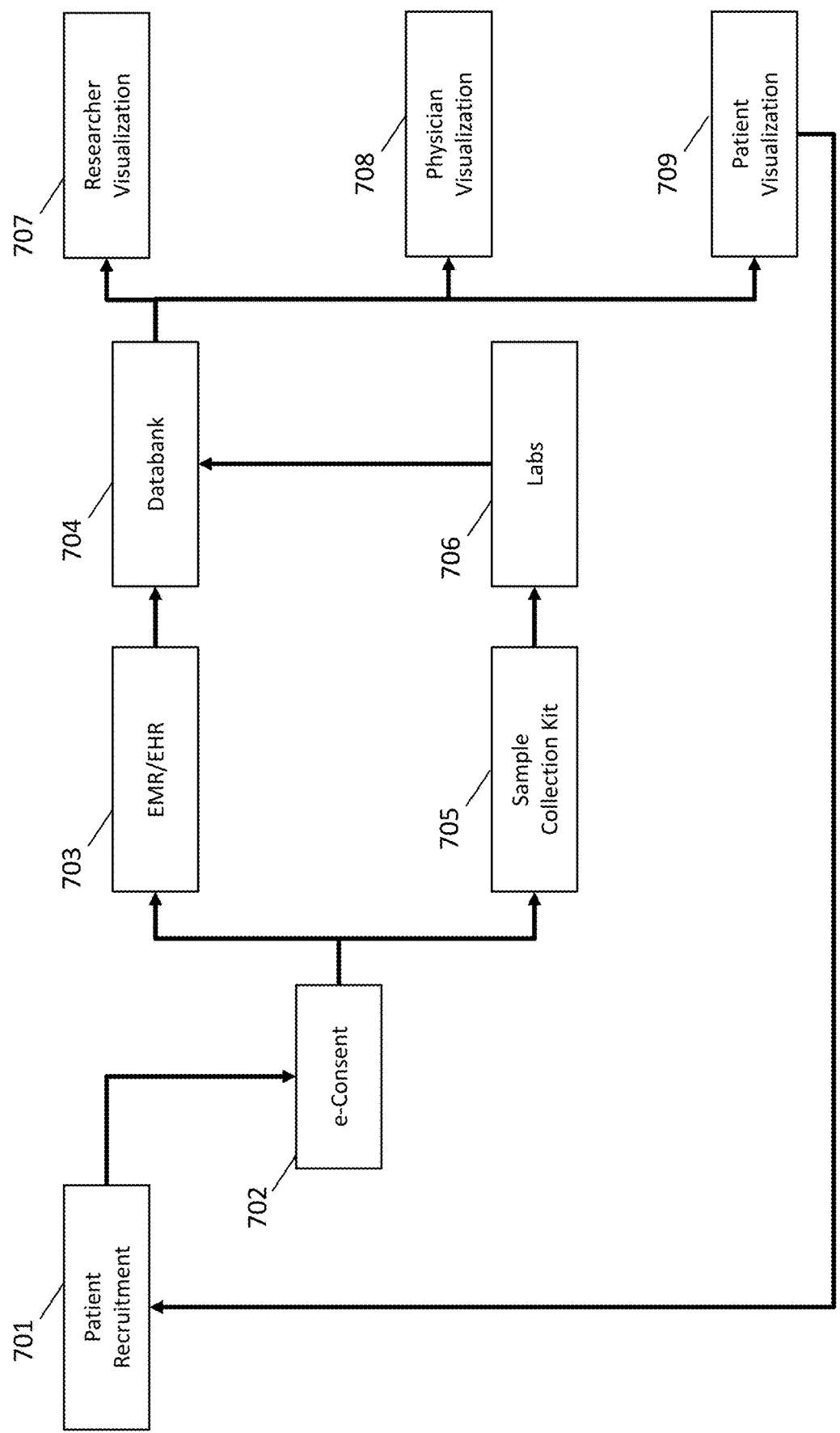
FIG. 7 illustrates how a patient's or a participant's electronic consent form can allow data to be, collected, analyzed, and visualized into the integrated, molecular, omics (e.g., genomics, proteomics, lipidomics), immunotherapy, metabolic, epigenetic, and clinical database.

FIG. 7 illustrates an example integrated, molecular, omics (included, but not limited to, genomics, proteomics, lipidomics), immunotherapy, metabolic, epigenetic, and clinical database. The study facilitates the use of specimens obtained directly from patients or participants through blood collection to correlate clinical information generated during the course of the patient or participant's clinical care or evaluation. A patient or participant (701) diagnosed with a disease or known precursor condition to a disease is identified and recruited to participate in the integrated clinical database. If the patient or participant consents to the online consent form (702), the patient or participant's EMR and/or EHR (703) are released and entered into a databank (704). A patient or participant's consent to the online consent form (702) triggers a sample collection kit to be shipped (705) to the patient or participant. A blood sample is collected from eligible patients or participants through a mobile phlebotomy appointment to be scheduled by the consented participant and the blood sample is processed and tested in a lab (706). Through the consenting process, participants or patients can be asked to authorize linkage of EMR information. The sample data are generated from the sample collected from the patient or participant, and the information is sent to the databank (704). Samples collected can be processed to produce in-depth genomic and immune data that can be aggregated into the database (e.g., a cloud-based platform boasting a series of impressive tools and capabilities for the seamless aggregation, integration and analysis of large collections of datasets). The data can be sent to a visualization module for outputting and visualizing the data. Information from the Visualization process is then sent for researcher visualization (707), a physician visualization (708), and/or a patient participant visualization (709).

FIG. 1 illustrates an example integrated, molecular, omics (included, but not limited to, genomics, proteomics, lipidomics), immunotherapy, metabolic, epigenetic, and clinical database. A patient or participant (101) first submits information to determine eligibility (102), which includes a patient or participant diagnosed with a disease or known precursor condition to a disease. If the patient or participant is not eligible, then the patient or participant does not participate in the integrated clinical database (103). If the patient or participant is eligible, the patient or participant agrees to an online consent form (104). If the patient or participant does not consent to the online consent form (104), the patient or participant does not participate in the integrated clinical database (103). If the patient or participant consents to the online consent form (104), the patient or participant's EMR and/or EHR (105) are released and entered into a data warehouse (110). A patient or participant's consent to the online consent form (102) triggers a participant survey (106). The participant survey can be a medical survey taken to collect additional information about the participant's medical background. Once the survey is complete, a sample collection kit is shipped (107) to the patient or participant. A blood sample is collected from the patient or participant (108). The blood sample is processed and tested, and sample data is generated (109) from the sample collected from the patient or participant, and the information is sent to the data warehouse (110). The data can be sent to a data analysis and visualization module (111) for outputting and visualizing the data. Data from external data sources (112) can also be entered into the data warehouse (110). Information from the Data Analysis and Visualization process (111) is analyzed and then sent to a researcher portal (113), a physician portal (114), and/or a patient participant portal (115). A patient or participant with secure login information (116) can access patient-specific or participant-specific data, access aggregated, de-identified data, and input or change patient or participant information (101). For patients, participants, and/or subjects without secure login information (116) (i.e., the general public (117)) aggregaged and de-dentified data can be accessed and visualized.

Figure 6:
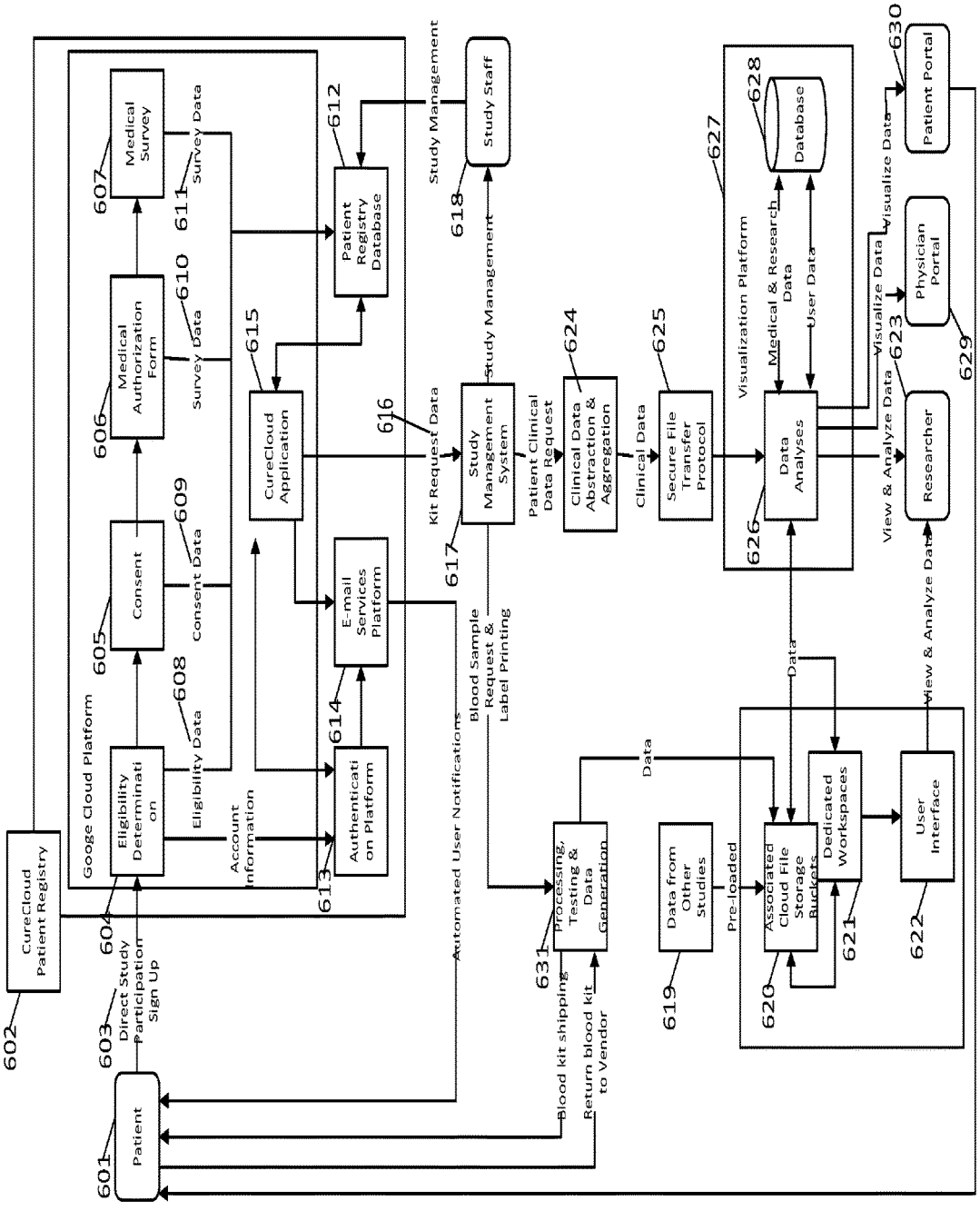
FIG. 6 illustrates an integrated, molecular, omics (included, but not limited to, genomics, proteomics, lipidomics), immunotherapy, metabolic, epigenetic, and clinical data flow diagram.

FIG. 6 illustrates another example integrated, molecular, omics (included, but not limited to, genomics, proteomics, lipidomics), immunotherapy, metabolic, epigenetic, and clinical data flow diagram. A patient or participant (601) enrolls in a study using a patient or participant registration portal (602) comprising an eligibility and electronic consenting process. The patient or participant first signs up for a direct study participation (603) by entering into a research initiative home page. The patient or participant initiates the enrollment process by clicking on the call-to-action button on the home page and encounters a set of eligibility questions. The patient's or participant's eligibility (604) is determined using at least one short question (e.g., two questions, both of which can be answered with the affirmative "yes" to be eligible for the study). If the participant is eligible, the participant is asked to verify his or her e-mail address using an e-mail sent to the participant with a link for e-mail verification. Once the e-mail address is verified, the participant encounters the electronic consent step (605) of the enrollment process. If the participant consents to the study, the participant encounters a medical authorization form (606) that details the participant's contact information, the participant's physician(s), and institutions where procedures were conducted. Such consent triggers the delivery of blood sample collection kits to the participant and collection of the participant's medical records. Once the medical authorization form (606) is submitted, the participant encounters a medical survey (607), which aims to collect additional information regarding the participant's medical background. The enrollment process is complete upon submission of the medical survey (607). Each of the completed eligibility determination (604), electronic consent (605), medical authorization form (606), and medical survey (607) generates eligibility data (608), consent data (609), medical authorization data (610), and medical survey data (611), respectively, which are deposited in the patient or participant's registry database (612).

The eligibility determination (604) can be sent to an authentication platform (613), which is used for single-sign on user authentication, and storage of account data, e-mail address, username, and password. The information from the authentication platform is then transferred to the email services platform (614), which comprises a service for delivering automated e-mail user notification to participants (601). The information from the authentication platform is also transferred to a CureCloud Application (615), and vice versa. The CureCloud Application can be a data study management subportal that triggers shipping of the sample kits (e.g., blood kits). Similarly, information can transfer between the patient registry database (612) and the CureCloud Application (615). Information from the CureCloud Application (615) is also transferred to the email services platform (614). Additionally, the CureCloud Application (615) can manage sample kit collection (616), including managing and sending kit requests to a study management system (617). The study management system (617) releases information to one or more study staff (618) who has access through username and password authentication. The one or more study staff (618) can then transfer the study management system information to the patient or participant registry database (612).

The study management system (617) can send a blood sample request and label printing for a subportal that manages processing, testing and data generation (631). The subportal (631) also manages blood kit shipping and returns to the patient or participant (601). The data from the subportal (631) and data from external research studies (619) are pre-loaded or transferred to associated cloud file storage buckets (620). Information in the associated cloud file storage buckets (620) are transferred to dedicated workspaces (621), and vice versa. The dedicated workspaces are displayed on a user interface (622), which is accessible for viewing and analysis by a researcher (623).

Separately, the study management system (617) sends a patient or participant clinical data request to the clinical data abstraction and aggregation portal (624), which then transfers clinical data to a secure file transfer protocol (625). The data from the secure file transfer protocol (625) is sent for data analysis (626) in the visualization platform (627). The data analysis subportal (626) and existing data (e.g., medical research data or user data) in the database (628) transfers analyzed data or existing data between one another. The data analysis subportal (626) can also transfer analyzed data to the associated cloud file storage buckets (620) or the dedicated workspaces (621), and vice versa. Finally, the data analysis subportal (626) transfers analyzed data for viewing and analysis to the researcher (623) or transfers analyzed data for visualization to the physician portal (629) and/or patient or participant portal (630). The patient or participant (601) through email validation, username and password authentication can access his or her own data in the patient or participant portal (630).

A. Participant Registry a. Participants

Participants can be humans or non-human primates such as, but not limited to, chimpanzees, and other apes and monkey species; farm animals such as, but not limited to, cattle, horses, sheep, goats, swine; domestic animals such as, but not limited to, rabbits, dogs, and cats; laboratory animals including, but not limited to, rodents, such as, but not limited to, rats, mice and guinea pigs. A participant can be of any age. Participants can be, for example, male, female, elderly adults, adults, adolescents, pre-adolescents, children, toddlers, or infants.

The participant can have a pre-existing disease or condition, such as, but not limited to, cancer or a CNS condition, or none. The participant can be non-responsive to an existing or past treatment, such as, but not limited to, a treatment for cancer. The participant can be undergoing a treatment for cancer, for example, chemotherapy. A participant can have a positive, negative, or ambiguous result from a prescreening test for a health condition.

In some embodiments, a participant can have a cancerous or non-cancerous disease. In other embodiments, the patient has, or is diagnosed with a cancerous disease, such as, but not limited to, acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, bowl cancer, cancers of the blood, craniopharyngioma, ependymoblastoma, ependymoma, medulloblastoma, medulloeptithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom macroglobulinemia, Wilms Tumor and/or other tumors. A participant can have a cancerous disease, for example, multiple myeloma in the bone marrow. A participant can also have multiple myeloma in bone marrow with the most activity, such as, but not limited to, bone marrow in the spine, pelvic bones, ribs, shoulders, or hips. Multiple myeloma is characterized or can be preceded by several features, including, but not limited to: 1) low blood counts; 2) bone and calcium problems; 3) infections; 4) kidney problems; 5) monoclonal gammopathy; 6) light chain amyloidosis; 7) monoclonal gammopathy of undetermined significance; 8) solitary plasmacytomas; and 9) high levels of M protein in the blood.

In some embodiments, a participant can have a condition characterized by low blood counts. A participant can have multiple myeloma, where the overgrowth of plasma cells in the bone marrow can crowd out normal blood-forming cells, leading to low blood counts. A participant can also have a condition characterized by anemia (i.e., a shortage of red blood cells). A participant can have a condition characterized by thrombocytopenia (i.e., low levels of platelets in the blood), which can lead to increased bleeding and bruising. A participant can also have a condition characterized by leukopenia (i.e., a shortage of normal white blood cells), which can lead to problems fighting infections. In some embodiments, a participant can have multiple myeloma and exhibit high levels of M protein and light chains (Bence Jones proteins), which can crowd out normal functioning immunoglobulins or thicken the participant's blood.

In some embodiments, a participant can have a condition characterized by bone and calcium problems. A participant can have multiple myeloma, which can lead to bone loss. A participant can also have multiple myeloma, and myeloma cells can gather to form masses in the bone marrow and disrupt the normal structure of the surrounding bone. A participant can have a condition that secretes cytokines, which interfere with the normal process of bone repair and growth. A participant can also have multiple myeloma, and the cytokines secreted by myeloma cells can stimulate the development of osteoclasts (i.e., cells that dissolve the bone). In some embodiments, groups of myeloma cells can cause other cells in the bone marrow to remove the solid part of a bone and cause soft spots in a bone (i.e., osteolytic lesions). In some embodiments, myeloma cells can increase bone break-down and raise calcium levels in the blood (i.e., hypercalcemia). In some embodiments, myeloma cells can inhibit the ability of osteoblasts to develop new bone.

In some embodiments, a participant can have a condition characterized by infections. Myeloma cells can crowd out normal plasma cells and inhibit antibody formation against infections. A participant can have a condition that results in the production of antibodies that are ineffective against infections. A participant can also have a condition that produces monoclonal antibodies that are ineffective against infections. A participant can have a condition that harms a participant's kidneys. In some embodiments, a participant can have multiple myeloma, and the antibodies made by myeloma cells can lead to kidney damage. The antibodies made by myeloma cells can lead to kidney failure.

In some embodiments, the participant can have a condition, for example, multiple myeloma, that was preceded by monoclonal gammopathy (i.e., having many copies of the same antibody). The participant can have multiple myeloma that was preceded by monoclonal gammopathy of undetermined significance. A participant can be determined to have monoclonal gammopathy with a blood test.

In some embodiments, a participant can have a condition that is characterized by light chain amyloidosis (i.e., when abnormal cells make antibodies with too many light chains). Light chains can deposit in tissues and build up, leading to the formation of amyloid protein. A participant can have multiple myeloma and have buildup of amyloid in organs, which can enlarge the organs and inhibit proper functioning. In some embodiments, a participant with multiple myeloma can have amyloid build up in the heart, which can result in an irregular heart beat and cause the heart to enlarge and weaken. Consequently, a participant can have congestive heart failure, and exhibit symptoms such as, but not limited to, shortness of breath and swelling in the legs. A participant can also have amyloid buildup in the kidneys. In some embodiments, amyloid buildup in the kidneys can lead to kidney failure.

In some embodiments, a participant can have a condition, such as, but not limited to, multiple myeloma, that is characterized by solitary plasmacytomas. A solitary plasmacytoma can develop in a bone, and is called an isolated plasmacytoma of bone. A plasmacytoma that develops in other tissues is called an extramedullary plasmacytoma. In some embodiments, a plasmacytoma can develop in the lungs. A participant can have early stage multiple myeloma and be asymptomatic.

In some embodiments, a participant can have a condition, such as, but not limited to, type 1 diabetes, type 2 diabetes, cystic fibrosis, arthritis, epilepsy, heart disease, HIV/AIDS, hepatitis, or kidney disease or a precursor condition. In some embodiments, a participant can have a central nervous system condition, such as, but not limited to, Parkinson's disease or Alzheimer's disease and/or a precursor condition.

b. Participant Enrollment

The disclosure describes a patient data registry that can integrate data obtained from participants in a study of a disease or disorder. The participants can be participants of a research study, a clinical trial, or a longitudinal study. A participant enrolled in the study of a disease can be a healthy control, at risk for developing the disease, newly diagnosed with the disease, newly diagnosed with an advanced form of the disease, about to undergo treatment for the disease, currently undergoing treatment for a disease, have already been treated for the disease, or about to resume treatment for a relapse of the disease. At least one participant of the patient data registry can be a healthy control; for example, some of the participants of the patient data registry can be healthy controls. At least one participant of the patient data registry can be newly diagnosed with a disease; for example, some of the participants of the patient data registry can be newly diagnosed with a disease. In some embodiments, patients or participants who live outside the United States are excluded from enrollment. In some embodiments, patients with a diagnosis other than the disease (e.g., Multiple Myeloma) or a known or suspected precursor to the disease are excluded from enrollment. In some embodiments, women of child-bearing age are permitted into the study.

In some embodiments, the integrated, molecular, omics (included, but not limited to, genomics, proteomics, lipidomics), immunotherapy, metabolic, epigenetic, and clinical database can recruit participants directly using online consent forms and/or registration forms. A subject enrolled in a study or participating in the patient data registry can be required to provide written consent for participation in the study or the patient data registry. The written consent can include a provision to co-sign ownership of any and all samples collected, including, but not limited to, any data or products produced using the samples. In some embodiments, the written consent can include a provision to co-sign ownership of any and all samples to a sponsor or organization involved in the study. The written consent can also include a provision to authorize the release of health information pursuant to Health Insurance Portability Accountability Act (HIPAA) and General Data Protection Regulation (GDPR).

An electronic informed consent process can be used for all participants to ensure consistency and standardization of consent information. The electronic informed consent process allows for rapid scaling of consent. The electronic consent process aids in understanding core elements of the patient data registry including, but not limited to, information on the detailed nature, purpose, procedures, benefits, and risks of and alternatives to participating in the study. The elements of the patient data registry can be available via the web and/or through a native mobile platform. Participants can review the consent document and additional information materials online, and submit consent electronically through the protocol website. A patient call center staff can be available by phone to answer any questions for participants or legal guardians. Subjects, or legal guardians, who consent can sign an electronic informed consent document. The consent status of each participant can be recorded by the registration platform, and an individual's decision about participation may not affect participation in other research studies or affect the care received at any treatment or cancer care facility.

The electronic consent form guides the consenting participant, or legal guardian, through a step by step process reviewing the elements of informed consent. The elements of informed consent can include, but not limited to, introduction to the integrated, molecular, omics (e.g., genomics, proteomics, lipidomics), immunotherapy, metabolic, epigenetic, and clinical platform, reasons for conducting the study, reasons why participants are being asked to participate in the study, duration of a patient's involvement in part of the study, the number of participants in the study; detailed information regarding the study (e.g., providing blood samples and data, the data can be used and shared, benefits and risk of participating in the study, and costs); authorization for use and disclosure of health information (e.g., Health Insurance Portability and Accountability Act waiver), or contact information and completion of the consent process with an e-signature.

The written consent can include a provision to waive liability for any adverse effects experienced by the participant during the course of the study. In some embodiments, the written consent can include a provision to waive liability for adverse effects experienced by the participant, including, but not limited to, acne, high blood pressure, acute renal failure, hives, addiction, hoarseness, agranulocytosis, hyperglycemia, allergic reaction, hypoglycemia, amnesia, increased appetite, anemia, increased saliva, anxiety, infection, birth defects, inflammation, bloating, inflammatory bowel disease, blood clots, insomnia, bloody, black, or tarry stools, irregular heartbeat, blurred vision, itching, breast tenderness, jaundice, breathing and respiratory difficulties, joint pain, bruising, kidney failure, cancer, lactic acidosis, cardiovascular disease, liver failure and liver damage, change or loss in taste, loss of appetite, chest pain, loss or change in menstrual cycle, confusion, low blood pressure, conjunctivitis, lower back pain, constipation, melasma, Crohn's disease, mood swings, decreased libido, mouth sores, decreased urination, muscle pain, dehydration, nausea, dementia, nervousness, depression, pale stools, diabetes, rash, diarrhea, respiratory infection, dizziness, restlessness, drowsiness, seizures, dry eyes, sensitivity to light, dry mouth, sore throat, dystonia, stomach pain, edema, stroke, erectile dysfunction, suicide, facial tics, sweating, fatigue, swelling, fever, tardive dyskinesia, flu and cold symptoms, thirst, flushing, thrombosis, gallstones, tinnitus, glaucoma, ulcerative colitis, hair loss, vomiting, hallucinations, weight gain, headache, weight loss, heart attack, wheezing, heartburn, gas, indigestion, white patches in the mouth or throat, death, or any combination thereof.

Subjects enrolled in a study or participating in a patient data registry can be compensated for enrolling in the study or patient data registry. In some embodiments, subjects enrolled in a study or participating in a patient data registry can be compensated with money, access to experimental treatments, access to treatment methods that have limited availability, access to free or discounted treatments, free or discounted housing during the all or parts of the study, access to study results, or any combination thereof. In some embodiments, participants are not compensated for enrolling in a study or participating in a patient data registry.

Participants can be enrolled in a study at one or more enrolling sites. In some embodiments, participants can be enrolled in a study at at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200 enrolling sites, or more. In some embodiments, participants can be enrolled in a study at, for example, at most about 300, at most about 200, at most about 190, at most about 180, at most about 170, at most about 160, at most about 150, at most about 140, at most about 130, at most about 120, at most about 110, at most about 100, at most about 90, at most about 80, at most about 70, at most about 60, at most about 50, at most about 40, at most about 30, at most about 20, at most about 10 enrolling sites, or less. In some embodiments, participants can be enrolled in a study at at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 enrolling sites, or more. In some embodiments, participants can be enrolled in a study at, for example, at most about 200, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 enrolling sites, or less.

The number of enrolling sites can vary throughout the course of a study. A study can increase the number of enrolling sites as the study progresses and/or expands. The enrolling sites can include non-profit hospitals, for-profit hospitals, academic medical centers, community health centers, doctors' offices, free-care clinics, outpatient treatment facilities, inpatient treatment facilities, clinical trial sites, government agencies, government-run or government-supported medical centers (e.g., Veterans Affairs Hospitals), or any combination thereof. In some embodiments, a study includes a non-profit organization and a non-profit research organization as enrolling sites. The enrolling sites of a study are selected by a scientific advisory board, comprising of, for example, non-industry scientists and researchers.

Participants can be enrolled in a study or patient data registry for any period of time. For example, participants can be enrolled in a study or patient data registry for at least about 1 month, at least about 6 months, at least about 12 months, at least about 18 months, at least about 24 months, at least about 30 months, at least about 36 months, at least about 42 months, at least about 48 months, at least about 54 months, at least about 60 months, at least about 66 months, at least about 72 months, at least about 80 months, at least about 86 months, at least about 92 months, at least about 98 months, or more. participants can be enrolled in a study or patient data registry for at most about 100 months, at most about 98 months, at most about 92 months, at most about 86 months, at most about 80 months, at most about 72 months, at most about 66 months, at most about 60 months, at most about 54 months, at most about 48 months, at most about 42 months, at most about 36 months, at most about 30 months, at most about 24 months, at most about 18 months, at most about 12 months, at most about 6 months, at most about 1 month, or less. In some embodiments, participants can be enrolled in a study or patient data registry for at least about 1 year, at least about 2 years, at least about 4 years, at least about 6 years, at least about 8 years, at least about 10 years, at least about 12 years, at least about 14 years, at least about 16 years, at least about 18 years, at least about 20 years, at least about 22 years, at least about 24 years, at least about 26 years, at least about 28 years, at least about 30 years, or more. In some embodiments, participants can be enrolled in a study or patient data registry for at most about 50 years, at most about 40 years, at most about 30 years, at most about 28 years, at most about 26 years, at most about 24 years, at most about 22 years, at most about 20 years, at most about 18 years, at most about 16 years, at most about 14 years, at most about 12 years, at most about 10 years, at most about 8 years, at most about 6 years, at most about 4 years, at most about 2 years, at most about 1 year, or less. Participants can also be enrolled in a study or patient data registry for the duration of the participants' lives.

A study or patient data registry of the disclosure can enroll multiple participants. The number of participants enrolled in a study or patient data registry can be, for example, at least about 25, at least about 50, at least about 75, at least about 100, at least about 125, at least about 150, at least about 175, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, at least about 1000 participants, or more. The number of participants enrolled in a study or patient data registry can be, for example, at most about 2000, at most about 1000, at most about 950, at most about 900, at most about 850, at most about 800, at most about 750, at most about 700, at most about 650, at most about 600, at most about 550, at most about 500, at most about 450, at most about 400, at most about 350, at most about 300, at most about 250, at most about 200, at most about 175, at most about 150, at most about 125, at most about 100, at most about 75, at most about 50, at most about 25 participants, or less. The number of participants enrolled in a study or patient data registry can also be, for example, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 19000, at least about 20000, at least about 21000, at least about 22000, at least about 23000, at least about 24000, at least about 25000, at least about 26000, at least about 27000, at least about 28000, at least about 29000, at least about 30000 participants, or more. The number of participants enrolled in a study or patient data registry can also be, for example, at most about 40000, at most about 30000, at most about 29000, at most about 28000, at most about 27000, at most about 26000, at most about 25000, at most about 24000, at most about 23000, at most about 22000, at most about 21000, at most about 20000, at most about 19000, at most about 18,000, at most about 17000, at most about 16000, at most about 15000, at most about 14000, at most about 13000, at most about 12000, at most about 11000, at most about 10000, at most about 9000, at most about 8000, at most about 7000, at most about 6000, at most about 5000, at most about 4000, at most about 3000, at most about 2000, at most about 1000 participants, or less. In some embodiments, 500 participants are enrolled in a study or patient data registry. In some embodiments, 5000 participants are enrolled in a study or patient data registry. In some embodiments, 10000 participants are enrolled in a study or patient data registry. In some embodiments, 20000 participants are enrolled in a study or patient data registry.

A consent form can be used to gather information about a participant. A consent form can be a paper form or an online form. Information collected by the consent form can include, for example, the participant's race, ethnic group, sex, health history, contact information, current mailing address, name and contact information of the participant's physician, and the names of hospitals and/or institutions where the participant has had any procedures or treatment (e.g., hospital stay, bone marrow aspirates, positron emission tomography scans, and magnetic resonance imaging). The consent form can inform the participant that the data and blood samples are used immediately for research, or stored for future research purposes. The consent form can also inform the participant that any collected data are de-identified (i.e., removal of identifying information) and shared with other researchers. The consent form can also include information on whether the participant has been diagnosed with a specific disease, for example, metastatic and/or advanced prostate cancer.

After a participant is registered, and a participant has submitted a consent form, a kit and instructions for visiting a lab close to the participant can be mailed to the participant. The lab can then take blood from a vein, for example, up to 40 mL of blood can be withdrawn from a participant. A participant can be asked to submit an additional sample of blood, for example, if the participant's condition changes.

A participant's doctors and hospitals can be contacted to obtain past, current, and future copies of the participant's medical records to complete a participant profile. A participant's medical records can be used to link a participant's disease biology and molecular characterizations with the manner the condition is clinically presented.

Once the medical authorization form is submitted to complete the consenting process, the participant completes a medical survey to initiate the collection process of the participant's clinical information. Through a set of questions, the participant is asked to provide answers about demographics (e.g., gender, ethnicity, and age), medical history (e.g., diagnosis, treatment, family history of cancer) and disease subtype (as characterized by the presence of genetic alterations frequently observed in diseases, such as multiple myeloma). The information provided by the participant can be used when cross-referencing with the data retrieved from the EMRs.

In some embodiments, the medical survey can comprise at least about 3, at least about 5, at least about 7, at least about 8, at least about 9, at least about 10, at least about 11, at least about 12, at least about 13, at least about 14, at least about 15, at least about 16, at least about 17, at least about 18, at least about 19, at least about 20, at least about 25, at least about 30, at least about 35, at least about 40, at least about 45, at least about 50, at least about 60, at least about 70, at least about 80, at least about 90, at least about 100, at least about 200 questions, or more.

In some embodiments, the medical survey can comprise at most about 200, at most about 100, at most about 90, at most about 80, at most about 70, at most about 60, at most about 50, at most about 45, at most about 40, at most about 35, at most about 30, at most about 25, at most about 20, at most about 19, at most about 18, at most about 17, at most about 16, at most about 15, at most about 14, at most about 13, at most about 12, at most about 11, at most about 10, at most about 9, at most about 8, at most about 7, at most about 5, at most about 3 questions, or less. In some embodiments, the medical survey can comprise 12 questions.

In some embodiments, external capabilities or services are embedded in the patient registration portal. The external capabilities or services include, but are not limited to, services for single-sign on user authentication, and storage of account data, e-mail address, username, and password; services to manage sample kit collection (e.g., managing kit requests, label printing, and kit shipping and returns); services for storage, view, and downloading of collected participant eligibility, consent, and survey data; services for delivering automated e-mail user notification to participants; or services for shipping address validation and generation of shipping labels.

In some embodiments, all traffic via the integrated, molecular, omics (e.g., genomics, proteomics, lipidomics), immunotherapy, metabolic, epigenetic, and clinical database is encrypted using secure sockets layer. The database application can be hosted on cloud services (e.g., Google's Cloud Services). A participant can have an e-mail address validated, and is authenticated with a username and password to access the enrollment process and the participant's data. In some embodiments, study staff access to the services to manage sample kit collection and services for storage, view, and downloading requires username and password authentication.

In some embodiments, a patient support center employs staff (e.g., registered nurses (RNs)) who are professionally trained and who serve as a key resource to answer participant and caregiver questions relating to participation in the study. The RNs can also respond to inquiries related to the disease, treatments, clinical trial searches, clinician referrals, access to treatments (e.g., financial), and other supportive services. The patient support center can offer one-on-one support service to patients by providing resources and education for optimal disease management. The patient support center can contact patients to discuss and collect information related to participation in the integrated, molecular, omics (e.g., genomics, proteomics, lipidomics), immunotherapy, metabolic, epigenetic, and clinical database. The information collected by the patient support center is documented and maintained in a secure database and shared. Information in the database is used to assist in delivering the patient support services.

c. Data Entry i. Basic Biological Data

The integrated, molecular, omics (included, but not limited to, genomics, proteomics, lipidomics), immunotherapy, metabolic, epigenetic, and clinical database can include, but is not limited to, patient name, patient universally unique identifier, basic biological data, gender, age, date of birth, weight, race, ethnicity, smoking history, participant medical history (e.g., cancer site, past cancer diagnosis, relevant comorbidities), family medical history, list of medications, institution, or water intake. The integrated, molecular, omics (included, but not limited to, genomics, proteomics, lipidomics), immunotherapy, metabolic, epigenetic, and clinical database can also include, but is not limited to, date of diagnosis, stage of diagnosis based on the international staging system, stage of diagnosis based on the revised international staging system, stage of diagnosis based on the Durie-Salmon staging system, pathology data (e.g., date), flow cytometry data (e.g., percent of plasma cell neoplasm, such as, but not limited to, in the bone marrow), immuno-histochemistry data (e.g., percent of plasma cell neoplasm, such as, but not limited to, in the bone marrow, CD56 expression), subtype data (e.g. type of heavy chain or type of light chain), gene expression profile, recurrence data (e.g., date), molecular pathology test data (e.g., date), molecular pathology lab data, fluorescence in situ hybridization data (e.g., del13, del17p13, t(4;14), t(11;14), t(14;16), t(14;20), 1q21 amplification, 1p abnormality), cytogenetics data, plasmacytoma evaluation (e.g., yes or no in regards to soft tissue or bone), bone marrow data (e.g., aspirate, biopsy), radiographic evaluation type (e.g., skeletal survey, bone scan, positron emission tomography-computed tomography), serum quantitative immunoglobins data (e.g., IgG, IgA, IgM, IgD, IgE), serum protein electrophoresis, urine protein electrophoresis (e.g. 24 hour urine, random urine), urine immunofixation electrophoresis data, free light-chain assay data, complete blood count test results data (e.g., white blood cell, absolute neutrophil count, platelets), chemistry panel data (e.g., lactate dehydrogenase, beta-2 microglobin, creatine, albumin, calcium, creatine clearance, blood urea nitrogen, bilirubin, aspartate aminotransferase, alanine aminotransferase, uric acid, serum total protein), radiographic evaluation data e.g., number of lesions), basic metabolic panel (BMP) data (e.g., glucose, calcium, sodium, potassium, carbon dioxide, chloride, blood urea nitrogen, and creatinine levels), or complete blood count (CBC) data (e.g., white blood cells, red blood cells, hemoglobin, hematocrit, mean corpuscular volume, and platelet levels). Further, the integrated, molecular, omics (included, but not limited to, genomics, proteomics, lipidomics), immunotherapy, metabolic, epigenetic, and clinical database can include, but is not limited to, data obtained from participant and caregiver questionnaires, tracking for medical records requests, and wearable/sensor data import data. In some embodiments, the integrated, molecular, omics (included, but not limited to, genomics, proteomics, lipidomics), immunotherapy, metabolic, epigenetic, and clinical database includes, but is not limited to, data extracted from electronical medical records and/or wearable/sensor applications. The integrated, molecular, omics (including, but not limited to, genomics, proteomics, lipidomics), immunotherapy, metabolic, epigenetic, and clinical database can also include, but is not limited to, drug name, regimen type (e.g., induction, consolidation, maintenance, salvage, conditioning, and mobilization), drug dosage (e.g. units), drug regimen data (e.g., start date, end date), surgery data (e.g., date, type), radiation data (e.g., start date, end date, delivered dosage amount, treatment modality, site), or transplant data (e.g., date, type). In some embodiments, the integrated, molecular, omics (including, but not limited to, genomics, proteomics, lipidomics), immunotherapy, metabolic, epigenetic, and clinical database includes, but is not limited to, therapy outcome data (e.g., date), response to each therapy (e.g. referencing international myeloma working group), minimal residual disease status, response not attributed to a specific therapy, adverse event to a therapy, date of presentation (e.g., of an adverse event), data on whether an adverse event results in a treatment change (e.g. yes or no), last follow up data (e.g. date, disease status), or death data (e.g. date). The integrated, molecular, omics (including, but not limited to, genomics, proteomics, lipidomics), immunotherapy, metabolic, epigenetic, and clinical database can also include, but is not limited to, performance status (e.g., date, eastern cooperative oncology group, karnofsky, score).

ii. Biological Samples

Understanding the relationships between circulating genetic and immune biomarkers as related to disease initiation, progression and response to therapy is achieved through the collection of samples that allow the broadest range of assays.

Biological samples can be obtained from a participant that is enrolled in a study. In some embodiments, peripheral blood samples are collected with annotated clinical data from patients or participants with a disease (e.g., Multiple Myeloma) or a pre-disease condition (e.g., smoldering multiple myeloma). In some embodiments, biological samples can be obtained from a participant prior to treatment, during treatment, post treatment, after relapse, or post-mortem. Samples can be obtained from a participant any number of times throughout the study. Samples can be obtained from a participant enrolled in a study, for example, at least about 1, at least about 5, at least about 10, at least about 15, at least about 20, at least about 25, at least about 30, at least about 35, at least about 40, at least about 45, at least about 50 times, or more. More than one sample can be obtained from a participant at any given time. Samples can be obtained from a participant enrolled in a study, for example, at most about 50, at most about 45, at most about 40, at most about 35, at most about 30, at most about 25, at most about 20, at most about 15, at most about 10, at most about 5, at most about 4, at most about 3, at most about 2 times, or less. In some embodiments, at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20 samples, or more can be obtained from a participant at a given time. In other embodiments, at most about 25, at most about 24, at most about 23, at most about 22, at most about 21, at most about 20, at most about 19, at most about 18, at most about 17, at most about 16, at most about 15, at most about 14, at most about 13, at most about 12, at most about 11, at most about 10, at most about 9, at most about 8, at most about 7, at most about 6, at most about 5, at most about 4, at most about 3, at most about 2 samples, or less. In some embodiments, participants provide blood for the sample collection. In some embodiments, participants provide at least about 1 mL, at least about 3 mL, at least about 5 mL, at least about 10 mL, at least about 15 mL, at least about 20 mL, at least about 25 mL, at least about 30 mL, at least about 35 mL, at least about 36 mL, at least about 37 mL, at least about 38 mL, at least about 39 mL, at least about 40 mL, at least about 41 mL, at least about 42 mL, at least about 43 mL, at least about 44 mL, at least about 45 mL, at least about 50 mL, at least about 55 mL, at least about 60 mL, at least about 70 mL, at least about 80 mL, at least about 90 mL, at least about 100 mL, at least about 200 mL of blood, or more.

In some embodiments, participants can provide at most about 200 mL, at most about 100 mL, at most about 90 mL, at most about 80 mL, at most about 70 mL, at most about 60 mL, at most about 55 mL, at most about 50 mL, at most about 45 mL, at most about 44 mL, at most about 43 mL, at most about 42 mL, at most about 41 mL, at most about 40 mL, at most about 39 mL, at most about 38 mL, at most about 37 mL, at most about 36 mL, at most about 35 mL, at most about 30 mL, at most about 25 mL, at most about 20 mL, at most about 15 mL, at most about 10 mL, at most about 5 mL, at most about 3 mL, at most about 1 mL of blood, or less. In some embodiments, participants can provide at most about 40 mL of blood for the sample collection.

The total volume of collection is determined by the protocol and/or the laboratory test(s) to be performed by the team collecting the samples and can be gauged by the subject's tolerance. Peripheral blood can be collected from patients who consent to the protocol. The samples can be obtained at a time scheduled by the participant with the phlebotomy service provider, and/or collected at the participant's home. The patient peripheral blood samples can be obtained at diagnosis or at any time in follow up.

Biological samples can include, for example, fluid and/or tissue from a subject. The biological sample can include, for example, a tumor biological sample or a normal biological sample. The control can be obtained from the participant. The control can be a healthy control or normal biological sample. Biological samples obtained from participants can include blood (e.g., whole blood), serum, fluid (e.g., saliva), and tissue samples or materials derived from blood, serum, fluid, or tissue samples. In some embodiments, samples obtained from blood, serum, fluid, and tissue samples can include polypeptides, polypeptide sequences, polynucleotides, polynucleotide sequences, genes, gene fragments, gene sequences, proteins, protein fragments, protein sequences, probes, DNA, RNA, cDNA libraries, plasmids, vectors, expression systems, cells, cell lines, organisms, histology slides, and antibodies or other biological substances. Biological samples can include any constituents, progeny, mutants, variants, unmodified derivatives, replications, reagents, or chemical compounds derived from blood, serum, fluid, or tissue samples.

A biological fluid or tissue sample can be obtained from a participant's tumor, diseased tissue, healthy tissue, blood, bile, saliva, or any combination thereof. A fluid sample can also be a semen sample, tear sample, urine sample, spinal fluid sample, mucus sample, amniotic fluid sample, vaginal secretion, or any combination thereof. Further, a biological sample obtained from a participant can include a breath sample, hair sample, stool sample, or any combination thereof.

The biological sample can comprise plasma, a buffy coat, or saliva. The buffy coat can comprise lymphocytes, thrombocytes, and leukocytes. A tumor sample can include a tumor tissue biopsy and/or circulating tumor DNA in a cell-free DNA sample. The normal sample can include buffy coat cells, whole blood, or normal epithelial cells. Buffy coat cells can be white blood cells. The normal sample can include nucleic acid molecules derived from the white blood cells or epithelial cells in the saliva. Normal DNA can be extracted from the white blood cells or epithelial cells in the saliva. The biological sample can comprise nucleic acids from different sources. For example, the biological sample can comprise germline DNA or somatic DNA. The biological sample can comprise nucleic acids carrying mutations. For example, the biological sample can comprise DNA carrying germline mutations and/or somatic mutations. The biological sample can also comprise DNA carrying cancer-associated mutations (e.g., cancer-associated somatic mutations). Tumor and normal cells can be compared. The tumor sample can be compared to the various normal samples. A sample can comprise RNA (e.g., mRNA), which can be sequenced (e.g., via reverse transcription of RNA and subsequent sequencing of cDNA).

A tissue sample can be obtained from a participant by conducting a biopsy. For example, a tissue sample can be obtained from a participant by an incisional biopsy, a core biopsy, a needle aspiration biopsy, or a bone marrow biopsy. In some embodiments, a bone marrow biopsy can be a trephine biopsy or a bone marrow aspiration biopsy. A biopsy can also be a gastrointestinal tract biopsy, for example, an esophageal, stomach, duodenum, jejunum ileum, cecum, colon, or rectum biopsy. In some embodiments, a gastrointestinal tract biopsy can performed with a flexible endoscope. In some embodiments, a needle core biopsy or aspirate biopsy of the pancreas can be performed through the stomach or duodenum.

A tissue is a group of connected specialized cells that perform a special function. The tissue can be an extracellular matrix material. The tissue analyzed can be a portion of a tissue to be transplanted or surgically grafted, such as an organ (e.g., heart, kidney, liver, lung), skin, bone, nervous tissue, tendons, blood vessels, fat, cornea, blood, or a blood component.

Examples of tissue include, but are not limited to, placental tissue, mammary gland tissue, gastrointestinal tissue, liver tissue, kidney tissue, musculoskeletal tissue, genitourinary tissue, bone marrow tissue, prostate tissue, skin tissue, nasal passage tissue, neural tissue, eye tissue, and central nervous system tissue. The tissue can originate from a human and or mammal. The tissue can comprise the connecting material and the liquid material found in association with the cells and/or tissues. A tissue can also include biopsied tissue and media containing cells or biological material. The biological sample can be a tumor tissue sample.

Tissue from a subject can be preserved for research that involves maintaining molecule and morphological integrity. The preservation methods of tissue for latter downstream usage can include freezing media embedded tissue, flash freezing tissue, and formalin-fixed paraffin embedded (formalin-fixed paraffin embedded (FFPE) tissue). The preservation method can also include blood sample collection, transport, and storage in a direct draw whole blood collection tube. The collection tube can stabilize cell-free DNA and can preserve cellular genomic DNA found in nucleated blood cells and circulating epithelial cells in whole blood. Blood can stabilize nucleated blood cells through the use of a preservative that prevents the release of genomic DNA to allow isolation of high-quality cell-free DNA.

The tumor biological sample can be a FFPE tissue sample. Paraformaldehyde can be used for tissue fixation. The tissue can be sliced or used as a whole. Prior to sectioning, the tissue can be embedded in cryomedia or paraffin wax. A microtome or a cryostat can be used to section the tissue. The sections can be mounted onto slides, dehydrated with alcohol washes and cleared with a detergent. The detergent can include, for example, xylene or citrisolv. For FFPE tissues, antigen retrieval can occur by thermal pre-treatment or protease pre-treatment of the sections.

Biological samples collected from a participant can comprise a blood sample or a bone marrow sample, for example, a bone marrow aspirate. One or more biological samples can be collected from the participant prior to the beginning of a course of treatment. The biological samples can be treated with a chemical agent to preserve the sample, such as, but not limited to, with an anticoagulant, including, but not limited to, ethylenediaminetetraacetic acid (EDTA), heparin, low molecular weight heparin, sodium citrate, acid citrate dextrose solution (ACD), or oxalate.

The biological fluid can include any untreated or treated fluid associated with living organisms. Examples can include, but are not limited to, blood, including whole blood, warm or cold blood, and stored or fresh blood; treated blood, such as blood diluted with at least one physiological solution, including but not limited to saline, nutrient and/or anticoagulant solutions; blood components, such as platelet concentrate (PC), platelet-rich plasma (PRP), platelet-poor plasma (PPP), platelet-free plasma, plasma (e.g., plasma isolates), fresh frozen plasma (FFP), components obtained from plasma, packed red cells (PRC), transition zone material or buffy coat (BC); analogous blood products derived from blood or a blood component or derived from bone marrow; red cells separated from plasma and resuspended in physiological fluid or a cryoprotective fluid; platelets separated from plasma and resuspended in physiological fluid or a cryoprotective fluid; isolated myeloma cells, isolated non-myeloma bone marrow cells, isolated peripheral blood mononuclear cells, bone marrow mononuclear cells, isolated immune cell populations and subtypes (B-lymphocytes (B-cells), T-lymphocytes (T-cells), Dendritic cells (DCs), Natural Killer (NK) cells, or myeloid-derived suppressor cells (MDSC). Other non-limiting examples of biological samples include serum, serum isolates, skin, heart, lung, kidney, bone marrow (e.g., bone marrow aspirates), breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, micropiota, meconium, breast milk, and/or other excretions or body tissues.

Tissue slides, inert membranes, or matrices (e.g., plastic, nitrocellulose, polyvinylidene fluoride) containing a fixed or immobilized biological sample can be subjected to analysis.

The biological sample can be a tumor sample, which can be obtained from a patient by various approaches, including, but not limited to, venipuncture, excretion, massage, biopsy, needle aspirate, lavage, scraping, surgical incision, or intervention or other approaches. The tumor sample can be a tumor tissue sample.

Cells and other biocomponents in a biological sample can be analyzed using antibodies (e.g., immunohistochemistry, western blot, enzyme linked immunosorbent assay (ELISA), mass spectrometry, antibody staining, radioimmunoassay, fluoroimmunoassay, chemiluminescence immunoassay, and liposome immunoassay). Primary cells can be isolated from small fragments of tissue and purified from the blood. The primary cells can include lymphocytes (white blood cells), fibroblasts (skin biopsy cells), or epithelial cells. The biological sample can be a single cell. Before antibody staining, endogenous biotin or enzymes can be quenched. Biological samples can be incubated with buffer for blockage of reactive sites in which primary or secondary antibodies can bind to reduce non-specific binding between the antibodies and non-specific proteins resulting in background staining. Blocking buffers include, but are not limited to, non-fat dry milk, normal serum, gelatin, and bovine serum albumin. Background staining can be reduced by methods including, but not limited to, dilution of primary or secondary antibodies, use of different detection system or a different primary antibody, and alteration of the time or temperature of the incubation. Tissue known to express the antigen and tissue not known to express the antigen can be used as a control.

The biological sample can comprise nucleic acid molecules from different sources. For example, a sample can comprise germline DNA or somatic DNA. A sample can comprise nucleic acids carrying mutations. For example, a sample can comprise DNA carrying germline mutations and/or somatic mutations. A sample can also comprise DNA carrying cancer-associated mutations (e.g., cancer-associated somatic mutations).

A sample can comprise various amounts of nucleic acid that contains genome equivalents. For example, a sample of about 30 ng DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cell-free DNA (cfDNA), about 600 billion individual molecules.

The biological sample obtainable from specimens or fluids can include, but are not limited to, detached tumor cells or free nucleic acids that are released from dead or damaged tumor cells. Nucleic acids can include, but are not limited to, deoxyribonucleic acid (DNA), cell free-deoxyribonucleic acid (cfDNA) molecules, cellular deoxyribose nucleic acid (cDNA) molecules, ribonucleic acid (RNA) molecules, genomic DNA molecules, mitochondrial DNA molecules, single or double stranded DNA molecules, or protein-associated nucleic acids. Any nucleic acid specimen in purified or non-purified form obtained from a specimen cell can be utilized as the starting nucleic acid or acids. The cfDNA molecules, cDNA molecules, and RNA molecules can be assayed for presence or absence of biological markers.

The biological samples can generate biological data. The biological data can comprise data from biological sample components including, but not limited to, protein, peptides, cell-free nucleic acids, ribonucleic acids, deoxyribose nucleic acids, or any combination thereof.

The biomolecules can be normal and abnormal. The normal biomolecules can be isolated from the buffy coat of the biological sample. The abnormal biomolecules can be isolated from the plasma or a tumor tissue of the biological sample.

The biological sample of components can be analyzed with respect to various biomarkers. Biomarkers can be indicators of or a proxy for various biological phenomena. The presence or absence of a biological marker, a quantity or quality thereof can be indicative of a biological phenomena. Biomarkers (biological markers) can be a characteristic that is objectively measured and determined as an indicator of normal biological processes, pathogenic processes, pharmacologic responses to a therapeutic intervention, or environmental exposure. Biomarkers can be categorized into DNA biomarkers, DNA tumor biomarkers, and general biomarkers. Biomarkers include, but are not limited to, cancer biomarker, clinical endpoint, companion endpoint, copy number variant (CNV) biomarker, diagnostic biomarker, disease biomarker, DNA biomarker efficacy biomarker, epigenetic biomarker, monitoring biomarker, prognostic biomarker, predictive biomarker, safety biomarker, screening biomarker, staging biomarker, stratification biomarker, surrogate biomarker, target biomarker, target biomarker, or toxicity biomarker. Diagnostic biomarkers can be used to diagnose a disease or decide on the severity of a disease. DNA biomarkers can be an interleukin or solute carrier organic anion transporter family member.

d. Methods of Obtaining Biological Samples and Biomolecules

The sample collection kits can include, but are not limited to, cfDNA blood collection tube(s) and blood collection tube(s) that stabilize nucleated blood cells through the use of a preservative that prevents the release of genomic DNA, allowing isolation of high-quality cfDNA. For immune analyses, a Liquid Biopsy kit can be include, but is not limited to, Vacutainer EDTA purple top tubes.

In some embodiments, the sample collection kits or liquid biopsy kit can comprise at least about 1, at least about 2, at least about 3, at least about 4, at least about 5, at least about 6, at least about 7, at least about 8, at least about 9, at least about 10, at least about 15, at least about 20, at least about 25, at least about 30, at least about 40, at least about 50, at least about 100 collection tubes, or more.

In some embodiments, the sample collection kits or liquid biopsy kit can comprise at most about 100, at most about 50, at most about 40, at most about 30, at most about 25, at most about 20, at most about 15, at most about 10, at most about 9, at most about 8, at most about 7, at most about 6, at most about 5, at most about 4, at most about 3, at most about 2 blood collection tubes, at most about 1 collection tube, or less.

In some embodiments, the collection tube or purple top tube can comprise a volume size at least about 1, at least about 2, at least about 3, at least about 4, at least about 5, at least about 6, at least about 7, at least about 7, at least about 8, at least about 9, at least about 10, at least about 11, at least about 12, at least about 13, at least about 14, at least about 15, at least about 16, at least about 17, at least about 18, at least about 19, at least about 20, at least about 30, at least about 40, at least about 50, at least about 60, at least about 70, at least about 80, at least about 90, at least about 100 mL, or more.

In some embodiments, the collection tube or purple top tube can comprise a volume size at most about 50, at most about 40, at most about 30, at most about 20, at most about 19, at most about 18, at most about 17, at most about 16, at most about 15, at most about 14, at most about 13, at most about 12, at most about 11, at most about 10, at most about 9, at most about 8, at most about 7, at most about 6, at most about 5, at most about 4, at most about 3, at most about 2, at most about 1 mL, or less.

In some embodiments, the sample collection kit can comprise one 9 mL cfDNA blood collection tube and a blood collection tube which stabilizes nucleated blood cells through the use of a preservative that prevents the release of genomic DNA to allow isolation of high-quality cfDNA.

In some embodiments, a liquid biopsy kit can include three 10 ml Vacutainer EDTA purple top tubes.

The collection kit can further include, but is not limited to, an absorbent sleeve, silver insulated bag, biohazard bag, room temperature gel pack, return shipper box, or fedex clinical pack. Samples can be packaged for shipment as per Standard Operating Procedures (SOP). The SOPs can be reviewed with the appropriate personnel upon receipt of regulatory approval and copies of the relevant policies can be provided. The specimens can be shipped at least about the day of collection, at least about one day after collection, at least about two days after collection, at least about three days after collection, at least about four days after collection, at least about five days after collection, at least about six days after collection, at least about seven days after collection, at least about eight days after collection, at least about nine days after collection, at least about ten days after collection, at least about two weeks after collection, at least about three weeks after collection, at least about four weeks after collection, or more.

The specimens can be shipped at most about four weeks after collection, at most about three weeks after collection, at most about two weeks after collection, at most about ten days after collection, at most about nine days after collection, at most about eight days after collection, at most about seven days after collection, at most about six days after collection, at most about five days after collection, at most about four days after collection, at most about three days after collection, at most about two days after collection, at most about 1 day after collection, or less.

The initial sample handling can be performed per the SOPs followed by a shipping protocol that maintains the chain of custody. In some embodiments, long term storage and future access to biospecimens is possible. Residual material remaining following analysis can be shipped and stored at a tissue bank. Samples can be stored indefinitely unless a participant withdraws from the study. The tissue bank can comprise a disaster recovery plan. In some embodiments, a committee can evaluate and approve procedures and requirements for distributing specimens to researchers.

The biospecimens can be given a specimen identification number that is linked to the patient's unique identification number. This process can connect specimens to clinical data, and protect confidentiality. Correlating information accompanying the shipments and the biospecimens can be collected and stored for future research. Such a collection and storage can aid translational research in the correlation of basic research findings and clinical outcomes. Patients can have specimens drawn home. The collection service can perform minimal sample processing. The Liquid Biopsy kit can be processed as described in the SOPs. Information on all aliquots, including, but not limited to, the volume for each aliquot, can be recorded in the laboratory information management system and linked to an identification number. Similarly, the immune analysis kit can be processed using the SOPs and derivatives can be tracked. In some embodiments, processed blood samples can be stored in a robotically controlled freezer. Whole blood samples can be stored in vapor phase liquid nitrogen units.

The biological sample can comprise normal biomolecules and abnormal biomolecules extracted from a subject. DNA extraction can be obtained from samples including, but not limited to, buccal swabs, hair sample, urine sample, blood sample, or a tissue sample. Cells and tissues can be obtained from a biopsy. Biopsy methods can include, but not limited to, advanced breast biopsy instrumentation, brush biopsy, computed tomography, cone biopsy, core biopsy, Crosby capsule, curettings, ductal lavage, endoscopic biopsy, endoscopic retrograde cholangiopancreatography, evacuation, excision biopsy, fine needle aspiration, fluoroscopy, frozen section, imprint, incision biopsy, liquid based cytology, loop electrosurgical excision procedure, magnetic resonance imaging, mammography, needle biopsy, positron emission tomography with fluorodeoxy-glucose, punch biopsy, sentinel node biopsy, shave biopsy, smears, stereotactic biopsy, transurethral resection, trephine (bone marrow) biopsy, ultrasound, vacuum-assisted biopsies, and wire localization biopsy.

After blood sample withdrawal from a patient and centrifugation, white blood cells can be isolated from the blood sample. The white blood cells can be divided into diseased cells and control cells.

In some embodiments, trained professionals can visit participants at home to perform screenings and tests, including, but not limited to, blood draws. Standard operating procedures and kits can be developed for the collection, initial processing, and transfer of the biospecimens to the appropriate labs.

In some embodiments, a subject can collect personal biological samples. The biological sample can be collected at home and transported to the medical center or facility. The biological sample can be collected at a medical center, for example, at a doctor's office, clinic, laboratory, patient service center, or hospital. Methods of collection can include, but are not limited to, patient's release of sputum through cough, collection of stool, urination, saliva swab, collection of saliva and oral mucosal transudate combination from the mouth, or sweat collection by a sweat simulation procedure.

Assaying can begin after a user obtains the biological sample. Assaying can comprise nucleic acid extraction from the biological sample. Nucleic acids can be extracted from a biological sample using various techniques. During nucleic acid extraction, cells can be disrupted to expose the nucleic acid by grinding or sonicating. Detergent and surfactants can be added during cell lysis to remove the membrane lipids. Protease can be used to remove proteins. Also, RNase can be added to remove RNA. Nucleic acids can also be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation (e.g., using a phenol/chloroform organic reagent), with or without the use of an automated nucleic acid extractor; (2) stationary phase adsorption methods; and (3) salt-induced nucleic acid precipitation methods, such precipitation methods being typically referred to as "salting-out" methods. Another example of nucleic acid isolation and/or purification includes the use of magnetic particles (e.g., beads) to which nucleic acids can specifically or non-specifically bind, followed by isolation of the particles using a magnet, and washing and eluting the nucleic acids from the particles. The above isolation methods can be preceded by an enzyme digestion step to help eliminate unwanted protein from the sample (e.g., digestion with proteinase K, or other like proteases). RNase inhibitors can be added to the lysis buffer. For certain cell or sample types, a protein is added in a denaturation/digestion step. Purification methods can be directed to isolate DNA, RNA (e.g., mRNA, rRNA, tRNA), or both. When both DNA and RNA are isolated together during or subsequent to an extraction procedure, further steps can be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after subsequent manipulation, such as to remove excess or unwanted reagents, reactants, or products.

In some embodiments, participants have the option to withdraw from the program. Participants can request to destroy personal stored derivatives of biospecimens. The procedure can include the following elements. Notice can be provided that a patient has not consented, changed consent or requested to be removed from the study. Upon notification, a written verification can be requested. Destruction of a sample during tissue processing includes, but not limited to, disposing of the sample in the biohazard waste bin; documentation of the sample destruction as a variance to protocol; destruction of the sample stored in the tissue bank; electronic transfer of sample destruction; obtaining and removing of the sample from the freezer; completion of the sample destruction form and placement into the appropriate study folder; recordation of the removal and destruction of the sample(s) in various locations (e.g., tissue tracking system, the study folder associated with the destroyed sample, the master list by striking a line through all destroyed samples, the master schedule list by highlighting in blue and addition of a strike through); destruction of the sample according to the request; and/or placement of the sample in a proper biohazard waste receptacle in lab. In some embodiments, tissues stored in trizol are viable indefinitely when stored at a controlled temperature.

In some embodiments, samples can be stored at at least about −196° C., at least about −100° C., at least about −90° C., at least about −85° C., at least about −80° C., at least about −75° C., at least about −70° C., at least about −65° C., at least about −60° C., at least about −50° C., at least about −40° C., at least about −30° C., at least about −25° C., at least about −20° C., at least about −15° C., at least about −10° C., at least about −5° C., at least about 0° C., at least about 4° C., at least about 8° C., or at a higher temperature.

In some embodiments, samples can be stored at at most about 8° C., at most about 4° C., at most about 0° C., at most about −5° C., at most about −10° C., at most about −15° C., at most about −20° C., at most about −25° C., at most about −30° C., at most about −40° C., at most about −50° C., at most about −60° C., at most about −65° C., at most about −70° C., at most about −75° C., at most about −80° C., at most about −85° C., at most about −90° C., at most about −100° C., at most about −196° C., or at a lower temperature.

In some embodiments, samples can be stored at a temperature of −70° C. or lower.

In some embodiments, cells stored in trizol can expire after a time period at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 18, at least about 24, at least about 30, at least about 36, at least about 48, at least about 60, at least about 72, at least about 84, at least about 96, at least about 108, at least about 120 months, or longer.

In some embodiments, cells stored in trizol can expire after a time period at most about 120, at most about 108, at most about 96, at most about 84, at most about 72, at most about 60, at most about 48, at most about 36, at most about 30, at most about 24, at most about 18, at most about 15, at most about 14, at most about 13, at most about 12, at most about 11, at most about 10, at most about 9, at most about 8, at most about 7, at most about 6, at most about 5, at most about 4, at most about 3, at most about 2, at most about 1 month, or less.

In some embodiments, cells stored in trizol can expire after a time period of one year.

In some embodiments, samples can produce good quality RNA, DNA, and protein after storage for a time period at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 18, at least about 24, at least about 30, at least about 36, at least about 48, at least about 60, at least about 72, at least about 84, at least about 96, at least about 108, at least about 120 months, or longer.

In some embodiments, samples can produce good quality RNA, DNA, and protein after storage for a time period at most about 120, at most about 108, at most about 96, at most about 84, at most about 72, at most about 60, at most about 48, at most about 36, at most about 30, at most about 24, at most about 18, at most about 15, at most about 14, at most about 13, at most about 12, at most about 11, at most about 10, at most about 9, at most about 8, at most about 7, at most about 6, at most about 5, at most about 4, at most about 3, at most about 2, at most about 1 month, or less.

In some embodiments, samples can produce good quality RNA, DNA, and protein after storage for two years.

In some embodiments, samples are not automatically be destroyed. RNA, DNA, and protein are isolated from the samples, according to SOPs. If quality assessments indicate significant degradation of the respective sample types, the samples can be removed and/or destroyed.

e. Sample Analysis and Profile Generation

The balance of pro-inflammatory and anti-inflammatory signals in tissues is mediated by: 1) the types and abundance of immune cells; 2) the presence of cell surface bound factors expressed on immune and non-immune cells; and 3) by soluble factors present in the tissue microenvironment. The complex interplay of immune regulatory signals is perturbed in tumor tissues, favoring suppression of anti-tumor immunity. Analysis of pro-inflammatory and anti-inflammatory signals can generate a profile for a participant that can be entered into the integrated, molecular, omics (included, but not limited to, genomics, proteomics, lipid-omics), immunotherapy, metabolic, epigenetic, and clinical database of the disclosure.

The biological sample can include, but is not limited to, cell-free deoxyribonucleic acid (cfDNA) molecules, cellular deoxyribose nucleic acid (cDNA) molecules, ribonucleic acid (RNA) molecules, or protein. The cfDNA molecules, the cDNA molecules, and the RNA molecules can be assayed for the presence or absence of the biological markers. The biological sample can comprise cell-free DNA (cfDNA). Dying tumor cells can release small pieces of nucleic acids into a subject's bloodstream. The small pieces of nucleic acids are cell-free circulating tumor DNA (ctDNA).

A biological sample can be subjected to genomics/sequencing, histological analysis, flow cytometry, microarray analysis, fluorescent in situ hybridization (FISH), mass spectrometry, genomic profile, or immune assays. Blood samples obtained from a participant can be processed to extract cfDNA data for genomic sequencing. In some embodiments, cfDNA is used to obtain whole genome low coverage sequencing, whole genome deep coverage sequencing, or whole exome standard coverage sequencing. Circulating tumor DNA, circulating nucleic acids, exosomes, or nucleic acids that are free in blood can be used for profile generation. Further, any current or new tests can be used for sample analysis and profile generation.

Circulating tumor DNA can also be used non-invasively to monitor tumor progression and determine whether a patient's tumor can react to targeted treatments. For example, the patient's ctDNA can be screened for mutations both before therapy and after therapy and drug treatment. During the therapy, developing somatic mutations can prevent the drug from working. For example, the patients can observe an initial tumor response to the drug. This response can signal that the drug was initially effective in killing tumor cells. However, the development of new mutations can prevent the drug from continuing to work. Obtaining this critical information can assist doctors and oncologists in identifying that the subject's tumors are no longer responsive and different treatments are necessary. Circulating tumor DNA testing can be applicable to every stage of cancer subject care and clinical studies. Since ctDNA can be detected in most types of cancer at both early and advanced stages, ctDNA can be used as an effective screening method for most patients. A measurement of the levels of ctDNA in blood can also efficiently indicate a subject's stage of cancer and survival chances.

Various methods can be used to sequence DNA in addition to those discussed above. Techniques for sequencing DNA include, but are not limited to, exome sequencing, transcriptome sequencing, genome sequencing, and cell-free DNA sequencing. Cell-free DNA sequencing can include, but is not limited to, mismatch targeted sequencing (Mita-Seq) or tethered elimination of termini (Tet-Seq).

An integrative sequencing approach can use a comprehensive, Pan-Cancer, panel to provide a broad landscape of the most frequent cancer genetic alterations for identifying informative and/or actionable mutations in patients with diseases (e.g., multiple myeloma). A panel more specifically targeted for the diseases (e.g., multiple myeloma) can be used in conjunction with this panel or at a later point during the effort. The Pan-Cancer cfDNA targeted panel of genes includes, but is not limited to, ABL1, ACTA2, ACTC1, ACVR2A, AKT1, AKT2, AKT3, ALK, APC, APOB, AR, ARAF, ARHGAP26, ARID1A, ARID1B, ARID2, ASXL1, ATM, ATR, ATRX, AURKA, AURKB, AXIN2, AXL, B2M, BABAM1, BAP1, BARD1, BCL2, BCL2L1, BCL6, BCLAF1, BCOR, BCORL1, BIRC3, BLM, BMPR1A, BRAF, BRCA1, BRCA2, BRCC3, BRD2, BRD3, BRD4, BRIP1, BUB1B, cl5orf55, CACNA1S, CARD11, CASP8, CBFB, CBL, CBLB, CBLC, CCND1, CCND2, CCND3, CCNE1, CD79A, CD79B, CDC27, CDC73, CDH1, CDK12, CDK4, CDK6, CDK8, CDKN1A, CDKN1B, CDKN1C, CDKN2A, CDKN2B, CDKN2C, CEBPA, CHEK1, CHEK2, CIC, COL3A1, CREBBP, CRKL, CRLF2, CSF1R, CTCF, CTNNB1, CUX1, CPLD, DAXX, DDB2, DDR2, DEPDC5, DICER1, DIS3, DKC1, DNM2, DNMT3A, DSC2, DSG2, DSP, DUSP6, E2F3, ECT2L, EGFR, EGLN1, EP300, EPCAM, EPHA3, ERBB2, ERBB3, ERBB4, ERCC1, ERCC2, ERCC3, ERCC4, ERCC5, ERCC6, ERG, ERRFI1, ESR1, ETV1, ETV4, ETV5, ETV6, EWSR1, EXT1, EXT2, EZH2, FAM123B, FAM175A, FAM46C, FAM5C, FANCA, FANCB, FANCC, FANCD2, FANCE, FANCF, FANCG, FANCI, FANCL, FANCM, FAS, FBN1, FBXO11, FBXW7, FGFR1, FGFR2, FGFR3, FH, FKBP9, FLCN, FLT1, FLT3, FLT4, FOXA1, FOXL2, FUBP1, GAB2, GATA3, GATA4, GATA6, GLA, GNA11, GNAQ, GNAS, GOPC, GPC3, H3F3A, HGF, HIF1A, HLA-A, HLA-B, HLA-C, HNF1A, HRAS, IDH1, IDH2, IGF1R, IGF2, IGH, IKZF1, IL32, IL6ST, IL7R, INPP4B, IRS2, JAK1, JAK2, JAK3, JUN, KAT6A, KAT6B, KCNH2, KCNQ1, KDM5A, KDM5C, KDM5D, KDM6A, KDR, KEAP1, KIAA1549, KIF1B, KIT, KLF5, KLF6, KLLN, KRAS, LDLR, LMNA, LMO1, MAP2K1, MAP2K2, MAP2K4, MAP3K1, MAPK1, MAPK3, MAX, MC1R, MCL1, MDM2, MDM4, MED12, MEN1, MET, MITF, MLH1, MLL, MLL2, MLL3, MPL, MRE11A, MSH2, MSH6, MSR1, MTOR, MUTYH, MYB, MYBL1, MYBPC3, MYC, MYCL1, MYCN, MYD88, MYH11, MYH7, MYL2, MYL3, MYLK, NBN, NCOR1, NF1, NF2, NFE2L2, NFKBIA, NHP2, NKX2-1, NOP10, NOTCH1, NOTCH2, NPM1, NPNT, NPRL2, NRAS, NSD1, NTRK1, NTRK2, NTRK3, PALB2, PARK2, PAX5, PBRM1, PCSK9, PDGFRA, PDGFRB, PHF6, PHOX2B, PIK3CA, PIK3R1, PKP2, PMS1, PMS2, POLD1, POLE, POLH, POT1, PPKAG2, PPKAR1A, PPP2R1A, PRDM1, PREX2, PRF1, PRIM2, PRSS1, PTCH1, PTEN, PTPN11, PTPRD, QKI, RAB35, RAD21, RAD50, RAD51, RAD51C, RAD51D, RAF1, RARA, RB1, RBBP8, RBM10, RBM12, RECQL4, REL, RET, RHEB, RICTOR, RNF43, ROS1, RPS6KA3, RPTOR, RREB1, RUNX1, RYR1, RYR2, SBDS, SCN5A, SDHA, SDHAF2, SDHB, SDHC, SDHD, SETBP1, SETD2, SF3B1, SH2B3, SHH, SHOC2, SLITRK6, SLX4, SMAD2, SMAD3, SMAD4, SMARCA4, SMARCB1, SMC1A, SMC3, SMO, SOCS1, SOS1, SOX2, SOX9, SPG20, SPOP, SPRED1, SRC, SRSF2, STAG2, STAT3, STK11, SUFU, SYK, TBX3, TCF3, TCF7L1, TCF7L2, TERC, TERT, TET2, TGFBR1, TGFBR2, TGIF1, TINF2, TLR4, TMEM127, TMEM43, TMPRSS2, TNFAIP3, TNFRSF14, TNNI3, TNNT2, TP53, TP53BP1, TPM1, TSC1, TSC2, TSHR, TXNIP, U2AF1, UIMC1, VEGFA, VHL, WAS, WRN, WT1, XPA, XPC, XPO1, XRCC2, XRCC3, ZFP36L2, ZNF217, ZNRF3, or ZRSR2.

In addition to sequencing, other reactions and/or operations can occur within the systems and methods disclosed herein, including but not limited to: nucleic acid quantification, sequencing optimization, detecting gene expression, quantifying gene expression, genomic profiling, cancer profiling, and analysis of expressed markers. Assays include, but are not limited to, immunohistochemistry profiling and genomic profiling of the biological sample. In immunohistochemistry, antigens can be identified during examination of the tumor and normal tissue cells of the biological sample. Immunohistochemistry can also provide results on the distribution and localization of biomarkers and differentially-expressed proteins in different locations of the biological sample tissue. The differentially-expressed proteins can be over or under-expressed proteins.

A biological sample can be analyzed to detect, for example, high blood calcium levels, poor kidney function, low red blood cell counts (i.e., anemia), or an increase in one type of light chains in the blood such that one type is at least about 50, 100, 150, 200, 250, 300, 350, 400 times, or more, more common than the other. A biological sample can be analyzed to detect, for example, high blood calcium levels, poor kidney function, low red blood cell counts (i.e., anemia), or an increase in one type of light chains in the blood such that one type is at most about 500, 450, 400, 350, 300, 250, 200, 150, 100, 50, 25 times, or less, more common than the other. A participant can also be tested to detect holes in bones from tumor growth using imaging studies, or tested to detect abnormal areas in bones or bone marrow using magnetic resonance imaging (Mill) scans.

A biological sample can be analyzed for the presence of smoldering myeloma (i.e., early myeloma that does not cause any symptoms). In some embodiments, a biological sample is analyzed for plasma cells in the bone marrow, high levels of M protein in the blood, or high levels of light chains in the urine (i.e., Bence Jones protein).

A biological sample can also be analyzed for light chain amyloidosis. In some embodiments, a biological sample is analyzed for elevated free light chains in the blood, elevated light chains in the urine (i.e., Bence Jones protein), or abnormal plasma cells in the bone marrow.

A biological sample can be subjected to DNA sequencing and Genome Analysis Toolkit (GATK) analysis to obtain genotyping data. In some embodiments, a biological sample is subjected to Affymetrix™ Genome-Wide Human single nucleotide polymorphism (SNP) arrays, Agilent™ array-based comparative genomic hybridization (aCGH) analysis, gene expression, resequencing, and RNA interference (RNAi). In some embodiments, a biological sample is subjected to easy-to-use screens that promote differential expression analysis, gene neighbors analysis, gene set enrichment analysis, or analyzed using a genome browser.

A biological sample can be subjected to immune phenotype analysis or characterization by detecting or determining the relative expression of specific cell surface and intracellular markers and combinations thereof. For example, a biological sample can be subjected to immune phenotype analysis or characterization by detecting or determining the relative expression of cell markers, such as, but are not limited to, 1-40-β-amyloid, 4-1BB, SAC, 5T4, 707-AP, A kinase anchor protein 4 (AKAP-4), activin receptor type-2B (ACVR2B), activin receptor-like kinase 1 (ALK1), adenocarcinoma antigen, adipophilin, adrenoceptor β 3 (ADRB3), AGS-22M6, a folate receptor, α-fetoprotein (AFP), AIM-2, anaplastic lymphoma kinase (ALK), androgen receptor, angiopoietin 2, angiopoietin 3, angiopoietin-binding cell surface receptor 2 (Tie 2), anthrax toxin, AOC3 (VAP-1), B cell maturation antigen (BCMA), B7-H3 (CD276), *Bacillus anthracis* anthrax, B-cell activating factor (BAFF), B-lymphoma cell, bone marrow stromal cell antigen 2 (BST2), Brother of the Regulator of Imprinted Sites (BORIS), C242 antigen, C5, CA-125, cancer antigen 125 (CA-125 or MUC16), Cancer/testis antigen 1 (NY-ESO-1), Cancer/testis antigen 2 (LAGE-1a), carbonic anhydrase 9 (CA-IX), Carcinoembryonic antigen (CEA), cardiac myosin, CCCTC-Binding Factor (CTCF), CCL11 (eotaxin-1), CCR4, CCR5, CD11, CD123, CD125, CD140a, CD147 (basigin), CD15, CD152, CD154 (CD40L), CD171, CD179a, CD18, CD19, CD2, CD20, CD200, CD22, CD221, CD23 (IgE receptor), CD24, CD25 (a chain of IL-2 receptor), CD27, CD274, CD28, CD3, CD3 ε, CD30, CD300 molecule-like family member f (CD300LF), CD319 (SLAMF7), CD33, CD37, CD38, CD4, CD40, CD40 ligand, CD41, CD44 v7, CD44 v8, CD44 v6, CD5, CD51, CD52, CD56, CD6, CD70, CD72, CD74, CD79A, CD79B, CD80, CD97, CEA-related antigen, CFD, ch4D5, chromosome X open reading frame 61 (CXORF61), claudin 18.2 (CLDN18.2), claudin 6 (CLDN6), *Clostridium difficile*, clumping factor A, CLCA2, colony stimulating factor 1 receptor (CSF1R), CSF2, CTLA-4, C-type lectin domain family 12 member A (CLEC12A), C-type lectin-like molecule-1 (CLL-1 or CLECL1), C-X-C chemokine receptor type 4, cyclin B1, cytochrome P4501B1 (CYP1B1), cyp-B, cytomegalovirus, cytomegalovirus glycoprotein B, dabigatran, DLL4, DPP4, DR5, *E. coli* shiga toxin type-1, *E. coli* shiga toxin type-2, ecto-ADP-ribosyltransferase 4 (ART4), EGF-like module-containing mucin-like hormone receptor-like 2 (EMR2), EGF-like-domain multiple 7 (EGFL7), elongation factor 2 mutated (ELF2M), endotoxin, Ephrin A2, Ephrin B2, ephrin type-A receptor 2, epidermal growth factor receptor (EGFR), epidermal growth factor receptor variant III (EG-FRvIII), episialin, epithelial cell adhesion molecule (Ep-CAM), epithelial glycoprotein 2 (EGP-2), epithelial glycoprotein 40 (EGP-40), ERBB2, ERBB3, ERBB4, ERG (transmembrane protease, serine 2 (TMPRSS2) ETS fusion gene), *Escherichia coli*, ETS translocation-variant gene 6, located on chromosome 12p (ETV6-AML), F protein of respiratory syncytial virus, FAP, Fc fragment of IgA receptor (FCAR or CD89), Fc receptor-like 5 (FCRL5), fetal acetylcholine receptor, fibrin II 0 chain, fibroblast activation protein a (FAP), fibronectin extra domain-B, FGF-5, Fms-Like Tyrosine Kinase 3 (FLT3), folate binding protein (FBP), folate hydrolase, folate receptor 1, folate receptor α, folate receptor β, Fos-related antigen 1, Frizzled receptor, Fucosyl GM1, G250, G protein-coupled receptor 20 (GPR20), G protein-coupled receptor class C group 5, member D (GPRC5D), ganglioside G2 (GD2), GD3 ganglioside, glycoprotein 100 (gp100), glypican-3 (GPC3), GMCSF receptor α-chain, GPNMB, GnT-V, growth differentiation factor 8, GUCY2C, heat shock protein 70-2 mutated (mut hsp70-2), hemagglutinin, Hepatitis A virus cellular receptor 1 (HAVCR1), hepatitis B surface antigen, hepatitis B virus, HER1, HER2/neu, HER3, hexasaccharide portion of globoH glycoceramide (GloboH), HGF, HHGFR, high molecular weight-melanoma-associated antigen (HMW-MAA), histone complex, HIV-1, HLA-DR, HNGF, Hsp90, HST-2 (FGF6), human papilloma virus E6 (HPV E6), human papilloma virus E7 (HPV E7), human scatter factor receptor kinase, human Telomerase reverse transcriptase (hTERT), human TNF, ICAM-1 (CD54), iCE, IFN-α, IFN-β, IFN-γ, IgE, IgE Fc region, IGF-1, IGF-1 receptor, IGHE, IL-12, IL-13, IL-17, IL-17A, IL-17F, IL-1β, IL-20, IL-22, IL-23, IL-31, IL-31RA, IL-4, IL-5, IL-6, IL-6 receptor, IL-9, immunoglobulin lambda-like polypeptide 1 (IGLL1), influenza A hemagglutinin, insulin-like growth factor 1 receptor (IGF-I receptor), insulin-like growth factor 2 (ILGF2), integrin α4β7, integrin β2, integrin α2, integrin α4, integrin α5β1, integrin α7β7, integrin αIIbβ3, integrin αvβ3, interferon α/β receptor, interferon γ-induced protein, Interleukin 11 receptor α (IL-11Rα), Interleukin-13 receptor subunit α-2 (IL-13Ra2 or CD213A2), intestinal carboxyl esterase, kinase domain region (KDR), KIR2D, KIT (CD117), L1-cell adhesion molecule (L1-CAM), legumain, leukocyte immunoglobulin-like receptor subfamily A member 2 (LILRA2), leukocyte-associated immunoglobulin-like receptor 1 (LAIR1), Lewis-Y antigen, LFA-1 (CD11a), LINGO-1, lipoteichoic acid, LOXL2, L-selectin (CD62L), lymphocyte antigen 6 complex, locus K 9 (LY6K), lymphocyte antigen 75 (LY75), lymphocyte-specific protein tyrosine kinase (LCK), lymphotoxin-α (LT-α) or Tumor necrosis factor-β (TNF-β), macrophage migration inhibitory factor (MIF or MMIF), M-CSF, mammary gland differentiation antigen (NY-BR-1), MCP-1, melanoma cancer testis antigen-1 (MAD-CT-1), melanoma cancer testis antigen-2 (MAD-CT-2), melanoma inhibitor of apoptosis (ML-IAP), melanoma-associated antigen 1 (MAGE-A1), mesothelin, mucin 1, cell surface associated (MUC1), MUC-2, mucin CanAg, myelin-associated glycoprotein, myostatin, N-Acetyl glucosaminyl-transferase V (NA17), NCA-90 (granulocyte antigen), nerve growth factor (NGF), neural apoptosis-regulated proteinase 1, neural cell adhesion molecule (NCAM), neurite outgrowth inhibitor (e.g., NOGO-A, NOGO-B, NOGO-C), neuropilin-1 (NRP1), N-glycolylneuraminic acid, NKG2D, Notch receptor, o-acetyl-GD2 ganglioside (OAcGD2), olfactory receptor 51E2 (OR51E2), oncofetal antigen (h5T4), oncogene fusion protein consisting of breakpoint cluster region (BCR) and Abelson murine leukemia viral oncogene homolog 1 (Abl) (bcr-abl), *Oryctolagus cuniculus*, OX-40, oxLDL, p53 mutant, paired box protein Pax-3 (PAX3), paired box protein Pax-5 (PAX5), pannexin 3 (PANX3), phosphate-sodium co-transporter, phosphatidylserine, placenta-specific 1 (PLAC1), platelet-derived growth factor receptor α (PDGF-R α), platelet-derived growth factor receptor β (PDGFR-β), polysialic acid, proacrosin binding protein sp32 (OY-TES1), programmed cell death protein 1 (PD-1), proprotein convertase subtilisin/kexin type 9 (PCSK9), prostase, prostate carcinoma tumor antigen-1 (PCTA-1 or Galectin 8), melanoma antigen recognized by T cells 1 (MelanA or MART1), P15, P53, PRAME, prostate stem cell antigen (PSCA), prostate-specific membrane antigen (PSMA), prostatic acid phosphatase (PAP), prostatic carcinoma cells, prostein, Protease Serine 21 (Testisin or PRSS21), Proteasome (Prosome, Macropain) Subunit, β Type, 9 (LMP2), *Pseudomonas aeruginosa*, rabies virus glycoprotein, RAGE, Ras Homolog Family Member C (RhoC), receptor activator of nuclear factor kappa-B ligand (RANKL), Receptor for Advanced Glycation Endproducts (RAGE-1), receptor tyrosine kinase-like orphan receptor 1 (ROR1), renal ubiquitous 1 (RU1), renal ubiquitous 2 (RU2), respiratory syncytial virus, Rh blood group D antigen, Rhesus factor, sarcoma translocation breakpoints, sclerostin (SOST), selectin P, sialyl Lewis adhesion molecule (sLe), sperm protein 17 (SPA17), sphingosine-1-phosphate, squamous cell carcinoma antigen recognized by T Cells 1, 2, and 3 (SART1, SART2, and SART3), stage-specific embryonic antigen-4 (SSEA-4), *Staphylococcus aureus*, STEAP1, surviving, syndecan 1 (SDC1)+A314, SOX10, survivin, surviving-2B, synovial sarcoma, X breakpoint 2 (SSX2), T-cell receptor, TCR Γ Alternate Reading Frame Protein (TARP), telomerase, TEM1, tenascin C, TGF-β (e.g., TGF-β 1, TGF-β 2, TGF-β 3), thyroid stimulating hormone receptor (TSHR), tissue factor pathway inhibitor (TFPI), Tn antigen ((Tn Ag) or (GalNAcα-Ser/Thr)), TNF receptor family member B cell maturation (BCMA), TNF-α, TRAIL-R1, TRAIL-R2, TRG, transglutaminase 5 (TGS5), tumor antigen CTAA16.88, tumor endothelial marker 1 (TEM1/CD248), tumor endothelial marker 7-related (TEM7R), tumor protein p53 (p53), tumor specific glycosylation of MUC1, tumor-associated calcium signal transducer 2, tumor-associated glycoprotein 72 (TAG72), tumor-associated glycoprotein 72 (TAG-72)+

A327, TWEAK receptor, tyrosinase, tyrosinase-related protein 1 (TYRP1 or glycoprotein 75), tyrosinase-related protein 2 (TYRP2), uroplakin 2 (UPK2), vascular endothelial growth factor (e.g., VEGF-A, VEGF-B, VEGF-C, VEGF-D, PIGF), vascular endothelial growth factor receptor 1 (VEGFR1), vascular endothelial growth factor receptor 2 (VEGFR2), vimentin, v-myc avian myelocytomatosis viral oncogene neuroblastoma derived homolog (MYCN), von Willebrand factor (VWF), Wilms tumor protein (WT1), X Antigen Family, Member 1A (XAGE1), β-amyloid, and κ-light chain, and variants thereof.

In some embodiments, a biological sample can be subjected to immune phenotype analysis or characterization by detecting or determining the relative expression of cell markers, such as, but not limited to, 707-AP, a biotinylated molecule, a-Actinin-4, abl-bcr alb-b3 (b2a2), abl-bcr alb-b4 (b3a2), adipophilin, AFP, AIM-2, Annexin II, ART-4, BAGE, b-Catenin, bcr-abl, bcr-abl p190 (e1a2), bcr-abl p210 (b2a2), bcr-abl p210 (b3a2), BING-4, CAG-3, CAIX, CAMEL, Caspase-8, CD171, CD19, CD20, CD22, CD23, CD24, CD30, CD33, CD38, CD44v7/8, CDC27, CDK-4, CEA, CLCA2, Cyp-B, DAM-10, DAM-6, DEK-CAN, EGFRvIII, EGP-2, EGP-40, ELF2, Ep-CAM, EphA2, EphA3, erb-B2, erb-B3, erb-B4, ES-ESO-1a, ETV6/AML, FBP, fetal acetylcholine receptor, FGF-5, FN, G250, GAGE-1, GAGE-2, GAGE-3, GAGE-4, GAGE-5, GAGE-6, GAGE-7B, GAGE-8, GD2, GD3, GnT-V, Gp100, gp75, Her-2, HLA-A*0201-R170I, HMW-MAA, HSP70-2 M, HST-2 (FGF6), HST-2/neu, hTERT, iCE, IL-11Rα, IL-13Ra2, KDR, KIAA0205, K-RAS, L1-cell adhesion molecule, LAGE-1, LDLR/FUT, Lewis Y, MAGE-1, MAGE-10, MAGE-12, MAGE-2, MAGE-3, MAGE-4, MAGE-6, MAGE-A1, MAGE-A2, MAGE-A3, MAGE-A6, MAGE-B1, MAGE-B2, Malic enzyme, Mammaglobin-A, MART-1/Melan-A, MART-2, MC1R, M-CSF, mesothelin, MUC1, MUC16, MUC2, MUM-1, MUM-2, MUM-3, Myosin, NA88-A, Neo-PAP, NKG2D, NPM/ALK, N-RAS, NY-ESO-1, OA1, OGT, oncofetal antigen (h5T4), OS-9, P polypeptide, P15, P53, PRAME, PSA, PSCA, PSMA, PTPRK, RAGE, ROR1, RU1, RU2, SART-1, SART-2, SART-3, SOX10, SSX-2, Survivin, Survivin-2B, SYT/SSX, TAG-72, TEL/AML1, TGFaRII, TGFbRII, TP1, TRAG-3, TRG, TRP-1, TRP-2, TRP-2/INT2, TRP-2-6b, Tyrosinase, VEGF-R2, WT1, α-folate receptor, or κ-light chain. In some embodiments, a biological sample can be subjected to immune phenotype analysis or characterization by detecting or determining the relative expression of cell markers, such as, but not limited to, a tumor associated antigen.

In some embodiments, a biological sample is subjected to immune analysis. In some embodiments, a biological sample is subjected to immune analysis to measure and characterize diversity and function of a participant's immune system, immune response, immune history, and/or immune competency. Comprehensive immune characterization of a sample can utilize methodologies and technologies such as, but not limited to, phenotypic, genomic, proteomic, serological, computer-assisted imaging and/or microbiome analytical approaches.

Grand Serology:

A biological sample can be subjected to grand serology; for example, a series of known tumor antigens can be assessed for the ability to elicit autoantibodies. For antigens showing humoral reactivity, mapping of linear epitopes can be assessed using overlapping peptide series covering the sequence of the antigen, to assess polyclonality and potential spreading over time. In a subset of patients, other immunoglobulin isotype or subclass usage can be assessed as well. In some embodiments, a tumor antigen-specific antibody responses can highlight a population specific behavior.

Immune Phenotyping:

A biological sample can be subjected to immune phenotyping; for example, a biological sample can be characterized by immune phenotyping of multiple myeloma and immune cell populations using analytical techniques. In some embodiments, a biological sample can be characterized using flow cytometry/fluorescence activated cell sorting (FC/FACS), mass spectrometry, highly multiplexed mass cytometry (CyTOF), immunocytochemistry, immunohistochemistry, multiplexed fluorescent immunocytochemistry or computer-assisted high content fluorescent imaging methodologies.

A biological sample can be subjected to immune phenotype analysis or characterization by detecting or determining the relative expression of specific cell surface and intracellular markers and combinations thereof. For example, a biological sample can be subjected to immune phenotype analysis or characterization by detecting or determining the relative expression of cell markers, such as, but not limited to, CD19, CD27, CD38, CD45, CD56, CD81, CD117, CD138, or CD319 for the identification of myeloma cells. A biological sample can also be subjected to immune phenotype analysis or characterization by detecting or determining the relative expression of cell markers, such as, but not limited to, CD3, CD4, CD8, CD11b, CD11c, CD14, CD15, CD16, CD19, CD20, CD25, CD127, or FoxP3 to identify specific immune cell functional subtypes, including, but not limited to, T-lymphocyte subtypes (T-helper, T-cytotoxic, T-regulatory), B-cells, NK, DC, MDSC.

Multiple myeloma and immune cells can be characterized for expression of cell markers associated with immunosuppression and with T-cell activation and with T-cell exhaustion. For example, multiple myeloma and immune cells can be characterized for expression of cell markers associated with immunosuppression and with T-cell activation and with T-cell exhaustion, including, but not limited to, CTLA-4, CD244, CD272, ICOS (CD278), ICOS-L, IFN-γ, IL-2, PD-1, PD-L1, PD-L2, TIM-3, and/or TNFα.

Proteomics and Seromics:

A biological sample can be subjected to proteomics and seromics analyses, such as, but not limited to, the detection and measurement of immune cytokines, chemokines, antibodies and tumor antigens, and/or other immune modulatory proteins and protein fragments. Proteomics and seromics analyses can be conducted using analytical techniques, for example, enzyme-linked immunosorbent assay (ELISA), enzyme immunoassay (EIA, e.g. ELISPOT), fluorescence immunoassay (FIA), luminescence immunoassay (Luminex cytokine bead array), and high content protein microarrays (ProtoArray), mass spectrometry, or advanced histological methodologies.

A biological sample can be subjected to proteomic analysis by detecting or determining the relative expression of specific cell surface and intracellular markers and combinations thereof. For example, a biological sample can be subjected to proteomic analysis by detecting or determining the relative expression of cell markers, for example, CD19, CD27, CD38, CD45, CD56, CD81, CD117, CD138, or CD319 to identify myeloma cells. A biological sample can also be subjected to proteomic analysis by detecting or determining the relative expression of cell markers, for example, CD3, CD4, CD8, CD11b, CD11c, CD14, CD15, CD16, CD19, CD20, CD25, CD127, or FoxP3 to identify specific immune cell functional subtypes, including, but not limited to, T-lymphocyte subtypes (T-helper, T-cytotoxic, T-regulatory), B-cells, NK, DC cells, or MDSC. In some embodiments, multiple myeloma and immune cells can be characterized for the expression of cell markers associated with immunosuppression, T-cell activation, or T-cell exhaustion. In some embodiments, multiple myeloma and immune cells can be characterized for the expression of cell markers, for example, CTLA-4, CD244, CD272, ICOS (CD278), ICOS-L, IFN-γ, IL-2, PD-1, PD-L1, PD-L2, TIM-3, TNFα, LAG3, A2AR, B7-H3, B7-H4, BTLA, IDO, KIR, or VISTA.

A biological sample can be subjected to proteomic analysis for soluble immune factors (e.g., chemokines and cytokines) known to mediate immune activation and suppression. For example, a biological sample can be subjected to proteomic analysis for soluble immune factors (e.g., chemokines and cytokines) known to promote immune cell mobilization. In some embodiments, non-limiting examples of cytokines include, but not limited to, 4-1BBL, activin βA, activin βB, activin activin artemin (ARTN), BAFF/BLyS/TNFSF138, BMP10, BMP15, BMP2, BMP3, BMP4, BMP5, BMP6, BMP7, BMP8a, BMP8b, bone morphogenetic protein 1 (BMP1), CCL1/TCA3, CCL11, CCL12/MCP-5, CCL13/MCP-4, CCL14, CCL15, CCL16, CCL17/TARC, CCL18, CCL19, CCL2/MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CD153/CD30L/TNFSF8, CD40L/CD154/TNFSF5, CD40LG, CD70, CD70/CD27L/TNFSF7, CLCF1, c-MPL/CD110/TPOR, CNTF, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, EDA-A1, FAM19A1, FAM19A2, FAM19A3, FAM19A4, FAM19A5, Fas Ligand/FASLG/CD95L/CD178, GDF10, GDF11, GDF15, GDF2, GDF3, GDF4, GDF5, GDF6, GDF7, GDF8, GDF9, glial cell line-derived neurotrophic factor (GDNF), growth differentiation factor 1 (GDF1), IFNA1, IFNA10, IFNA13, IFNA14, IFNA2, IFNA4, IFNA5/IFNaG, IFNA7, IFNA8, IFNB1, IFNE, IFNG, IFNZ, IFNω/IFNW1, IL11, IL18, IL18BP, IL1A, IL1B, IL1F10, IL1F3/IL1RA, IL1F5, IL1F6, IL1F7, IL1F8, IL1F9, IL1RL2, IL31, IL33, IL6, IL8/CXCL8, inhibin-A, inhibin-B, Leptin, LIF, LTA/TNFB/TNFSF1, LTB/TNFC, neurturin (NRTN), OSM, OX-40L/TNFSF4/CD252, persephin (PSPN), RANKL/OPGL/TNFSF11(CD254), TL1A/TNFSF15, TNFA, TNF-alpha/TNFA, TNFSF10/TRAIL/AP0-2L(CD253), TNFSF12, TNFSF13, TNFSF14/LIGHT/CD258, XCL1, or XCL2.

Factors associated with immune activation can include IL-1, IL-2, IL-6, IL-8, IL-12, IFN-α, IFN-γ, or TNFα. Factors associated with immune suppression can include, e.g. IL-4, IL-5, IL-10, or TGF-β. Non-cytokine/chemokine factors associated with immune modulation can include known checkpoint proteins, such as, but not limited to, soluble PD-1, PD-L1, PD-L2, or CTLA-4. In some embodiments, a biological sample can be subjected to seromic analysis to identify myeloma (tumor)-associated antigens and antibodies against tumor associated antigens.

Seromics can allow for the testing of thousands of human proteins simultaneously as potential targets of autoantibodies from patient serum or plasma. The method can require a few microliters of material, and can be customized for applications other than IgG antibody detection. In some embodiments, the method can require at least about 0.5, at least about 1, at least about 2, at least about 3, at least about 4, at least about 5, at least about 6, at least about 7, at least about 8, at least about 9, at least about 10, at least about 12, at least about 14, at least about 16, at least about 18, at least about 20 microliters of material, or more. In some embodiments, the method can require at most about 20, at most about 18, at most about 16, at most about 14, at most about 12, at most about 10, at most about 9, at most about 8, at most about 7, at most about 6, at most about 5, at most about 4, at most about 3, at most about 2, at most about 1 microliters of material, or less.

The seromic platform can be used to define biomarkers or sets of antigens present at baseline in specific patient populations, and that could be used as prognostic or predictive markers. Alternatively, seromics can comprehensively scan for serum antibody changes at the antigen-specific level between consecutive time points, for example following treatment. Candidate antigens identified by these methods can be confirmed by orthogonal approaches such as grand serology, an ELISA-based assay using recombinant protein antigens or overlapping peptide pools to quantify titers of antigen-specific antibodies.

Genomics:

A biological sample can be subjected to genomic analysis, for example, genomic and transcriptional profiling via whole genome sequencing, exome sequencing, RNAseq, and nucleic acid microarrays.

A biological sample can be subjected to RNA and/or DNA sequencing of immune molecules, for example, the T-cell antigen receptor (TCR), major histocompatibility receptors (MHC/HLA), and/or immunoglobulins or fragments isolated from immune cells (e.g. T-cells, B-cells, DC, NK, etc). Immune cells and specific cell populations can be isolated from the starting cell population to be used as a source of nucleic acids, which can be genomic DNA, or mRNA, or cDNA or portions thereof. In some embodiments, a participant's intestinal microbiota (as a modulator of local and systemic immune system) can be characterized using RNA and DNA sequencing approaches encompassing sequencing of the conserved 16S subunit of microbial ribosomal RNA (rRNA) and metagenomic sequencing.

A participant's EMR/EHR information can be used to generate a comprehensive medical history. In some embodiments, a participant's EMR and/or EHR can be used to track a participant's health condition, and the improvement or deterioration of drug responses over time.

Vβ Gene Utilization, B-Cell Receptor (BCR) and T-Cell Receptor (TCR) Sequencing:

A biological sample can be subjected to Vβ gene utilization, B-cell receptor and T-cell receptor sequencing; for example, in assessing the diversity of the TCR repertoire, genomic DNA can be isolated from mononuclear cell populations and submitted to amplification of the CDR3 region of TCR V chains using various assays and platforms. The assays can provide quantitative information with minimal amplification bias, in a platform agnostic fashion. This method can identify the frequency and unique identifying sequences of TCR or BCR clones. In cases where peripheral blood mononuclear cell samples from longitudinal cases are available, the changes in frequency of dominant clones can be tracked in a quantitative manner.

Cytometry Immunophenotypic Analyses Using CyTOF:

A biological sample can be subjected to cytometry immunophenotypic analyses using mass cytometry (CyTOF), which is conceptually similar to conventional flow cytometry, but employs antibodies conjugated to metal isotopes instead of fluorochromes. This analysis can allow for the simultaneous measurement of multiple parameters on individual cells with minimal signal overlap, minimal background and comparable signal intensity. The unique multiparametric analysis capabilities of the CyTOF can allow multiple traditional flow cytometry panels to be condensed into a single CyTOF panel, thereby reducing the amount of sample used and increasing the potential breadth and depth of phenotypic profiling. As a result, the amount of complex cytometry data that can be attained from rare samples containing small numbers of cells can be maximized.

In some embodiments, CyTOF can allow for simultaneous measurement of at least about 3 parameters, at least about 5 parameters, at least about 10 parameters, at least about 15 parameters, at least about 20 parameters, at least about 25 parameters, at least about 30 parameters, at least about 31 parameters, at least about 32 parameters, at least about 33 parameters, at least about 34 parameters, at least about 35 parameters, at least about 36 parameters, at least about 37 parameters, at least about 38 parameters, at least about 39 parameters, at least about 40 parameters, at least about 45 parameters, at least about 50 parameters, at least about 55 parameters, at least about 60 parameters, at least about 70 parameters, at least about 80 parameters, at least about 100 parameters, at least about 200 parameters, or more.

In some embodiments, CyTOF can allow for simultaneous measurement of at most about 200 parameters, at most about 100 parameters, at most about 80 parameters, at most about 70 parameters, at most about 60 parameters, at most about 55 parameters, at most about 50 parameters, at most about 45 parameters, at most about 40 parameters, at most about 39 parameters, at most about 38 parameters, at most about 37 parameters, at most about 36 parameters, at most about 35 parameters, at most about 34 parameters, at most about 33 parameters, at most about 32 parameters, at most about 31 parameters, at most about 30 parameters, at most about 25 parameters, at most about 20 parameters, at most about 15 parameters, at most about 10 parameters, at most about 5 parameters, at most about 3 parameters, or less.

In some embodiments, CyTOF can allow for the simultaneous measurement of 30 to 40 parameters on individual cells with minimal signal overlap, minimal background and comparable signal intensity.

Some of the challenges of performing cytometric analyses on samples containing small numbers of cells can comprise potential staining inconsistencies when pipetting small volumes of antibodies, and exacerbated cell loss during sample preparation and acquisition steps. In response, a mass cytometry barcoding strategy can be used. The mass cytometry barcoding strategy can allow for multiple samples to be pooled together, processed and analyzed as a single sample.

Mass cytometric barcoding approaches can employ isotope-labeled thiol-reactive chemical compounds to label samples in a binary coding fashion. While this approach can allow significant multiplexing, two limitations exist, including, requirement of prior permeabilization of the cells to allow access to intracellular thiol groups, and misidentification of cellular doublets of two distinct barcoded samples as a third barcode. An alternative barcoding approach can be employed that utilizes a panel of antibodies against ubiquitously expressed HLA-ABC antibody molecules, each labeled with a distinct mass tag that does not contribute significant crosstalk to other analysis channels. Samples can be labeled with these antibodies and combined prior to cell surface labeling, thereby improving staining consistency, reducing reagent consumption and minimizing cell loss associated with scarce samples at all stages of the sample preparation workflow. Furthermore, applying these antibodies in a combinatorial rather than a binary barcoding manner effectively eliminates the problem of doublet misidentification.

Using cell surface markers, comprehensive cellular subsets can be analyzed including, but not limited to, Plasmacytoid Dendritic Cells, Myeloid Dendritic Cells, Non-Canonical Monocytes, Canonical Monocytes, Natural Killer Cells, Effector T Killer Cells, Naïve T Killer Cells, Activated T Killer Cells, Memory T Killer Cells, Effector T Helper Cells, Naïve T Helper Cells, Activated T Helper Cells, Memory T Helper Cells, Th1, Th2 and Th17 cells, Memory B Cells, Naïve B Cells, or Plasma B Cells. Multiple samples can be barcoded and combined, using metals for the multiplex-CYTOF analysis. These data can be compared post-hoc among protocol patients to discern differences in populations.

In some embodiments, samples can be barcoded and combined at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 35, at least about 40, at least about 50, at least about 100 samples at a time, or more.

In some embodiments, samples can be barcoded and combined at most about 100, at most about 50, at most about 40, at most about 35, at most about 30, at most about 25, at most about 20, at most about 15, at most about 14, at most about 13, at most about 12, at most about 11, at most about 10, at most about 9, at most about 8, at most about 7, at most about 6, at most about 5, at most about 4, at most about 3, at most about 2 samples at a time, or less.

In some embodiments, samples can be barcoded and combined 10 at a time, using metals for the multiplex-CYTOF analysis.

Luminex Cytokine Analysis:

A biological sample can be subjected to cytokine analysis using samples assessed for the balance of Th1/Th2/Th9/Th17 cytokines, immunosuppressive or inflammatory cytokines and chemokines in the tumor microenviroment. Multiple targets can be measured and analyzed simultaneously from a single small volume of sample. The detection can occur at the picogram per milliliter (pg/ml) level for most targets with a dynamic range.

In some embodiments, targets can have a dynamic range of at least about 1 log, at least about 2 log, at least about 3 log, at least about 4 log, at least about 5 log, at least about 6 log, at least about 7 log, at least about 8 log, or more.

In some embodiments, targets can have a dynamic range of at most about at most about 8 log, at most about 7 log, at most about 6 log, at most about 5 log, at most about 4 log, at most about 3 log, at most about 2 log, at most about 1 log, or less.

In some embodiments, the detection can occur at the picogram per milliliter (pg/ml) level for most targets with a 3-4 log dynamic range.

The multiplex system can incorporate polystyrene microspheres that are internally dyed with two spectrally distinct fluorochromes. The unique fluorescent emission spectra of a given microsphere can identify each of the assays performed simultaneously in a single sample. A multiplex array can be created using precise ratios of these fluorochromes, consisting of different microsphere sets with specific spectral addresses. Each microsphere set can possess a different surface reactant. Microsphere sets can be designed to be distinguished by spectral addresses, thereby allowing multiple analytes to be measured simultaneously in a single reaction. Microspheres can be interrogated individually in a rapidly flowing fluid stream while passing by two separate lasers in the analyzer. High-speed digital signal processing can classify the microsphere based on its spectral address and can quantify the reaction on the surface in a few seconds per sample. High-speed digital signal processing can classify the microsphere based on spectral address and can quantify the reaction on the surface in at least about 0.5, at least about 1, at least about 2, at least about 3, at least about 4, at least about 5, at least about 6, at least about 7, at least about 8, at least about 9, at least about 10, at least about 12, at least about 14, at least about 16, at least about 18, at least about 20 seconds per sample, or more.

High-speed digital signal processing can classify the microsphere based on spectral address and can quantify the reaction on the surface in at most about 20, at most about 18, at most about 16, at most about 14, at most about 12, at most about 10, at most about 9, at most about 8, at most about 7. at most about 6, at most about 5, at most about 4, at most about 3, at most about 2, at most about 1 second per sample, or less.

In such a way, detailed sera cytokine profile in patients and control population can be measured.

In some embodiments, a multiplex array can comprise at least about 5, at least about 10, at least about 15, at least about 20, at least about 25, at least about 30, at least about 40, at least about 50, at least about 60, at least about 70, at least about 80, at least about 90, at least about 100, at least about 110, at least about 120, at least about 130, at least about 140, at least about 150, at least about 200, at least about 500 different microsphere sets, or more.

In some embodiments, a multiplex array can comprise at most about 500, at most about 200, at most about 150, at most about 140, at most about 130, at most about 120, at most about 110, at most about 100, at most about 90, at most about 80, at most about 70, at most about 60, at most about 50, at most about 40, at most about 30, at most about 25, at most about 20, at most about 15, at most about 10, at most about 5 different microsphere sets, or less.

In some embodiments, a multiplex array can comprise 100 different microsphere sets with specific spectral addresses.

In some embodiments, a multiplex array can allow for simultaneous measurement of at least about 5, at least about 10, at least about 15, at least about 20, at least about 25, at least about 30, at least about 40, at least about 50, at least about 60, at least about 70, at least about 80, at least about 90, at least about 100, at least about 110, at least about 120, at least about 130, at least about 140, at least about 150, at least about 200, at least about 500 different analytes, or more.

In some embodiments, a multiplex array can allow for simultaneous measurement of at most about 500, at most about 200, at most about 150, at most about 140, at most about 130, at most about 120, at most about 110, at most about 100, at most about 90, at most about 80, at most about 70, at most about 60, at most about 50, at most about 40, at most about 30, at most about 25, at most about 20, at most about 15, at most about 10, at most about 5 different analytes, or less.

In some embodiments, a multiplex array can allow up to 100 different analytes to be measured simultaneously in a single reaction.

DNA and RNA Sequencing of Immune Cells:

A biological sample can be subjected to DNA and RNA sequencing of immune cells in which single cells from selected immune cells populations can be sequenced, for example, for analysis of gene expression profiles and immune genomic polymorphisms.

Integrative Sequencing:

The major elements of the integrative sequencing approach can ensure consistency and reproducibility, through extensive process measures. These measures can ensure accuracy and optimize efficiency of data production. For example, the measures can ensure that every library receives the same coverage, so as to minimize the need for over-coverage or rework. The integrative sequencing approach steps can comprise the following. During sample receipt and qualification, barcoded tubes linked to the laboratory information management system (LIMS) can be prepared by the platform and sent to collaborators for shipment of samples. Sample barcodes can be used to ensure a seamless chain of custody and positive tracking throughout the sample's journey through the platform. Upon receipt, sample barcodes can be scanned to confirm sample position and alert any discrepancies. Next, all sample manipulations and movements can be recorded and stored using the tube's barcode and can later be use for troubleshooting. A team of professionals can be dedicated to the chain of custody of all samples entrusted to the platform. In some embodiments, the team of professionals can have access or can be the only individuals with access to long-term sample storage. The team of professionals can be responsible for dispensing samples as requested and immediately returning them to storage upon completion. As a result, samples can be transported efficiently while ensuring that a large number of samples are accounted for and immediately available for the sample's next destination. The cfDNA, blood or plasma for cfDNA extraction can be received directly or through a third party. During cfDNA isolation from blood or plasma, cfDNA from blood or plasma can be isolated using a circulating DNA kit.

In some embodiments, cfDNA can be isolated from at least about 0.5 mL, at least about 1 mL, at least about 2 mL, at least about 3 mL, at least about 4 mL, at least about 5 mL, at least about 6 mL, at least about 7 mL, at least about 8 mL, at least about 9 mL, at least about 10 mL, at least about 11 mL, at least about 12 mL, at least about 13 mL, at least about 14 mL, at least about 15 mL, at least about 20 mL, at least about 25 mL, at least about 30 mL, at least about 40 mL, at least about 50 mL, at least about 100 mL of blood or plasma, or more.

In some embodiments, cfDNA can be isolated from at most about 100 mL, at most about 50 mL, at most about 40 mL, at most about 30 mL, at most about 25 mL, at most about 20 mL, at most about 15 mL, at most about 14 mL, at most about 13 mL, at most about 12 mL, at most about 11 mL, at most about 10 mL, at most about 9 mL, at most about 8 mL, at most about 7 mL, at most about 6 mL, at most about 5 mL, at most about 4 mL, at most about 3 mL, at most about 2 mL, at most about 1 mL, at most about 0.5 mL of blood or plasma, or less.

In some embodiments, cfDNA from 5-10 mL blood or 4-6 mL plasma can be isolated using a circulating DNA kit.

cfDNA can be quantified and qualified using picogreen quantification. All cfDNA samples can be stored in storage tubes at a controlled temperature.

In some embodiments, samples can be stored at at least about −196° C., at least about −100° C., at least about −90° C., at least about −85° C., at least about −80° C., at least about −75° C., at least about −70° C., at least about −65° C., at least about −60° C., at least about −50° C., at least about −40° C., at least about −30° C., at least about −25° C., at least about −20° C., at least about −15° C., at least about −10° C., at least about −5° C., at least about 0° C., at least about 4° C., at least about 8° C. or at a higher temperature.

In some embodiments, samples can be stored at at most about 8° C., at most about 4° C., at most about 0° C., at most about −5° C., at most about −10° C., at most about −15° C., at most about −20° C., at most about −25° C., at most about −30° C., at most about −40° C., at most about −50° C., at most about −60° C., at most about −65° C., at most about −70° C., at most about −75° C., at most about −80° C., at most about −85° C., at most about −90° C., at most about −100° C., at most about −196° C., or at a lower temperature.

In some embodiments, cfDNA samples can be stored in storage tubes at −20° C.

The LIMS can track the number of transfers that samples have undergone. During automated sample preparation, positive and negative controls can be added to batches containing analytical samples. All fluid handling steps can be automated on liquid handling robots that scan and record receptacle and plate barcodes. In some embodiments, custom messaging scripts can send preparation records to the LIMS, capturing information regarding the preparation, the reagents, the samples, and the quality control steps. During the addition of control samples, each step in the experimental process can involve rigorous quality control analysis. Standard control samples and duplicates can be analyzed. For example, in the liquid biopsy protocol, NA12878 HapMap control can be run in each batch of samples (e.g., 96 samples). Any deviations from normal performance can flag a potential problem.

In some embodiments, a batch of samples can comprise at least about 2, at least about 3, at least about 5, at least about 8, at least about 10, at least about 12, at least about 20, at least about 24, at least about 30, at least about 40, at least about 48, at least about 50, at least about 60, at least about 70, at least about 80, at least about 90, at least about 96, at least about 100, at least about 150, at least about 200, at least about 300, at least about 384, at least about 500, at least about 1000, at least about 1500, at least about 1536, at least about 2000 samples, or more.

In some embodiments, a batch of samples can comprise at most about 2000, at most about 1536, at most about 1500, at most about 1000, at most about 500, at most about 384, at most about 300, at most about 200, at most about 150, at most about 100, at most about 96, at most about 90, at most about 80, at most about 70, at most about 60, at most about 50, at most about 48, at most about 40, at most about 30, at most about 24, at most about 20, at most about 12, at most about 10, at most about 8, at most about 5, at most about 3, at most about 2 samples, or less.

In some embodiments, a batch can comprise 96 samples.

During automated ULPWGS library construction, samples can be plated into barcoded plates and processed by liquid-handling robots, with all information about reagents, samples, and quality metrics recorded in the LIMS. The automated liquid biopsy sequencing can include, but is not limited to, the following steps. First, cfDNA can be plated as the input for amplified libraries and can be quantified for performance assessment.

In some embodiments, at least about 1 ng, at least about 3 ng, at least about 5 ng, at least about 10 ng, at least about 15 ng, at least about 20 ng, at least about 25 ng, at least about 30 ng, at least about 35 ng, at least about 40 ng, at least about 45 ng, at least about 50 ng, at least about 55 ng, at least about 60 ng, at least about 70 ng, at least about 80 ng, at least about 90 ng, at least about 100 ng, at least about 200 ng, at least about 300 ng, at least about 400 ng, at least about 500 ng, at least about 1000 ng of cfDNA can be plated, or more.

In some embodiments, at most about 1000 ng, at most about 500 ng, at most about 400 ng, at most about 300 ng, at most about 200 ng, at most about 100 ng, at most about 90 ng, at most about 80 ng, at most about 70 ng, at most about 60 ng, at most about 55 ng, at most about 50 ng, at most about 45 ng, at most about 40 ng, at most about 35 ng, at most about 30 ng, at most about 25 ng, at most about 20 ng, at most about 15 ng, at most about 10 ng, at most about 5 ng, at most about 3 ng, at most about 1 ng of cfDNA can be plated, or less.

In some embodiments, 5-50 ng of cfDNA can be plated as the input for amplified libraries and can be quantified for performance assessment.

qPCR can be performed on the ULPWGS libraries and the libraries can be normalized.

In some embodiments, libraries can be normalized to at least about 0.001 nM, at least about 0.01 nM, at least about 0.1 nM, at least about 0.5 nM, at least about 1 nM, at least about 1.5 nM, at least about 2 nM, at least about 3 nM, at least about 5 nM, at least about 10 nM, at least about 20 nM, at least about 30 nM, at least about 50 nM, at least about 100 nM, at least about 200 nM, at least about 500 nM, at least about 1000 nM, or more.

In some embodiments, libraries can be normalized to at most about 1000 nM, at most about 500 nM, at most about 200 nM, at most about 50 nM, at most about 30 nM, at most about 20 nM, at most about 10 nM, at most about 5 nM, at most about 3 nM, at most about 2 nM, at most about 1.5 nM, at most about 1 nM, at most about 0.5 nM, at most about 0.1 nM, at most about 0.01 nM, at most about 0.001 nM, or less.

In some embodiments, qPCR can be performed on the ULPWGS libraries and the libraries can be normalized to 2 nM.

Normalized libraries can then be used for sequencing. During quantification and sequencing, absolute quantification by qPCR can be performed and loaded across the appropriate number of flowcell lanes to achieve the desired target coverage. For liquid biopsy analysis, ULPWGS can generate a certain coverage.

In some embodiments ULPWGS can generate at least about 0.001×, at least about 0.01×, at least about 0.05×, at least about 0.1×, at least about 0.15×, at least about 0.2×, at least about 0.25×, at least about 0.3×, at least about 0.4×, at least about 0.5×, at least about 1×, at least about 2×, at least about 5×, at least about 10×, at least about 50×, at least about 100× coverage, or more.

In some embodiments, ULPWGS can generate at most about 100×, at most about 50×, at most about 10×, at most about 5×, at most about 2×, at most about 1×, at most about 0.5×, at most about 0.4×, at most about 0.3×, at most about 0.25×, at most about 0.2×, at most about 0.15×, at most about 0.1×, at most about 0.05×, at most about 0.01×, at most about 0.001× coverage, or less.

In some embodiments, ULPWGS can generate 0.1× to 0.3× coverage for liquid biopsy analysis.

The normalized libraries can be loaded onto the sequencing machines for 2×150 base pair (bp) reads. The normalized libraries can be loaded onto the sequencing machines for at least about 1, at least about 2, at least about 3, at least about 4, at least about 5, at least about 6, at least about 7, at least about 8, at least about 9, at least about 10 bp reads, or more. The normalized libraries can be loaded onto the sequencing machines for at most about 10, at most about 9, at most about 8, at most about 7, at most about 6, at most about 5, at most about 4, at most about 3, at most about 2 bp reads, or less.

In some embodiments, the base pair reads can comprise at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, at least about 200, at least about 250, at least about 300 base pairs, or more. In some embodiments, the base pair reads can comprise at most about 500, at most about 450, at most about 400, at most about 350, at most about 300, at most about 250, at most about 200, at most about 150, at most about 100, at most about 95, at most about 90, at most about 85, at most about 80, at most about 75, at most about 70, at most about 65, at most about 60, at most about 55, at most about 50, at most about 45, at most about 40, at most about 35, at most about 30, at most about 25, at most about 20, at most about 15, at most about 10, at most about 5 base pairs, or less.

The entire process can occur in individual tubes, strips, or in a multi-well format, and all samples can be electronically tracked through the process in real-time including, but not limited to, reagent lot numbers, specific automation used, time stamps for each process step, and automatic registration.

In some embodiments, the process can occur in individual tubes, strips of tubes, strips of 8 tubes, strips of 12 tubes, a 48 well format, a 96 well format, a 384 well format, a 1536 well format, a gene chip format, or an array plate format.

In some embodiments, the entire process can occur in a 96 well format.

During inline quality control, the process can comprise extensive inline quality control, as well as a number of metrics for every sequencing run, including, but not limited to, library duplication rate, library complexity, GC-bias, mean coverage, percentage of genome covered at various levels, cross contamination, oxidation-artifact q-score, and sample identity.

In some embodiments, the process can comprise at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 250, at least about 300, at least about 500 metrics for every sequencing run, or more.

In some embodiments, the process can comprise at most about 500, at most about 300, at most about 250, at most about 200, at most about 190, at most about 180, at most about 170, at most about 160, at most about 150, at most about 140, at most about 130, at most about 120, at most about 110, at most about 100, at most about 90, at most about 80, at most about 70, at most about 60, at most about 50, at most about 40, at most about 30, at most about 20, at most about 10 metrics for every sequencing run, or less.

During tumor purity quality control, in addition to the standard QC metrics, all ULPWGS libraries can be evaluated for tumor purity using ichorCNA. ichorCNA is a tool for estimating the fraction of tumor in cfDNA from ultralowpass whole genome sequencing (ULP-WGS, 0.1× coverage). ichorCNA can utilize a probabilistic model, implemented as a hidden Markov model (HMM), to simultaneously segment the genome, predict large-scale copy number alterations, and estimate the tumor fraction of a ULP-WGS. ichorCNA can be optimized for low coverage sequencing of samples and can be benchmarked using patient and healthy donor cfDNA samples.

In some embodiments, ichorCNA can be optimized for at least about 0.001×, at least about 0.01×, at least about 0.05×, at least about 0.1×, at least about 0.15×, at least about 0.2×, at least about 0.25×, at least about 0.3×, at least about 0.4×, at least about 0.5×, at least about 1×, at least about 2×, at least about 5×, at least about 10×, at least about 50×, at least about 100× coverage, or more.

In some embodiments, ichorCNA can be optimized for at most about 100×, at most about 50×, at most about 10×, at most about 5×, at most about 2×, at most about 1×, at most about 0.5×, at most about 0.4×, at most about 0.3×, at most about 0.25×, at most about 0.2×, at most about 0.15×, at most about 0.1×, at most about 0.05×, at most about 0.01×, at most about 0.001× coverage, or less.

ichorCNA can inform the presence or absence of tumor-derived DNA and guide the decision to perform whole exome or deeper whole genome sequencing. The quantitative estimate of tumor fraction can be used to calibrate the depth of sequencing to reach statistical power for identifying mutations in cell-free DNA. ichorCNA can detect large-scale copy number alterations from large cohorts by ultra-low-pass sequencing methodology and probabilistic model.

The detection of large-scale copy number alterations utilizes the core variant calling workflow including preprocessing and variant discovery. Preprocessing can include, but not limited to, mapping and duplicate marking for individual sequencing output. Local indel realignment can be subsequently performed jointly on the tumor normal pair. Prior base quality score recalibration (BQSR) and contrastive evaluation between the tumor and normal pair can be performed using somatic single nucleotide polymorphism and indel caller. The BQSR and contrastive evaluation can provide somatic single nucleotide variant and indel calls with a desired level of quality, fine-tuned to balance specificity and sensitivity.

The platform can use a custom LIMS to support laboratory operations and continuous improvement. The LIMS system can manage multiple unique projects that encompass transactions for a large number of samples.

In some embodiments, the LIMS system can manage at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 2000, at least about 3000, at least about 4000, at least about 5000, at least about 10000 unique projects, or more.

In some embodiments, the LIMS system can manage at most about 10000, at most about 5000, at most about 4000, at most about 3000, at most about 2000, at most about 1500, at most about 1400, at most about 1300, at most about 1200, at most about 1100, at most about 1000, at most about 900, at most about 800, at most about 700, at most about 600, at most about 500, at most about 400, at most about 300, at most about 200, at most about 100 unique projects, or less.

In some embodiments, the LIMS system can manage projects that encompass transactions for at least about $1 \times 10^4$, at least about $1 \times 10^5$, at least about $1 \times 10^6$, at least about $1.5 \times 10^6$, at least about $1.8 \times 10^6$, at least about $1.88 \times 10^6$, at least about $2 \times 10^6$, at least about $3 \times 10^6$, at least about $4 \times 10^6$, at least about $5 \times 10^6$, at least about $1 \times 10^7$, at least about $1 \times 10^8$, at least about $1 \times 10^9$, at least about $1 \times 10^{10}$ samples, or more.

In some embodiments, the LIMS system can manage projects that encompass transactions for at most about $1 \times 10^{10}$, at most about $1 \times 10^9$, at most about $1 \times 10^8$, at most about $1 \times 10^7$, at most about $5 \times 10^6$, at most about $4 \times 10^6$, at most about $3 \times 10^6$, at most about $2 \times 10^6$, at most about 1.88×10$^6$, at most about 1.8×10$^6$, at most about 1.5×10$^6$, at most about 1×10$^6$, at most about 1×10$^5$, at most about 1×10$^4$ samples, or less.

In some embodiments, the LIMS system can manage over 900 unique projects that encompass transactions for 1,880,304 samples.

In some embodiments, the LIMS system can manage over 900 unique projects that encompass transactions for 1,880,304 samples.

Key component pieces can include, but are not limited to, project management tools, laboratory data capture, workflow management, reporting, security, and quality metrics. The project management tools system can allow for submitting orders, tracking groups of samples, and returning data by using a cohort or study identification. Sample storage and management can comprise sample tracking. Sample tracking can be initiated by sending barcoded tubes or labels generated by the LIMS to collaborators for shipment of personal samples. Samples can be scanned upon receipt and compared to personal electronic manifest to ensure the received containers match what is expected. The sample management application can track date, time, and the technician responsible for all transactions involving the sample received including, but not limited to, storage location, check-in and check-out, extraction, or the use, depletion, disposal or return of all derivatives or aliquots. Volume, mass and concentration of incoming samples can also be recorded for quality control purposes. During laboratory data capture, when samples are selected for a laboratory process, samples can be removed from storage, plated at the proper concentration, and assigned to batches according to product workflow. All steps in each protocol can be tracked using integrated barcode scanning of deck inventory. Similar to the samples application, the laboratory workflow tracker can include direct messaging of who, what (e.g., samples plus reagents), where (e.g., to which instrument), and/or when each action occurs. In-process quality control values can be uploaded to facilitate reporting, trend tracking, and troubleshooting.

During worfklow management, all work in progress can be visually tracked using physical and electronic systems to show current load as compared to maximum capacity. Laboratory steps can be tracked using automated messaging from the robotic instruments and manual comments in the LIMS. Batches can be reprioritized by project managers to expedite urgent work while not disrupting production flow. For reporting, the platform can maintain an extensive data warehouse and suite of reporting tools for connecting sample attributes, laboratory processes, and final quality metrics. This capability can be used to assess quality values and quality trends and for guiding continuous improvement projects. Custom reports can aid in lab queue management, equipment use tracking, capacity planning, reagent-use forecasting, and troubleshooting. In the security component, each application can manage permissions according to the users' roles and the level of access needed to perform job responsibilities. All applications can include, but not limited to, audit trails to track data changes and/or updates. The real-time monitoring of quality metrics can include, but not limited to, assessment of real-time run performance during the run a Read 1 quality control (% PF bases) and a Read 2 quality control (% regeneration). A number of metrics can be generated for every sequencing run, once completed.

In some embodiments, at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 250, at least about 300, at least about 500 metrics can be generated for every sequencing run, or more.

In some embodiments, at most about 500, at most about 300, at most about 250, at most about 200, at most about 190, at most about 180, at most about 170, at most about 160, at most about 150, at most about 140, at most about 130, at most about 120, at most about 110, at most about 100, at most about 90, at most about 80, at most about 70, at most about 60, at most about 50, at most about 40, at most about 30, at most about 20, at most about 10 metrics can be generated for every sequencing run, or less.

All quality controls and associated metadata can be accessible in real-time and can be viewable from any network location using a commercial software platform. Custom reports and views can allow process measures to be examined at various levels including, but not limited to, batch, sample, cohort, instrument, date, or operator. Quality and performance measures can be reviewed weekly and used to improve the understanding of processes and to identify any special cause variation that can arise. In some embodiments, quality and performance measures can be reviewed every at least about 1 day, at least about 5 days, at least about 10 days, at least about 15 days, at least about 20 days, at least about 25 days, at least about 30 days, at least about 3 months, at least about 6 months, or more. In some embodiments, quality and performance measures can be reviewed every at most about 6 months, every at most about 3 months, every at most about 30 days, every at most about 25 days, every at most about 20 days, every at most about 15 days, every at most about 10 days, every at most about 5 days, every at most about 1 day, or less.

e. Clinical Data

The disclosure can include the collection of clinical data collected from or provided by participants enrolled in a study or data registry. In some embodiments, clinical data can comprise data collected by a medical care provider, any data generated from a diagnostic test, participant-reported data, demographic data, medical history and co-morbidity data, treatment data, medication data, symptom report data, complete blood count (CBC) data, clinical chemistry data (e.g., glucose levels, calcium levels, blood urea nitrogen (BUN) levels, creatinine levels, total protein levels, albumin levels, lactate dehydrogenase levels, etc.), serum immunology lab data (e.g., M-protein levels, quantitative immunoglobulins, free light chain (FLC) levels, beta-2-microglobulin levels, C-reactive protein levels, etc.), or urine immunology lab data (e.g., 24 hour total protein levels, M-protein levels, etc.).

Clinical data can also comprise medical imaging data, for example, magnetic resonance imaging (MRI), computerized tomography (CT), or positron emission tomography (PET) data. Clinical data can also comprise disease staging data, for example, multiple myeloma disease staging data. In some embodiments, clinical data can comprise a record of resource utilization, for example, the number of doctor visits, time spent per doctor visit, amount of time hospitalized, number of times hospitalized, or use of outpatient care facilities. In some embodiments, clinical data can comprise information of adverse effects of treatment and survival information. Clinical data can comprise cytogenetic analysis, for example, fluorescent in situ hybridization (FISH) can be performed in order to evaluate the number and/or normalcy of chromosomes or to identify chromosomal translocation events.

Clinical data can further comprise a bone assessment such as, but not limited to, a skeletal survey (e.g., a series of x-rays). In some embodiments, a bone assessment can assess changes in bone structure or determine the number and size of bone lesions or tumors.

Through the consenting process, participants can be asked to authorize linkage of EMR information. Specifically, longitudinal tracking of health outcomes through EHRs can be an important component. In some embodiments, the electronic health records can be collected and organized. Each patient can sign a privacy authorization form (e.g., authorization for use or disclosure of protected health information) allowing for request of the patient's medical records from the patient's provider. The patient can also supply the identity of the provider including, but not limited to, name and location. In some embodiments, a study code, patient identity, authorization form and/or provider identity can be retrieved from the registry. Conformance of the form and the identity of the provider can be assessed. The patient medical record can be requested from the patient's provider. The information can be inspected for completeness and any missing information can be requested from the provider. The medical record can be curated to a structured data record for the patient using technology and/or trained human abstractors and reviewers. The structured record can be de-identified removing any personally identifying information. The de-identified structured record can be retained and supplied to the database.

Some data collected can be deposited into databases such as Genotypes and Phenotypes (dbGaP) and Genomic Data Commons (GDC). The dbGaP and GDC are databases developed by the National Cancer Institute (NCI) to archive and distribute the results of studies that have investigated the interaction of genotype and phenotype. Data submitted from studies to dbGAP and GDC can only be available through controlled access and restricted to cancer research studies. Any researcher requesting access to the data can formally apply and present a research study rationale needing access to the data. The data can also be submitted to other future database systems which have similar access controls as dbGAP and GDC.

f. External Data

The disclosure can include the collection of data from external sources and entry of the collected data into the data warehouse. The external source of data can be data collected from an outside research program, an external grant, an academic medical center, a non-academic medical center, a community hospital, a foundation, non-profit organization, for-profit organization, or a government. In some embodiments, external data can be collected from more than one source. A cloud-based platform for the analysis, management, and sharing of data with authorized researchers can be used. Examples of data sources that can be valuable to link within cloud-based platform include, but are not limited to, death certificates, pharmacy system data, claims data, and health registry data. While data linkage is encompassed in the participant consent, an amendment can be filed for any linkages to health registries or claims data that require sharing of participant-identifying information to an outside entity. The amendment filing can occur prior to linking participant data with external sources. Such submissions can detail the data to be linked and the methods for doing so. The consent can indicate that identifying information can be shared in this process.

A committee can be formed to protect the confidentiality of study data and/or ensure the safety of participants. This committee can include, but is not limited to, the principal investigator and co-investigators, data managers or designees, or other members of the team involved with the conduct of the study. The committee can also consider factors external to the study, such as scientific developments that can impact the safety of participants or ethics of the study.

B. Participant Engagement

The integrated, molecular, omics (included, but not limited to, genomics, proteomics, lipidomics), immunotherapy, metabolic, epigenetic, and clinical database can comprise a participant's portal, and can allow a participant to input or revise the participant's biographical data, for example, a change in address or marital status. The integrated, molecular, omics (included, but not limited to, genomics, proteomics, lipidomics), immunotherapy, metabolic, epigenetic, and clinical database can allow a participant to input or revise the participant's biological data, for example, the participant's body weight. A participant can update the participant's information at least about every 1 month, at least about every 2 months, at least about every 3 months, at least about every 4 months, at least about every 5 months, at least about every 6 months, at least about every 7 months, at least about every 8 months, at least about every 9 months, at least about every 10 months, at least about every 11 months, at least about every 12 months, or more. A participant can update the participant's information at most about every 12 months, at most about every 11 months, at most about every 10 months, at most about every 9 months, at most about every 8 months, at most about every 7 months, at most about every 6 months, at most about every 5 months, at most about every 4 months, at most about every 3 months, at most about every 2 months, at most about every 1 month, or less. In some embodiments, a participant can update the participant's information at least about every 3 months, at least about 6 months, at least about 9 months, at least about 12 months, or more. In some embodiments, a participant can update the participant's information at most about every 12 months, at most about every 9 months, at most about every 6 months, at most about every 3 months, or less. In some embodiments, a participant can update the participant's information at least about every 18 months, at least about every 24 months, at least about every 36 months, at least about every 48 months, at least about every 60 months, or more. In some embodiments, a participant can update the participant's information at most about every 60 months, at most about every 48 months, at most about every 36 months, at most about every 24 months, at most about every 18 months, or less.

The integrated, molecular, omics (included, but not limited to, genomics, proteomics, lipidomics), immunotherapy, metabolic, epigenetic, and clinical database can comprise a messaging system that can allow for direct contact between a system administrator, researcher, or physician with a participant or a subset of participants. The integrated, molecular, omics (included, but not limited to, genomics, proteomics, lipidomics), immunotherapy, metabolic, epigenetic, and clinical database can also allow an administrator, researcher, or physician to contact all or a subset of participants for the acquisition of longitudinal data or consent for additional studies. The integrated, molecular, omics (included, but not limited to, genomics, proteomics, lipidomics), immunotherapy, metabolic, epigenetic, and clinical database can further allow for a participant to contact an administrator, researcher, or physician.

The integrated, molecular, omics (included, but not limited to, genomics, proteomics, lipidomics), immunotherapy, metabolic, epigenetic, and clinical database can allow a participant to visualize the progress of the participant's disease or a group of participant's diseases. The integrated, molecular, omics (included, but not limited to, genomics, proteomics, lipidomics), immunotherapy, metabolic, epigenetic, and clinical database can also allow a participant to visualize the progress of a defined group of participants' diseases, for example, participants of a particular genotype, ethnicity, or age group.

The integrated, molecular, omics (included, but not limited to, genomics, proteomics, lipidomics), immunotherapy, metabolic, epigenetic, and clinical database can allow a participant to visualize time progression curves of the participant or a group of participants. In some embodiments, the integrated, molecular, omics (included, but not limited to, genomics, proteomics, lipidomics), immunotherapy, metabolic, epigenetic, and clinical database can allow a participant to visualize time progression curves of a specific group of participants, for example, participants of a particular genotype, ethnicity, or age group.

The integrated, molecular, omics (included, but not limited to, genomics, proteomics, lipidomics), immunotherapy, metabolic, epigenetic, and clinical database can analyze data, visualize data, written text or transcripts, clinical trial matching, participant-updated data, or doctor-updated data in the form of a chart, graph, animation, or cartoon. The integrated, molecular, omics (included, but not limited to, genomics, proteomics, lipidomics), immunotherapy, metabolic, epigenetic, and clinical database can also allow a participant to download the visualization of data, for example, a typical course of treatment based on the participant's personal parameters, demographic, and diagnosis.

Participants registering can grant permission to the system for future contact to impart information to the participant, including but not limited to information on a clinical study which enrolls patients with characteristics of interest. Participants can receive messages from the integrated clinical database up to at least about 1, 2, 3, 4, 5, 6, 7, 8, 9, 10, 15, 20 times per month, or more. Participants can receive messages from the integrated clinical database up to at most about 30, 25, 20, 15, 10, 9, 8, 7, 6, 5, 4, 3, 2 times per month, or less. Messages can alternate between newsletters and invitations to engage in educational modules and surveys. Newsletter information can include, but is not limited to, program updates, (e.g., new enrollment numbers, local events, and new findings). Educational programming can include but is not limited to modules that utilize program data, and fundamental science learnings. Participants can also share reasons for enrolling. Future communications development can include but is not limited to the integrated clinical database app development and text messaging.

Participants can be contacted about opportunities to participate in research studies relevant to health or interests. These studies can include but are not limited to demographic studies, quality of life studies, patient preference studies, patient reported outcomes, and other surveys. Participants can be invited to participate in clinical studies including but not limited to targeted interventions and other therapies.

Registered patients can grant permission for future contact should information beneficial to the participant arise, such as a clinical study enrolling patients with the characteristics of interest. Personal identifiers can be removed from the biospecimen and clinical database, and can be connected to a participant's identity through a unique patient identification number. Access to files with patient identifiers and files with study outcomes can be restricted to core staff with any exceptions to be approved by the principal and co-investigators. In addition to use of passwords and other security measures, all documents containing identifying information on individuals or physicians can be considered confidential materials and can be safeguarded to the greatest possible extent.

Participants can be informed that the study can include risks that are currently unknown. When possible, the database can inform the participant if new risks are identified that could affect personal decisions to participate and/or strategies to minimize the risks.

In some embodiments, participants who provide a biospecimen can be invited to participate in genetic analysis at a future date. A specific genetic consent module can be developed and submitted for review to allow participants to opt into the genetic analysis.

In some embodiments, participants can, at any time, withdraw participation without giving a reason and without penalty. The participants can do so by notifying the patient support center and/or by selecting the withdrawal option on a web and/or mobile application. The withdrawal status of a given participant can be recorded within the database within a number of business days.

In some embodiments, the withdrawal status of a given participant can be recorded in the database within at least about 1, at least about 2, at least about 3, at least about 4, at least about 5, at least about 6, at least about 7, at least about 8, at least about 9, at least about 10, at least about 15, at least about 20, at least about 25, at least about 30, at least about 40, at least about 50, at least about 100, at least about 150, at least about 200 business days, or more.

In some embodiments, the withdrawal status of a given participant can be recorded in the database within at most about 200, at most about 150, at most about 100, at most about 50, at most about 40, at most about 30, at most about 25, at most about 20, at most about 15, at most about 10, at most about 9, at most about 8, at most about 7, at most about 6, at most about 5, at most about 4, at most about 3, at most about 2, at most about 1, business days, or less.

In some embodiments, the withdrawal status of a given participant can be recorded within the database within two business days.

Confirmation of withdrawal can be provided to participants via email and/or letter. Participants can be informed upon enrollment that the name and basic contact information cannot be destroyed, even after withdrawal, due to regulatory requirements (e.g., as part of archived consent forms). However, the information can be maintained securely. The participant's records can be flagged to show that the participant withdrew and does not want to be contacted. Participants who withdraw can no longer be contacted about follow-up opportunities, and no additional information can be collected about withdrawn participants.

Participants can be informed during the consenting process that data and/or specimens previously collected and already used in research cannot be withdrawn nor destroyed. For example, in some embodiments, it is not permitted to destroy all sample remnants and information already distributed or analyzed. In contrast, stored biospecimens that have not been analyzed or distributed to qualified researchers can be destroyed. Existing datasets, including data from withdrawn participants, can remain available to promote reproducibility of research. However, no new data or samples can be collected. Re-enrollment in the program can be allowed. However, participants who re-enroll after withdrawal can need to create new participant entries and/or donate new biospecimens.

C. Researcher Engagement

The integrated, molecular, omics (included, but not limited to, genomics, proteomics, lipidomics), immunotherapy, metabolic, epigenetic, and clinical database can comprise a researcher portal that can allow a researcher to analyze, survey, and share analysis results from a patient's or participant's integrated, molecular, omics (included, but not limited to, genomics, proteomics, lipidomics), immunotherapy, metabolic, epigenetic, and clinical data, for example, based on the analysis of new biological samples. In some embodiments, the integrated, molecular, genomic, and immunotherapy clinical database can allow a researcher to revise a participant's biological data, such as, but not limited to, diagnostic test data, treatment data, medication data, CBC data, clinical chemistry data, (e.g., glucose levels, calcium levels, blood urea nitrogen (BUN) levels, creatinine levels, total protein levels, albumin levels, lactate dehydrogenase levels, etc.), serum immunology lab data (e.g., M-protein levels, quantitative immunoglobulins, free light chain (FLC) levels, beta-2-microglobulin levels, C-reactive protein levels, etc.), or urine immunology lab data (e.g., 24 hour total protein levels, M-protein levels, etc.).

The integrated, molecular, omics (included, but not limited to, genomics, proteomics, lipidomics), immunotherapy, metabolic, epigenetic, and clinical database can comprise a messaging system. The integrated, molecular, omics (included, but not limited to, genomics, proteomics, lipidomics), immunotherapy, metabolic, epigenetic, and clinical database can allow for direct contact between a system administrator, participant, or physician with a researcher or group of researchers. In some embodiments, the integrated, molecular, omics (included, but not limited to, genomics, proteomics, lipidomics), immunotherapy, metabolic, epigenetic, and clinical database can allow a researcher to contact all or a subset of participants for the acquisition of longitudinal data or consent for additional studies. In some embodiments, the integrated, molecular, omics (included, but not limited to, genomics, proteomics, lipidomics), immunotherapy, metabolic, epigenetic, and clinical database can allow for a researcher to contact an administrator, participant, or physician.

The integrated, molecular, omics (included, but not limited to, genomics, proteomics, lipidomics), immunotherapy, metabolic, epigenetic, and clinical database can allow a researcher to visualize the progress of a participant's disease or a group of participant's diseases. In some embodiments, the integrated, molecular, omics (included, but not limited to, genomics, proteomics, lipidomics), immunotherapy, metabolic, epigenetic, and clinical database can allow a researcher to visualize the progress of a defined group of participants' diseases, for example, participants of a particular genotype, ethnicity, or age group.

The integrated, molecular, omics (included, but not limited to, genomics, proteomics, lipidomics), immunotherapy, metabolic, epigenetic, and clinical database can allow a researcher to visualize time progression curves of a participant or a group of participants. In some embodiments, the integrated, molecular, omics (included, but not limited to, genomics, proteomics, lipidomics), immunotherapy, metabolic, epigenetic, and clinical database can allow a researcher to visualize time progression curves of a specific group of participants, for example, participants of a particular genotype, ethnicity, or age group.

The integrated, molecular, omics (included, but not limited to, genomics, proteomics, lipidomics), immunotherapy, metabolic, epigenetic, and clinical database can allow a researcher to browse datasets and samples, run analyses on the data (e.g., statistical analysis), or create a workspace with a subset of data. In some embodiments, the integrated, molecular, omics (included, but not limited to, genomics, proteomics, lipidomics), immunotherapy, metabolic, epigenetic, and clinical database can allow a researcher to save analyzed data into a workspace.

In some embodiments, the integrated, molecular, omics (included, but not limited to, genomics, proteomics, lipidomics), immunotherapy, metabolic, epigenetic, and clinical database can visualize data in the form of a chart, graph, animation, or cartoon. In some embodiments, the integrated, molecular, omics (included, but not limited to, genomics, proteomics, lipidomics), immunotherapy, metabolic, epigenetic, and clinical database can allow a researcher to download the visualization of data.

The integrated, molecular, omics (included, but not limited to, genomics, proteomics, lipidomics), immunotherapy, metabolic, epigenetic, and clinical database can allow researchers to use data from other participant cohorts in a new research project, or allow researchers to use data from previous participant cohorts to design a new research project, for example, a new course of treatment or a new dosage of an existing drug.

D. Physician Engagement

The integrated, molecular, omics (included, but not limited to, genomics, proteomics, lipidomics), immunotherapy, metabolic, epigenetic, and clinical database can comprise a physician portal that can allow a physician to revise a participant's biological data, for example, based on the analysis of new biological samples; or allow a physician to revise a participant's biological data, such as, but not limited to, diagnostic test data, treatment data, medication data, CBC data, clinical chemistry data, (e.g., glucose levels, calcium levels, blood urea nitrogen (BUN) levels, creatinine levels, total protein levels, albumin levels, lactate dehydrogenase levels, etc.), serum immunology lab data (e.g., M-protein levels, quantitative immunoglobulins, free light chain (FLC) levels, beta-2-microglobulin levels, C-reactive protein levels, etc.), or urine immunology lab data (e.g., 24 hour total protein levels, M-protein levels, etc.). In some embodiments, the integrated, molecular, omics (included, but not limited to, genomics, proteomics, lipidomics), immunotherapy, metabolic, epigenetic, and clinical database can allow a physician to revise a participant's treatment plan, for example, type of medication, dosage, and treatment duration; or allow a physician to add to or revise a participant's clinical results, for example, MM scan results, holes in bones, tumor growth, or abnormal areas in bones or bone marrow.

The integrated, molecular, omics (included, but not limited to, genomics, proteomics, lipidomics), immunotherapy, metabolic, epigenetic, and clinical database can comprise a messaging system that can allow for direct contact between a system administrator, participant, or researcher with a physician or group of physician; allow a physician to contact all or a subset of participants for the acquisition of longitudinal data or consent for additional studies; or allow for a physician to contact an administrator, participant, or researcher.

The integrated, molecular, omics (included, but not limited to, genomics, proteomics, lipidomics), immunotherapy, metabolic, epigenetic, and clinical database can allow a physician to visualize the progress of a participant's disease or a group of participant's diseases. In some embodiments, the integrated, molecular, omics (included, but not limited to, genomics, proteomics, lipidomics), immunotherapy, metabolic, epigenetic, and clinical database can allow a physician to visualize the progress of a defined group of participants' diseases, for example, participants of a particular genotype, ethnicity, or age group.

The integrated, molecular, omics (included, but not limited to, genomics, proteomics, lipidomics), immunotherapy, metabolic, epigenetic, and clinical database can allow a physician to visualize time progression curves of a participant or a group of participants. In some embodiments, the integrated, molecular, omics (included, but not limited to, genomics, proteomics, lipidomics), immunotherapy, metabolic, epigenetic, and clinical database can allow a physician to visualize time progression curves of a specific group of participants, for example, participants of a particular genotype, ethnicity, or age group.

The integrated, molecular, omics (included, but not limited to, genomics, proteomics, lipidomics), immunotherapy, metabolic, epigenetic, and clinical database can allow a physician to browse datasets and samples, run analyses on the data (e.g., statistical analysis); allow a physician to create a workspace with a subset of data; or allow a physician to save analyzed data into a workspace. The integrated, molecular, omics (included, but not limited to, genomics, proteomics, lipidomics), immunotherapy, metabolic, epigenetic, and clinical database can also visualize data in the form of a chart, graph, animation, or cartoon; or allow a researcher to download the visualization of data.

The integrated, molecular, omics (included, but not limited to, genomics, proteomics, lipidomics), immunotherapy, metabolic, epigenetic, and clinical database can allow a physician to provide a new diagnosis, or recommend a new or different course of treatment. In some embodiments, the integrated, molecular, omics (included, but not limited to, genomics, proteomics, lipidomics), immunotherapy, metabolic, epigenetic, and clinical database can allow a physician to recommend a new or different course of treatment for a subset of participants, for example, participants of particular genotypes, ethnicity, or age groups.

E. Statistics

In some embodiments, the integrated, molecular, omics (including, but not limited to, genomics, proteomics, lipidomics), immunotherapy, metabolic, epigenetic, and clinical database can comprise a statistical analysis plan (SAP) including various statistical methodologies. Descriptive statistics can be provided for all variables assessed in the exploratory study. Statistics to be calculated include, but are not limited to, range, mean, median, and standard deviation for continuous variables; counts and proportions for categorical variables; or incidence rates and Kaplan-Meier curves for time-to-event variables.

In some embodiments, 95% confidence intervals can be provided when appropriate.

In some embodiments, at least about 70%, at least about 80%, at least about 85%, at least about 90%, at least about 95%, at least about 96%, at least about 97%, at least about 98%, at least about 99% confidence intervals can be provided.

In some embodiments, at most about 99%, at most about 98%, at most about 97%, at most about 96%, at most about 95%, at most about 90%, at most about 85%, at most about 80%, at most about 70% confidence intervals can be provided.

Patients can be grouped by clinical disease characteristics and molecular and immune profiles. These groups can be compared using t-tests for continuous variables, chi-square or exact tests for categorical variables, and/or log-rank tests for time-to-event variables. Associations between baseline variables (e.g., demographics, molecular and immune profiles) and patient outcomes can be investigated using a number of multiple regression methods, including, but not limited to, generalized linear models, mixed-effects and marginal models (for longitudinal data) or proportional hazards models (for time-to-event data). Because of the high-dimensional nature of molecular and immune data, approaches such as random forests can be used to select and classify variables when appropriate. Other variable reduction methods such as principle components analysis and hierarchical clustering can also be employed. The multiple testing problem for these data can be addressed using methods based on the false discovery rate (FDR).

Due to the observational nature of this study and the lack of randomization, covariate adjustments can be made to control for biases and confounding factors in all change-from-baseline measures, as between-cohort differences due to differences arising at baseline. Additional control for selection bias can be provided by the use of propensity scores. Baseline scores can be included as a covariate when change from a baseline of that score is analyzed.

For those patients who are lost to follow-up, or who drop out of the study, efforts can be made to obtain up-to-date survival status and the analyses can include all data up to the point of last data collection. If necessary, multiple imputation techniques for missing data can be used. Interim statistical analyses can be conducted during the study.

In some embodiments, interim statistical analyses can be conducted every 6 months following first patient in for the duration of the study.

In some embodiments, interim statistical analyses can be conducted every month, every 2 months, every 3 months, every 4 months, every 5 months, every 6 months, every 7 months, every 8 months, every 9 months, every 12 months, every 18 months, or every 24 months following the first patient in for the duration of the study.

In some embodiments, at least about 50, at least about 100, at least about 150, at least about 200, at least about 250, at least about 300, at least about 400, at least about 500, at least about 600, at least about 700, at least about 800, at least about 900, at least about 1000, at least about 1500, at least about 2000, at least about 3000, at least about 5000, at least about 10000 patients, or more, can be enrolled in the study every six months.

In some embodiments, at most about 10000, at most about 5000, at most about 3000, at most about 2000, at most about 1500, at most about 1000, at most about 900, at most about 800, at most about 700, at most about 600, at most about 500, at most about 400, at most about 300, at most about 250, at most about 200, at most about 150, at most about 100, at most about 50 patients, or less, can be enrolled in the study every six months.

For example, after 12, 18, and 24 months of patient enrollment, approximately 1000, 2000, and 3000 patients, respectively, can have enrolled. Interim statistical analyses reviews the distributions of treatment patterns and/or genetic characteristics. If these analyses suggest that higher proportions of patients in one or more subgroups are required, then recruitment can be adjusted accordingly.

In some embodiments, at the 24 month interim analysis, a minimum of about 100, about 200, about 300, about 400, about 500, about 600, about 700, about 800, about 900, about 1000, about 1100, about 1200, about 1300, about 1400, about 1500, about 2000, about 3000, or about 5000 patients, or more, can have encountered at least one year of follow up.

In some embodiments, at the 30 month interim analysis, a minimum of about 200, about 300, about 400, about 500, about 600, about 700, about 800, about 900, about 1000, about 1100, about 1200, about 1300, about 1400, about 1500, about 2000, about 3000, about 5000, or about 10000 patients, or more, can have encountered at least one year of follow up.

In some embodiments, at the 36 month interim analysis, a minimum of about 500, about 1000, about 1500, about 2000, about 3000, about 3500, about 4000, about 4500, about 5000, about 10000, or about 20000 patients, or more, can have encountered at least one year of follow up.

For example, at the 24-, 30-, and 36-month interim analyses, a minimum of 1000, 2000, and 3000 patients, respectively, can have encountered at least one-year of follow-up. At these analyses, assumptions and power of the study can be re-evaluated to detect clinically meaningful results. These re-evaluations can inform any changes in recruitment strategy.

F. Social Media

The integrated patient data registry can allow participants to interact with one another. In some embodiments, the integrated patient data registry can share scientific findings to the participant, researcher, and physician communities. In some embodiments, the integrated patient data registry can share announcements to the participant, researcher, and physician communities.

Computer Architectures

Figure 2:
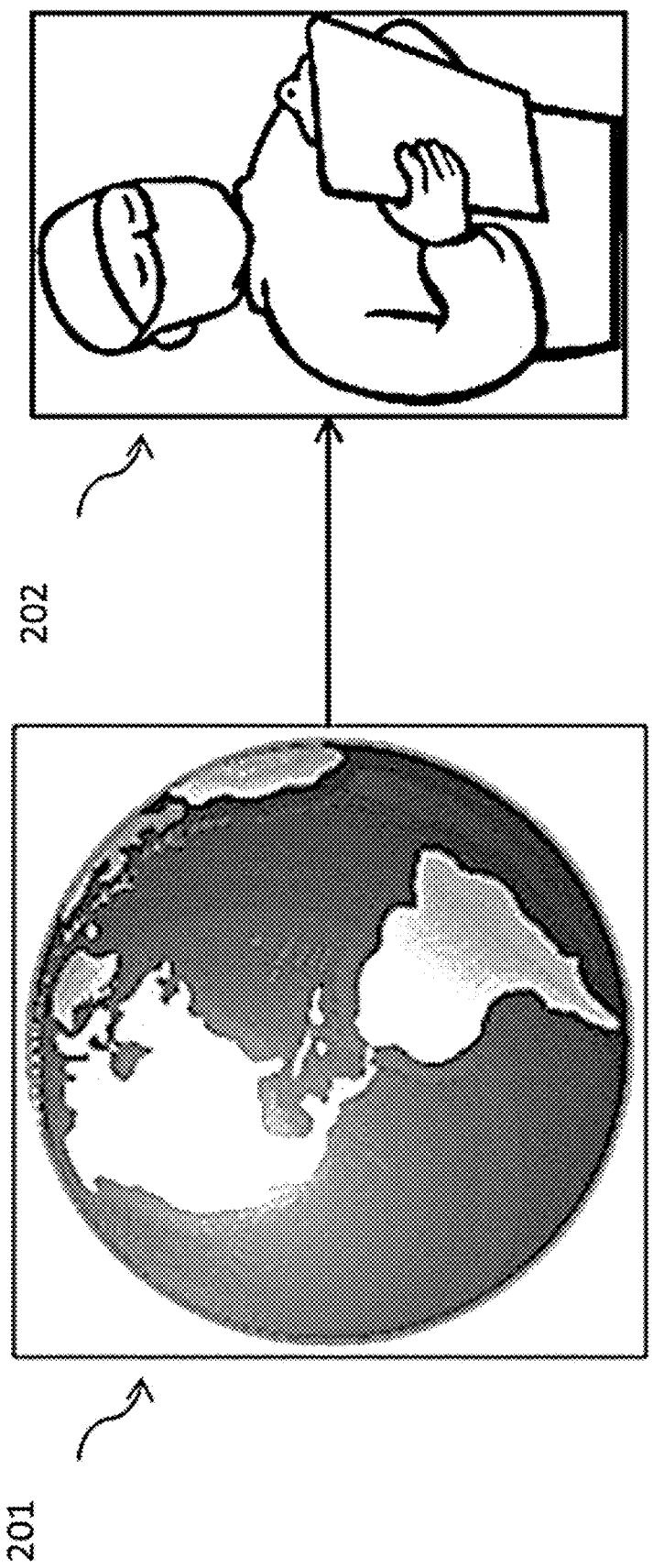
FIG. 2 illustrates a computer program product that is transmitted from a geographic location to a user.

Any embodiment of the disclosure described herein can be, for example, produced and transmitted by a user within the same geographical location. A product of the disclosure can be, for example, produced and/or transmitted from a geographic location in one country and a user of the disclosure can be present in a different country. In some embodiments, the data accessed by a system of the disclosure is a computer program product that can be transmitted from one of a plurality of geographic locations (201) to a user (202). FIG. 2 illustrates a computer program product that is transmitted from a geographic location to a user. Data generated by a computer program product of the disclosure can be transmitted back and forth among a plurality of geographic locations. In some embodiments, data generated by a computer program product of the disclosure can be transmitted by a network connection, a secure network connection, an insecure network connection, an internet connection, or an intranet connection. In some embodiments, a system herein is encoded on a physical and tangible product.

Figure 3:
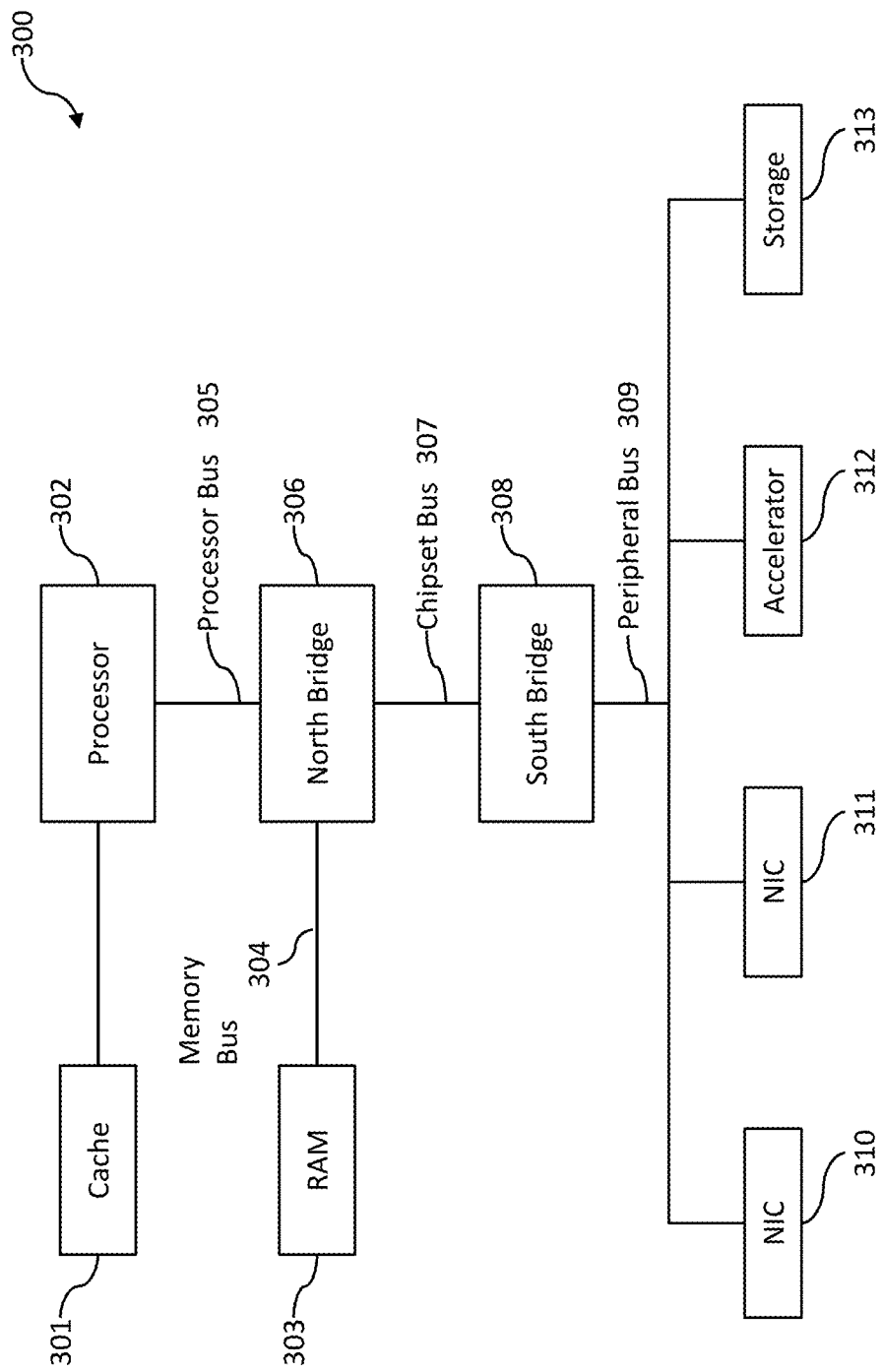
FIG. 3 is a block diagram that illustrates an example of a computer architecture system.

Various computer architectures are suitable for use with the disclosure. FIG. 3 is a block diagram that illustrates an example of a computer architecture system (300). The computer system (300) can be used in connection with example embodiments of the present disclosure. As depicted in FIG. 3, the example computer system can include a processor (302) for processing instructions. Non-limiting examples of processors include: Intel Core i7™, Intel Core i5™, Intel Core i3™, Intel Xeon™, AMD Opteron™, Samsung 32-bit RISC ARM 1176JZ(F)-S v1.0™ ARM Cortex-A8 Samsung S5PC100™, ARM Cortex-A8 Apple A4™, Marvell PXA 930™, or functionally-equivalent processors. Multiple threads of execution can be used for parallel processing. In some embodiments, multiple processors or processors with multiple cores can be used. In some embodiments, multiple processors or processors with multiple cores can be used in a single computer system, in a cluster, or distributed across systems over a network. In some embodiments, the multiple processors or processors with multiple cores can be distributed across systems over a network comprising a plurality of computers, cell phones, and/or personal data assistant devices a. Data Acquisition, Processing, and Storage A high speed cache (301) can be connected to, or incorporated in, the processor (302) to provide high speed memory for instructions or data that have been recently, or are frequently, used by the processor (302). The processor (302) is connected to a north bridge (306) by a processor bus (305). The north bridge (306) is connected to random access memory (RAM) (303) by a memory bus (304) and manages access to the RAM (303) by the processor (302). The north bridge (306) is also connected to a south bridge (308) by a chipset bus (307). The south bridge (308) is, in turn, connected to a peripheral bus (309). The peripheral bus can be, for example, PCI, PCI-X, PCI Express, or another peripheral bus. The north bridge and south bridge, often referred to as a processor chipset, manage data transfer between the processor, RAM, and peripheral components on the peripheral bus (309). In some computer architecture systems, the functionality of the north bridge can be incorporated into the processor instead of using a separate north bridge chip.

In some embodiments, the computer architecture system (300) can include an accelerator card (312). In some embodiments, the computer architecture system (300) can include an accelerator card that is attached to the peripheral bus (309). In some embodiments, the accelerator card (312) can include field programmable gate arrays (FPGAs) or other hardware for accelerating processing.

b. Software Interface(s)

Software and data are stored in an external storage module (313) and can be loaded into the RAM (303) and/or cache (301) for use by the processor. The computer architecture system can include an operating system for managing system resources. Non-limiting examples of operating systems include: Linux, Windows™, MACOS™, BlackBerry OS™, iOS™, and other functionally-equivalent operating systems. In some embodiments, the operating system can be application software running on top of an operating system.

In FIG. 3, the computer architecture system (300) also includes network interface cards (NICs) (310 and 311) that are connected to the peripheral bus to provide network interfaces to external storage. In some embodiments, the network interface card is a Network Attached Storage (NAS) device or another computer system that can be used for distributed parallel processing.

c. Computer Networks

Figure 4:
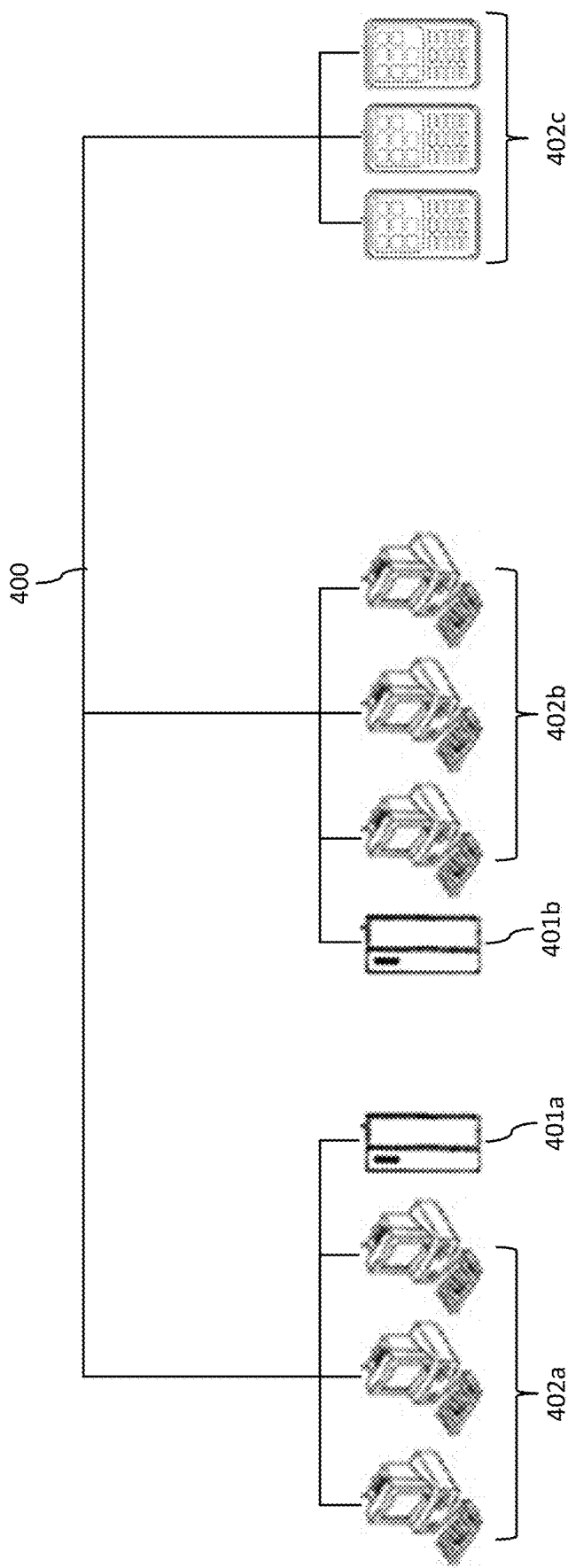
FIG. 4 is a diagram showing a computer network with a plurality of computer systems, a plurality of cell phones and personal data assistants, and NAS devices.

FIG. 4 is a diagram showing a computer network (400) with a plurality of computer systems (402a and 402b), a plurality of cell phones and personal data assistants (402c), and NAS devices (401a and 401b). In some embodiments, systems 402a, 402b, and 402c can manage data storage and optimize data access for data stored on NAS devices (401a and 402b). A mathematical model can be used to evaluate data using distributed parallel processing across computer systems (402a and 402b) and cell phone and personal data assistant systems (402c). Computer systems (402a and 402b) and cell phone and personal data assistant systems (402c) can also provide parallel processing for adaptive data restructuring of data stored on NAS devices (401a and 401b).

FIG. 4 illustrates an example only, and a wide variety of other computer architectures and systems can be used in conjunction with the various embodiments of the present disclosure. For example, a blade server can be used to provide parallel processing. Processor blades can be connected through a back plane to provide parallel processing.

Storage can also be connected to the back plane or a NAS device through a separate network interface.

In some embodiments, processors can maintain separate memory spaces and transmit data through network interfaces, back plane, or other connectors for parallel processing by other processors. In some embodiments, some or all of the processors can use a shared virtual address memory space.

d. Virtual Systems

Figure 5:
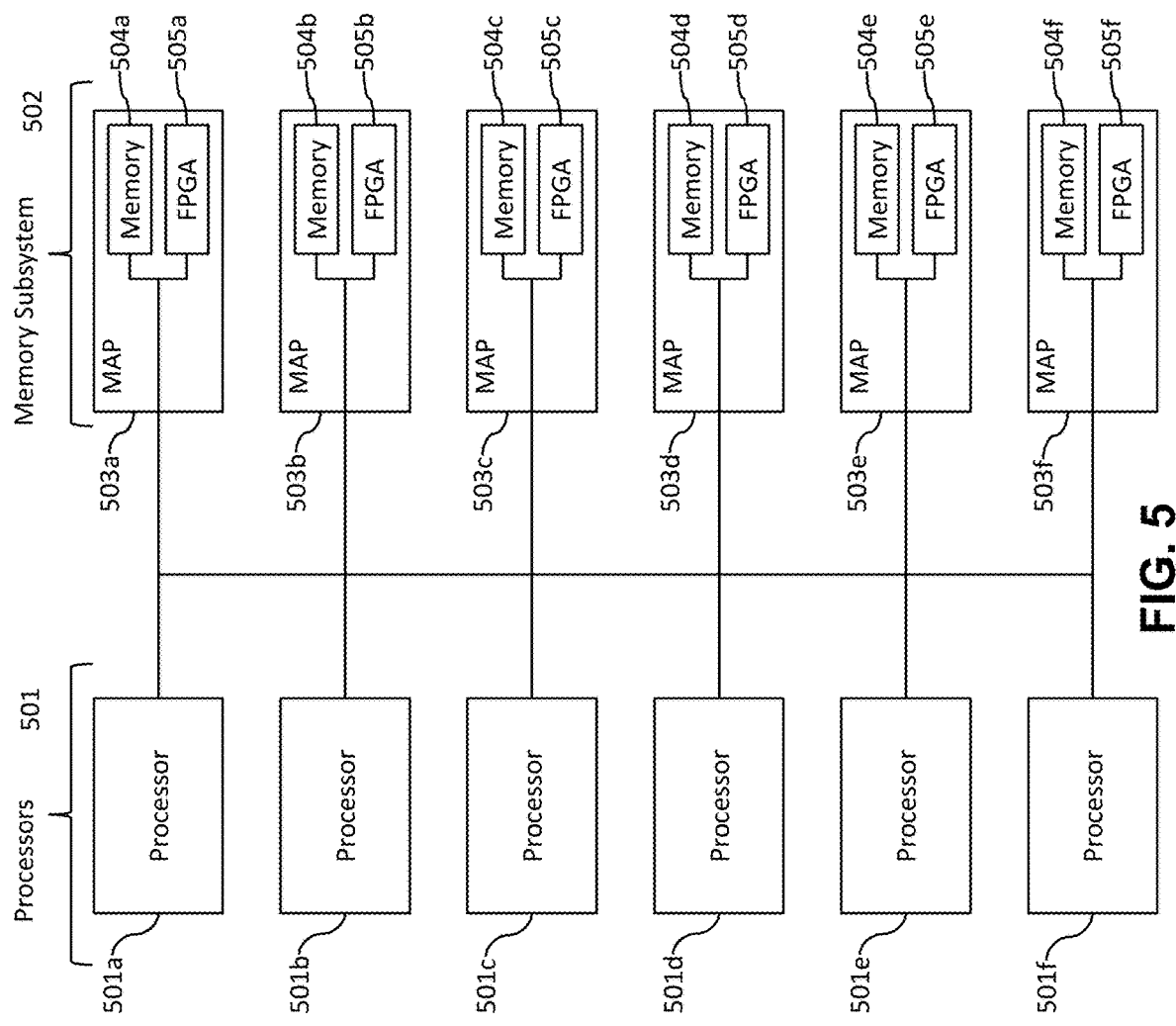
FIG. 5 is a block diagram of a multiprocessor computer system using a shared virtual address memory space.

FIG. 5 is a block diagram of a multiprocessor computer system using a shared virtual address memory space. The system includes a plurality of processors (501a-501f) that can access a shared memory subsystem (502). The system incorporates a plurality of programmable hardware memory algorithm processors (MAPs) (503a-503f) in the memory subsystem (502). Each MAP (503a-503f) can comprise a memory card (504a-504f) and one or more field programmable gate arrays (FPGAs) (505a-505f). The MAPs provide configurable functional units. Algorithms or portions of algorithms can be provided to the FPGAs (505a-505f) for processing in close coordination with a respective processor. In some embodiments, each MAP is globally accessible by all of the processors. In some embodiments, each MAP can use Direct Memory Access (DMA) to access an associated memory card (504a-504f), allowing it to execute tasks independently of, and asynchronously from, the respective microprocessor (501a-501f). In some this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments. In some embodiments, the systems of the disclosure can use any combination of general processors, co-processors, FPGAs and other programmable logic devices, system on chips (SOCs), application specific integrated circuits (ASICs), and other processing and logic elements. Any variety of data storage media can be used in connection with example embodiments, including, but not limited to, RAM, hard drives, flash memory, tape drives, disk arrays, NAS devices, and other local or distributed data storage devices and systems.

In some embodiments, the computer system can be implemented using software modules executed on any of the computer architectures and systems descried above. In some embodiments, the functions of the system can be implemented partially or completely in firmware or programmable logic devices (e.g., FPGAs) as referenced in FIG. 5, system on chips (SOCs), application specific integrated circuits (ASICs), or other processing and logic elements. For example, the Set Processor and Optimizer can be implemented with hardware acceleration through the use of a hardware accelerator card, such as, but not limited to, an accelerator card (512) illustrated in FIG. 5.

EMBODIMENTS

The following non-limiting embodiments provide illustrative examples of the disclosure, but do not limit the scope of the disclosure.

Embodiment 1

A method comprising:
a) collecting a subject's health data from a data source;
b) analyzing by a processor of a computer system the subject's health data to identify a plan of care needed by the subject, wherein the analyzing comprises characterization of the subject's molecular biology;
c) visualizing by the processor of the computer system the subject's plan of care; and
d) communicating by a patient-facing interface the subject's plan of care to the subject, a physician, and a researcher.

Embodiment 2

The method of embodiment 1, wherein the data source is the subject's electronic medical record (EMR) or electronic health record (EHR).

Embodiment 3

The method of embodiments 1 or 2, wherein the data source is a biological sample collected from the subject.

Embodiment 4

The method of any one of embodiments 1-3, wherein the biological sample is a blood sample, a tumor sample, or a saliva sample collected from the subject.

Embodiment 5

The method of any one of embodiments 1-4, wherein the characterization of the subject's molecular biology comprises characterizing the subject's immune phenotype based on data obtained from the biological sample.

Embodiment 6

The method of any one of embodiments 1-4, wherein the characterization of the subject's molecular biology comprises characterizing the subject's proteomics data based on data obtained from the sample.

Embodiment 7

The method of any one of embodiments 1-4, wherein the characterization of the subject's molecular biology comprises characterizing the subject's genomics data based on data obtained from the sample.

Embodiment 8

The method of any one of embodiments 1-7, wherein the visualizing comprises a chart, graph, cartoon, or animation.

Embodiment 9

The method of any one of embodiments 1-7, wherein the visualizing illustrates a time progression curve of the subject's health data.

Embodiment 10

The method of any one of embodiments 1-7, wherein the visualizing illustrates demographic data of the subject.

Embodiment 11

The method of any one of embodiments 1-10, wherein the communicating comprises a message between the subject and the physician.

Embodiment 12

The method of any one of embodiment 1-10, wherein the communicating comprises a message between the physician and the researcher.

Embodiment 13

A computer program product comprising a non-transitory computer-readable medium having computer-executable code encoded therein, the computer-executable code adapted to be executed to implement a method comprising:
  a) providing a healthcare management system, wherein the healthcare management system comprises:
    i) a data collection module;
    ii) a parameter selection module;
    iii) an analytics module, wherein the analytics module analyzes molecular biology data;
    iv) a visualization module, wherein the visualization module illustrates the data analyzed by the analytics module; and
    v) an output module comprising a patient-facing interface;
  b) collecting by the data collection module a subject's health data from a data source;
  c) selecting by the parameter selection module a set of parameters to use to analyze the subject's health data;
  d) analyzing by the analytics module the subject's health data using the set of parameters to provide an analysis;
  e) generating by the visualization module a visual representation of the analysis, and sending the visual representation of the analysis to the output module;
  f) outputting the visual presentation of the analysis.

Embodiment 14

The computer program product of embodiment 13, wherein the healthcare management system further comprises an online consent module, wherein the method further comprises enrolling the subject in the healthcare management system through the online consent module.

Embodiment 15

The computer program product of embodiments 13 or 14, wherein the enrolling through the online consent module triggers a collection of a biological sample from the subject, wherein the collection of the biological sample from the subject comprises mailing instructions to the subject to submit the biological sample to a laboratory.

Embodiment 16

The computer program product of any one of embodiments 13-15, wherein the data source is the subject's electronic medical record (EMR) or electronic health record (EHR).

Embodiment 17

The computer program product of any one of embodiments 13-15, wherein the data source is a database containing data from a biological sample collected from the subject.

Embodiment 18

The computer program product of any one of embodiments 13-17, wherein the analytics module characterizes the molecular biology data of the subject, wherein the molecular biology data is an immune phenotype of the subject based on the subject's health data.

Embodiment 19

The computer program product of any one of embodiments 13-17, wherein the analytics module characterizes the molecular biology data of the subject, wherein the molecular biology data is proteomics data of the subject based on the subject's health data.

Embodiment 20

The computer program product of any one of embodiments 13-17, wherein the analytics module characterizes the molecular biology data of the subject, wherein the molecular biology data is genomics data of the subject based on the subject's health data.

Embodiment 21

The computer program product of any one of embodiments 13-20, wherein the set of parameters comprises demographic information of the subject.

Embodiment 22

The computer program product of any one of embodiments 13-20, wherein the set of parameters comprises a disease status of the subject.

Embodiment 23

The computer program product of any one of embodiments 13-22, wherein the visual representation comprises a time progression curve of the subject's health data.

Embodiment 24

The computer program product of any one of embodiments 13-22, wherein the visual representation comprises demographic data of the subject.

Embodiment 25

The computer program product of any one of embodiments 13-24, wherein the healthcare management system further comprises a messaging system for communication among the subject, a physician, and a researcher.

Embodiment 26

The computer program product of any one of embodiments 13-25, wherein the messaging system communicates the message between the subject and the physician.

Embodiment 27

The computer program product of any one of embodiments 13-25, wherein the messaging system communicates the message between the physician and the researcher.

What is claimed is:

1. A computer program product comprising a non-transitory computer-readable medium having computer-executable code encoded therein, the computer-executable code adapted to be executed to implement a method for automating a healthcare process, the method comprising:
   a) providing a healthcare management system, wherein the healthcare management system comprises:
      i) a subportal;
      ii) an eligibility determination module;
      iii) an online consent module;
      iv) a parameter selection module;
      v) a data analysis module;
      vi) a visualization module;
      vii) an output module; and
      viii) a data abstraction and aggregation portal;
   b) receiving, from a subject via the subportal, information regarding the subject wherein the information comprises an indicator of a disease;
   c) determining, by the eligibility determination module, eligibility of the subject for inclusion in an integrated clinical database based on the received information regarding the subject before accessing an electronic medical record (EMR) database;
   d) triggering, by the online consent module, transmission of an online consent form to the subject when the subject is determined to be eligible for inclusion in the integrated clinical database;
   e) in response to receiving a consent in the online consent form, automatically triggering a transmission of medical data related to the subject from the EMR database to the subportal, via the data abstraction and aggregation portal, wherein the data abstraction and aggregation portal is configured to curate the medical data into structured medical data;
   f) processing, by the subportal, data obtained from a biological sample from the subject, thereby generating processed data, wherein the subportal is configured to generate the processed data by applying a variable reduction algorithm to the data obtained from the biological sample and the structured medical data;
   g) selecting, by the parameter selection module, a parameter describing the subject;
   h) analyzing, by the data analysis module, the processed data using the parameter describing the subject, thereby generating analyzed data specific to the subject;
   i) generating, by the visualization module, a visual representation of the analyzed data specific to the subject, and sending the visual representation of the analyzed data specific to the subject to the output module; and
   j) outputting, by the output module, the visual representation of the analyzed data specific to the subject to a portal.

2. The computer program product of claim 1, wherein the method further comprises enrolling the subject in the healthcare management system through the online consent module when the subject is determined to be eligible for inclusion in the integrated clinical database.

3. The computer program product of claim 2, wherein the enrolling through the online consent module triggers a collection of the biological sample from the subject, wherein the collection of the biological sample from the subject comprises mailing instructions to the subject to submit the biological sample to a laboratory.

4. The computer program product of claim 1, wherein the analyzed data specific to the subject is an immune phenotype of the subject.

5. The computer program product of claim 1, wherein the analyzed data specific to the subject is proteomics data of the subject.

6. The computer program product of claim 1, wherein the analyzed data specific to the subject is genomics data of the subject.

7. The computer program product of claim 1, wherein the parameter comprises demographic information of the subject.

8. The computer program product of claim 1, wherein the parameter comprises a disease status of the subject.

9. The computer program product of claim 1, wherein the visual representation comprises demographic data of the subject.

10. The computer program product of claim 1, wherein the healthcare management system further comprises a system for communication among the subject, a physician, and a researcher.

11. The computer program product of claim 1, wherein the method further comprises:
   a) identifying, by the data analysis module, a plan of care that is needed by the subject based on the analyzed data specific to the subject, and
   b) communicating, by the output module, the plan of care to the subject based on the analyzed data specific to the subject.

12. The computer program product of claim 1, wherein the method further comprises sending, by the healthcare management system, to the subject a privacy authorization form that allows for request of medical records of the subject from a provider of the subject.

13. The computer program product of claim 1, wherein the healthcare management system further comprises a sample collection module, and the method further comprises instructing, by the sample collection module, shipment of a sample collection kit to the subject when the subject consents to the online consent form.

14. The computer program product of claim 1, wherein the healthcare management system further comprises a participant survey module, and the method further comprises automatically triggering a transmission by the participant survey module, a survey to the subject when the subject consents to the online consent form.

15. The computer program product of claim 13, wherein the method further comprises transmitting, by the sample collection module, a blood sample request and label printing to the subject when the subject consents to the online consent form.

16. The computer program product of claim 1, wherein the visualization representation comprises: (i) a first visual representation of the analyzed data specific to the subject and wherein the first visual representation is configured to engage the subject in a course of treatment personalized for the subject and includes information about the subject relative to a group of subjects, and (ii) a second visual representation of the analyzed data specific to the group of subjects, wherein the second visual representation is different from the first visual representation and wherein the output module outputs the first visual representation of the analyzed data specific to the subject to a first portal and outputs the second visual representation of the analyzed data to a second portal.

17. The computer program product of claim 16, wherein the first visual representation is displayed in a personal visualization format that is customized to the subject.

18. The computer program product of claim 16, wherein the second portal permits a physician to modify the course of treatment personalized for the subject.

* * * * *